United States Patent
Beeckman et al.

(10) Patent No.: US 9,944,941 B2
(45) Date of Patent: Apr. 17, 2018

(54) GENES INVOLVED IN ASYMMETRIC CELL DIVISION

(71) Applicants: VIB VZW, Ghent (BE); Universiteit Gent, Ghent (BE)

(72) Inventors: Tom Beeckman, Merelbeke (BE); Ive De Smet, Ghent (BE); Steffen Vanneste, Lauwe (BE)

(73) Assignees: VIB VZW, Ghent (BE); UNIVERSITEIT GENT, Ghent (BE)

( * ) Notice: Subject to any disclaimer, the term of this patent is extended or adjusted under 35 U.S.C. 154(b) by 117 days.

(21) Appl. No.: 14/733,653

(22) Filed: Jun. 8, 2015

(65) Prior Publication Data

US 2015/0267217 A1  Sep. 24, 2015

Related U.S. Application Data

(62) Division of application No. 11/990,959, filed as application No. PCT/EP2006/065739 on Aug. 28, 2006, now Pat. No. 9,102,748.

(30) Foreign Application Priority Data

Aug. 26, 2005 (EP) .................................. 05107830

(51) Int. Cl.
   *C12N 15/82* (2006.01)
   *C12N 15/10* (2006.01)
   *C07K 14/415* (2006.01)
   *C12Q 1/68* (2018.01)

(52) U.S. Cl.
   CPC ........ *C12N 15/8267* (2013.01); *C07K 14/415* (2013.01); *C12N 15/1003* (2013.01); *C12N 15/1072* (2013.01); *C12N 15/8216* (2013.01); *C12Q 1/6895* (2013.01); *C12Q 2600/156* (2013.01); *C12Q 2600/16* (2013.01)

(58) Field of Classification Search
   None
   See application file for complete search history.

(56) References Cited

U.S. PATENT DOCUMENTS 7,345,217 B2 *  3/2008  Zhang .................. C07K 14/415
                                                   435/320.1
2003/0121070 A1 *  6/2003  Adam ................ C12N 15/8261
                                                   800/278

FOREIGN PATENT DOCUMENTS

WO         0244337 A2    6/2002
WO       2004031349 A2   4/2004
WO       2007023190 A2   3/2007

OTHER PUBLICATIONS

Bowie et al, Science 247:1306-1310, 1990.*
McConnell et al, Nature 411 (6838):709-713, 2001.*
Jeon, J. et al. The Plant Cell (Aug. 2016); vol. 28, pp. 18281843.*
Brady et al., The Abscisic Acid Insensitive 3 (ABI3) Gene is Modulated by Farnesylation and is Involved in Auxin Signaling and Lateral Root Development in Arabidopsis, The Plant Journal, 2003, pp. 67-75, vol. 34.
Burssens et al., Developmental Expression of the Arabidopsis thaliana CycA2;1 Gene, Planta, 2000, pp. 623-631, vol. 211.
Fukaki, H. et al., Lateral Root Formation is blocked by a Gain-Of-Function Mutation in the SOL/TARY-ROOT/IAA14 Gene of Arabidopsis, The Plant Journal, vol. 29, No. 2, (2002), pp. 153-168.
Himanen, K. et al., Transcript Profiling of Early Lateral Root Initiation, PNAS, vol. 101, No. 14, (2004), pp. 5146-5151.
Neuteboom, L.W., et al., Isolation and Characterization of cDNA Clones Corresponding with mRNAs that Accumulate During Auxin Induced Lateral Root Formation, Plant Molecular Biolo., vol. 39, 1999, pp. 273-287.
Vanneste, S. et al., Cell Cycle Progression in the Pericycle is not Sufficient for SOLITARY ROOT/IAA14-mediated Lateral Root Initiation in Arabidopsis thaliana, The Plant Cell, vol. 17, No. 11, (2005), pp. 3035-3050.
Yang et al., 2001, PNAS 98(20):11438-11443.
Okada et al., 1998, Journal of Plant Research 111 :315-322.
Haseloff, J., (1998, Catalogue of GAL4-GFP enhancer trap lines [http;//brindabella.mrc-lmb.cam.ac.uk]).
Birnbaum et al., 2005, Nature Methods 2(8):615-619.

* cited by examiner

*Primary Examiner* — Russell Kallis
(74) *Attorney, Agent, or Firm* — TraskBritt, P.C.

(57) ABSTRACT

Described are methods of isolating genes involved in the process of asymmetric cell division. Further disclosed are genes isolated with this method, and their use in controlling root formation, preferably lateral root formation.

4 Claims, 7 Drawing Sheets
(6 of 7 Drawing Sheet(s) Filed in Color)

GENES INVOLVED IN ASYMMETRIC CELL DIVISION

RELATED APPLICATIONS

This application is a divisional of U.S. patent application Ser. No. 11/990,959, filed May 9, 2008, now U.S. Pat. No. 9,102,748 (Aug. 11, 2015), which application is a national stage application (under 35 U.S.C. § 371) of PCT/EP2006/065739 filed Aug. 28, 2006, designating the United States of America and published in English as International Patent Publication WO 2007/023190 A2 on Mar. 1, 2007, which claims the benefit under Article 8 of the Patent Cooperation Treaty to European Patent Application Serial No. 05107830.1 filed Aug. 26, 2005, the disclosure of each of which is hereby incorporated herein in its entirety by this reference.

TECHNICAL FIELD

The disclosure relates to plant biotechnology. Disclosed are, among other things, methods of isolating genes involved in the process of asymmetric cell division. Further disclosed are genes isolated using the method, and their use in controlling root formation, such as lateral root formation.

BACKGROUND

To generate the multitude of different cell types present in multicellular organisms, cell divisions resulting in daughter cells with different fates are vital and decisive in various developmental processes (Scheres and Benfey, 1999). This type of division is called asymmetric, whether or not asymmetry is morphologically visible at the time of division (Horvitz and Herskowitz, 1992). Especially in plants, where cell movement is limited, the control of the cell division plane has traditionally been considered important for the formation of regular patterns, i.e., correct divisions during embryogenesis or stomata formation, the formation of ordered cell files in the meristem (Scheres and Benfey, 1999).

During a plant life cycle, several asymmetric divisions occur: (a) the first division of the zygote (Mansfield and Briarty, 1991); (b) the embryonic division that gives rise to the lens-shaped progenitor cell of the quiescent center (Dolan et al., 1993); (c) the male microspore division (Twell et al., 1998); (d) divisions during stomatal complex formation (Larkin et al., 1997); (e) oriented periclinal divisions in the early embryo that separate the progenitor cells for the three main tissues, epidermis, ground tissue, and vascular tissue (Jurgens and Mayer, 1994); (f) stem cell divisions that separate differentiation-competent daughter cells and new stem cells in the root (Dolan et al., 1993; van den Berg et al., 1995); and (g) also during lateral root initiation (Casimiro et al., 2003).

Asymmetric divisions fundamentally differ from the standard proliferative divisions in their limited spatio-temporal way of occurrence. Furthermore, the number of cells involved is minimal. These characteristics make it difficult to analyze (genome wide) transcript expression during this process.

Up until now, only a few transcript profiling experiments have been performed in various organisms on processes where asymmetric cell divisions are involved, i.e., during gliogenesis in *Drosophila* (Egger et al., 2002), *Arabidopsis* pollen development (Honys and Twell, 2003, 2004; Becker et al, 2003) and lateral root initiation (Himanen et al., 2004). However, none of these approaches aimed at or resulted in the identification of the genetic pathway driving the asymmetric division itself.

In the case of lateral root initiation, a few pericycle cells divide anticlinally and asymmetrically (Casero et al., 1993). This is not a continuous process and is exposed to various environmental cues and endogenous signals. Furthermore, these divisions only occur in those pericycle cell files that are in close proximity to the xylem pole (Casimiro et al., 2003).

Microarray approaches have revealed a broader view on auxin signaling toward LRI (Himanen et al., 2004). For these analyses, a lateral root inducible system was used. In this system, auxin transport, signaling and the G1-to-S cell cycle transition are blocked in seedlings growing on medium supplemented with NPA. Subsequently, these seedlings are transferred to auxin-containing medium (NAA) for 1-12 hours. This allowed an inducible startup of auxin signaling and progression through the G1-to-S transition (Himanen et al., 2002).

An adaptation of this lateral root inducible system can also be used for the study of asymmetric cell divisions. A unique approach is presented that allowed circumvention of problems like tissue specificity and the limited number of cells involved through isolating specifically asymmetrically dividing pericycle cells at the xylem pole during LRI. Therefore, four strategies were combined: 1) a recently developed lateral root inducible system that synchronously induces the asymmetric divisions during LRI (Himanen et al., 2002), 2) a xylem pole pericycle-specific GFP marker line (J0121), 3) a Fluorescent Assisted Cell Sorting approach (Birnbaum et al., 2003), and 4) genome-wide microarray analysis on the isolated xylem pole pericycle cells. This combined strategy not only allowed identification of those genes involved directly in the LRI process, but also extrapolation of the results to the general concept of asymmetric division. Potential regulators of asymmetric divisions were found in genes involved in cell cycle regulation and a high percentage of genes associated with cytoskeleton organization and dynamics.

BRIEF SUMMARY

Provided is a method of isolating genes involved in asymmetric cell division, the metho comprising: (1) subjecting roots of a wild-type plant to a treatment inducing lateral root initiation in a synchronous way; (2) subjecting roots of a mutant not developing lateral roots by a defect in auxin signaling to a treatment inducing lateral root initiation in wild-type in a synchronous way; (3) identifying genes that are induced in wild-type but not in mutant; (4) identifying genes induced in the xylem pole pericycle in wild-type during lateral root initiation. "Early lateral root initiation," as used herein, means the events at different stages just prior to the first division in the pericycle. Preferably, this is within 10 hours after auxin induction of the lateral root, more preferably within 8 hours of induction, even more preferably, 6 hours after induction. Preferably, the mutant used is a slr-1 mutant.

Preferably, the method further comprises the use of a xylem pole pericycle marker line, followed by cell sorting. Even more preferably, the marker is GFP. Most preferably, the isolated cells are genome-wide analyzed by microarray analysis.

Also disclosed is a gene involved in early lateral root formation, which may be isolated with a method according to the disclosure. Preferably, the gene encodes a transcription factor. Even more preferably, the transcription factor is selected from the group consisting of SEQ ID NO:1 to SEQ ID NO:19.

As transcription factors often are expressed in the tissue of activity, their promoters are likely to be of economical use. Such promoters can be used in several strategies to enhance pathogen tolerance/resistance of the plant.

Another aspect of the disclosure is a gene involved in asymmetric cell division, which may be isolated with a method according to the disclosure. Preferably, the method further comprises the use of a xylem pole pericycle marker line, followed by cell sorting. Even more preferably, the gene comprises a polynucleotide encoding a protein selected from the group consisting of SEQ ID NO:20 through SEQ ID NO:34, or a homologue thereof.

Still another aspect of the disclosure is a transcription factor involved in early lateral root formation, wherein the transcription factor is selected from the group consisting of SEQ ID NO:1 to SEQ ID NO:19. Preferably, the gene encoding the transcription factor is isolated with a method of the disclosure.

A further aspect of the disclosure is the use of a gene, isolated with the method of the disclosure, to modulate early lateral root initiation. "Modulation," as used herein, may be an increase or a decrease in number of lateral roots, it may be an increase or decrease in size of the lateral roots or it may be a shift in time (earlier or later in plant development) of lateral root formation. Preferably, modulation is an increase or decrease in lateral roots; even more preferably, it is an increase in lateral roots. Preferably, the gene encodes a transcription factor. Even more preferably, the gene encodes a transcription factor selected from the group consisting of SEQ ID NO:1 to SEQ ID NO:34, or a homologue thereof. The genes may be used in combination to increase the effect on lateral root formation.

"Gene," as used herein, refers both to the genomic sequence (including possible introns) as well as to the cDNA derived from the spliced messenger. It may refer to the promoter sequence too. However, it is clear for the person skilled in the art that for some applications, the coding sequence, such as it may be derived from cDNA, may be operably linked to a suitable promoter. "Operably linked" refers to a juxtaposition wherein the components so described are in a relationship permitting them to function in their intended manner. A promoter sequence "operably linked" to a coding sequence is ligated in such a way that expression of the coding sequence is achieved under conditions compatible with the promoter sequence.

A "homologue," as used herein, means that the protein encoded by the gene has an amino acid sequence that is at least 75% identical, and even more preferably, at least 80% identical, and even more preferably, at least 85% identical, and even more preferably, at least 90% identical, and even more preferably, at least 95% identical, and even more preferably, at least 96% identical, and even more preferably, at least 97% identical, and even more preferably, at least 98% identical, and even more preferably, at least 99% identical, as measured by a BLASTP search (Altschul et al., 1997).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Examples

Materials and Methods to the Examples

Figure 1:
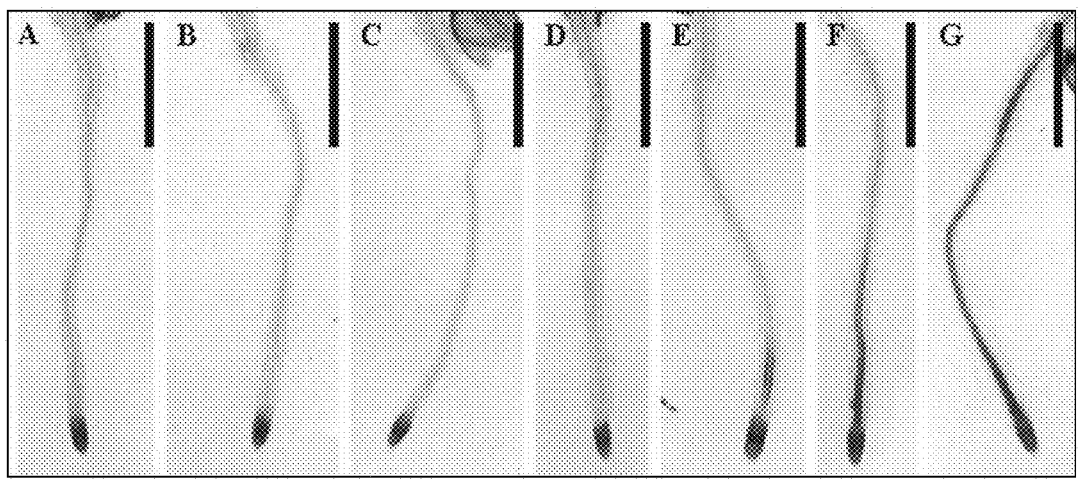
FIG. 1: Lateral root inducible system (Columns A-G) Time series of 12 hours of NAA treatment (blue staining=P:: GUS reporter activity of Arath;CYCB1;1 marking G2/M transition). The auxin transport inhibition blocks all lateral root initiation, allowing synchronous induction of lateral roots via auxin, resulting in the onset of G2/M transition 6 to 8 hours after transfer to auxin medium (Columns D, E).

WT Col-Slr Comparison-Based Approach
Sampling

In the lateral root inducible system, seeds (Col-0 and slr-1) were germinated on standard Murashige and Skoog media containing 10 µM N-NaphtylPhtalamic Acid (NPA) on vertically oriented square plates (Greiner Labortechnik, Frickenhausen, Germany) in a growth chamber under continuous light (110 µE·m-2·s-1 PAR supplied by cool-white fluorescent tungsten tubes [Osram, München, Germany]) at 22° C. (Himanen et al., 2002). Seventy-two hours after germination (0 hour time point), only those seedlings (wild-type and mutant) that made full contact with the medium were transferred to medium containing 10 µM NaphtylAcetic Acid (NAA) and harvested after two hours and six hours. These three time points were applied for both wild-type and mutant. A mock treatment was included for wild-type only, by transferring the seedlings to standard Murashige and Skoog medium without NAA addition. For all time points, only the lateral root inducible segments were used for the analysis. For this purpose, the root apical meristem and hypocotyl were manually removed to minimize contamination with other cell types. All treatments were repeated.

Microarray and Clustering

RNA was extracted using the RNEASY® Minikit (Qiagen). RNA quality and quantity were analyzed using RNA 6000 Nano Lab Chip Kit (Agilent Technologies, Germany). For microarray, 5.8 µg total RNA was used. Double-stranded cDNA was synthesized with Life Technologies cDNA Synthesis Kit. The double-stranded cDNA was converted to biotin-labelled cRNA (Ambion MEGA script T7 in vitro transcription kit and biotin-containing ribonucleotides from Enzo (LOXO GmbH)). Fifteen µg of fragmented cRNA was used for hybridization to ATH1 AFFYMETRIX® gene-chips. The biotin-labelled RNA was visualized with phycoerythrin-streptavidin labels. ATH1 gene-chips (Affymetrix) represent 22747 *Arabidopsis* genes (~85% predicted genes in the *Arabidopsis* genome).

The overall signal of the different chips was normalized using Microarray Suite 5.0 software (Affymetrix). The raw data were exponentially distributed and were, therefore, $\log_2$-transformed before further statistics. Statistical significance was analyzed via ANalysis Of VAriance (ANOVA) for every gene. This resulted in a p-value for three sources of variance: the effect of the time course, the effect of the genotype and the effect of their interaction. For the genome-wide transcript profiling, the stringency was increased to p<0.001. This is the equivalent of 23 false positive tests if 22747 tests are performed. At this level of significance, 3110 genes were flagged.

There was a need to detect differences between the expression profiles in both genotypes, so a tool to optimally visualize these differences was required. This tool was obtained by merging time course data for both genotypes per time point. This merged dataset was subsequently treated as if it was a single time course (repeated time points are indicated with *) (0/0*/2/2*/6/6*). Before clustering, an estimate of the predictive power of a clustering algorithm (Figure Of Merit) was computed over a range of clusters. The lower the Figure Of Merit, the higher the predictive power of the clustering will be (Yeung et al., 2001). The number of clusters, for which the smallest increment did not result in a decrease of the Figure Of Merit, was chosen as the optimal cluster number. All clustering computation was performed using TIGR Multi-experiment Viewer 2.2 (tigr.org webpage, Oct. 11, 2003).

Each gene was related to two clusters, representing its average expression profile in both wild-type and mutant. The combinational potential was represented in a cross-table format with indication of the frequency of occurrence of each combination. As an indicator of differences between clusters, a color code was applied. For all clusters, the relative induction/reduction rates of the expression profiles between zero and 2 hours and between zero and 6 hours of the average profiles were compared to one another. If these relative induction/reduction rates differed two-fold or more at one of these levels of comparison, an orange or blue color was assigned to this cluster combination. If these relative induction/reduction rates differed at both levels two-fold or more, a red color was assigned to this cluster combination. A cluster was considered as up-regulated when the rate of induction of the expression level was stronger than two-fold for both intervals (0-2 and 0-6). Only clusters 1, 2, 3 and 4 met these criteria.

Cell Sorting Approach
Sampling

In the lateral root inducible system, seeds (J0121, plantsci.cam.ac.uk/Haseloff/geneControl/catalogues/Jlines/record/record_0.html webpage) were germinated (Himanen et al., 2002). As described above, seedlings were harvested after 2 hours and 6 hours. For all time points, the roots were cut into small 0.5 mm fragments, and those segments were protoplasted according to Birnbaum et al. (2003, 2005). GFP-expressing cells were isolated on a fluorescence-activated cell sorter (Becton Dickinson FACSVantage). The cells were sorted directly into lysis buffer (Qiagen RLT buffer), mixed and immediately frozen at −80° C. for later RNA extraction. All treatments were repeated.

Microarray and Clustering

Standard AFFYMETRIX® protocols for small samples were then used for amplifying, labeling and hybridizing RNA samples (wi.mit.edu/CMT/protocols/AffySmlSamplProto.pdf webpage). The hybridized cRNA was fragmented as described in the GENECHIP® Expression Analysis Technical Manual. The hybridization, washing and staining steps were performed according to the Affymetric protocols (wi.mit.edu/CMT/protocols/Affymetrix%20User%20Manual.pdf webpage).

The data were processed using a Mixed Model. This mixed-model analysis of variance was performed to identify genes differentially expressed between the various treatments (Chu et al., 2002, 2004). In this approach, a global normalization step was applied to minimize general array-level effects by centering the mean of the $\log_2$-transformed values to zero for each array (Chu et al., 2002). Outlier probes with values greater than two standard deviations from the probe-set mean were then removed. Next, a mixed-model ANOVA was applied to the transformed and centered intensity values obtained from the global normalization step. This gene model, which is based on that developed by Chu et al. (2002), can be formalized as:

$$\log_2(PM_{jkl}) = T_j + P_k + A_{l(j)} + \varepsilon_{jkl}$$

where the PM variable refers to the output of the global normalization procedure for each gene, as described above. The symbols T, P, and A represent treatment, probe, and array effects, respectively. The array effect $A_{l(j)}$ is assumed to be a normally distributed random effect (Chu et al., 2002). A standard error term $\varepsilon_{jkl}$ was also applied to this model. In addition, the indices j, k, and l represent the jth treatment, on the kth probe, and on the lth replicate (Chu et al., 2002). The output of this model is the mean expression value for every gene, based on the global model, as well as a p-value from the gene-model for the probability of falsely rejecting the null hypothesis of no-differential expression ($\alpha$=0.05). The global and gene models were run on a LINUX® server with the statistical software SAS (version 8.2).

Grouping of the 1920 significantly differentially expressed genes coming out of the statistical analysis into 10 clusters, was done using TIGR MeV 3.0.3 (Saeed et al., 2003).

Example 1: Sampling and Microarray Analysis

Recently, an auxin-based lateral root inducible system was developed (Himanen et al., 2002). Based on this unique, in planta inducible system, a genome-wide transcript profiling was performed to identify key regulators of lateral root initiation. To facilitate the identification of those genes with a role in auxin signaling in relation to lateral root initiation, a mutant was included as a negative control. The mutant (solitary root) was mainly selected for its inability to form lateral roots and because the affected gene is involved in a known part of auxin signaling (Fukaki et al., 2002). The comparison of wild-type and mutant in the lateral root inducible system is of fundamental importance to select genes involved in lateral root initiation, downstream of the protein affected in the mutant (IAA14/SLR).

Figure 2:
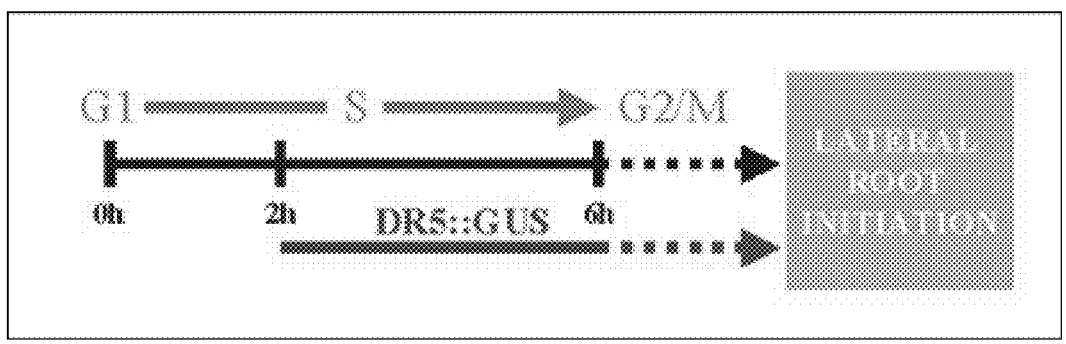
FIG. 2: Scheme of main events during lateral root initiation.

Time points were chosen in such a way that allowed monitoring gene expression at different stages just prior to the first division in the pericycle. Himanen et al. (2002) showed that this event occurs 8 to 10 hours after transfer to auxin-containing medium. The zero time point (72 hours NPA) is consistent with a G1/S-blocked state, while six hours after transfer to auxin, pericycle cells adjacent to the xylem poles are nearly starting G2/M transition. Furthermore, the earliest auxin response in the root was visualized with a DR5::GUS reported 1.5 to 2 hours after auxin treatment (FIG. 2). Therefore, a time point (2 hours NAA) was included to represent this earliest auxin-modulated transcription.

Both wild-type and mutant (slr-1) were subjected to these treatments. Additionally, a mock-treatment was included for wild-type to assess differential gene expression due to the transfer. All treatments were biologically repeated, adding to the statistical significance of the data.

Example 2: Statistical Analysis and Clustering

After normalization and transformation, the data were subjected to ANOVA analysis. Comparison of the previous limited transcript profiling (on 4600 genes) (Himanen et al., unpublished results) with the present one, clearly shows that our lateral root inducible system is highly reproducible, since 64% of the differentially expressed genes were confirmed when checked at the same level of significance ($p<0.005$). In order to reduce the amount of false positives even further, a five-fold higher stringency ($p<0.001$) was applied than in the previous transcript profiling. At this high stringency level, 3110 genes were still differentially regulated.

Figure 3:
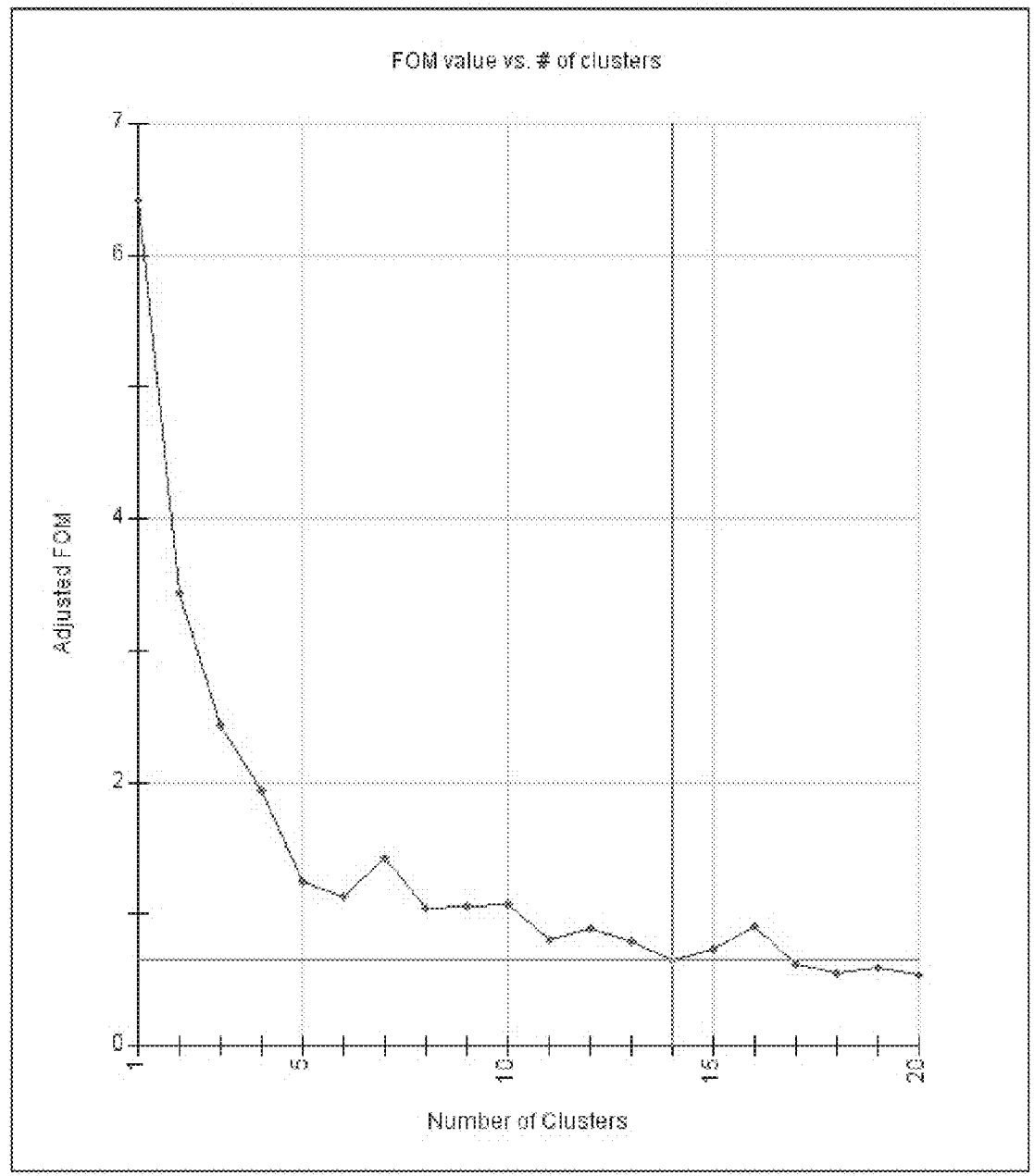
FIG. 3: Figure Of Merit calculation for a range to 20 clusters.

Clustering of all data-points for both wild-type and solitary root separately did not meet the needs to assess the differences in expression profiles in both genotypes. In order to meet this criterion, the data for both genotypes were combined into one dataset. Each gene was represented twice in the combined dataset, resulting in 6220 expression profiles. In order to estimate the optimal number of clusters, the Figure Of Merit (FOM) was computed for a range of clusters. The smallest FOM was estimated at 14 clusters, representing the optimal number of clusters corresponding to the highest predictive power (FIG. 3).

Figure 4:
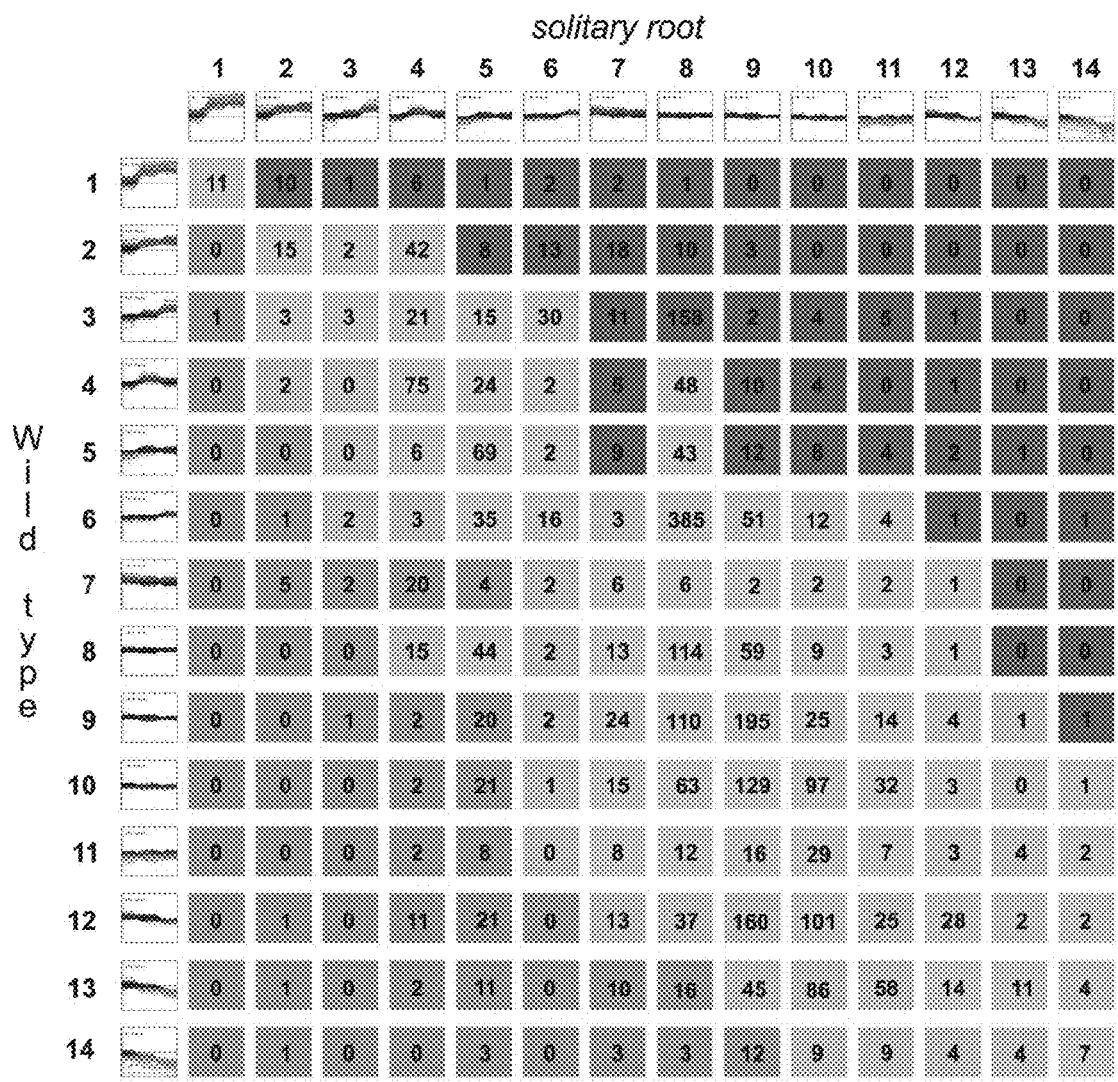
FIG. 4: Cross-table representation with the frequencies of all combinations of expression profiles.

Subsequently, all 6220 expression profiles were clustered into 14 clusters. In this way, two coordinates were assigned per gene, representing the expression profiles in both genotypes. All 196 (14×14) potential combinations are represented in FIG. 4, together with the absolute frequency of genes in each combination. Differences between clusters are indicated through a color code.

The genes indicated in red (305) represent the genes for which wild-type gene expression is always higher than in solitary root. Genes of this kind, induced in wild-type and less in solitary root, are most likely involved in lateral root initiation. Therefore, focus was on the genes, represented as clusters 1, 2, 3 and 4 in wild-type. In this way, the total number of significantly regulated genes (3110) was narrowed down to 266 (~9%) that might have a crucial role in lateral root initiation.

Example 3: Effect of Filtering on General Functional Categories

A comparison of the percentages of genes belonging to a functional category before and after clustering according to MATDB (MIPS *Arabidopsis Thaliana* DataBase) nicely illustrates the effectiveness of the cross-table-based clustering (Table 1). The filtering procedure clearly resulted in an enrichment for genes related to cell cycle, RNA processing, DNA synthesis and signaling and development. These features confirm that the monitoring of cell cycle progression in the pericycle is possible using the lateral root inducible system. Furthermore, a higher percentage of genes involved in transcriptional regulation were found, indicating that there is a general need for increased transcriptional activity. The percentage of unclassified and unknown genes remains at about the same level. Moreover, a strong relative reduction of genes involved in stress, transport and metabolism was achieved through the applied selection criteria. In addition, the drop in the number of genes involved in transport might also be categorized as a drop in number of genes related to detoxification and stress responses.

Example 4: Cell Cycle Regulation During Lateral Root Initiation

Detailed examination of the selection reveals G1/S and S-phase markers such as Arath;CYCD3;2 and Arath;CYCA2;4. Furthermore, the link to S-phase entry/progression is never far-off as there is a high representation of genes involved in DNA replication and protein synthesis. This underlines the suitability of this approach to study auxin-mediated cell cycle regulation. As interesting as core cell cycle events can be, they require upstream signaling cascades such as auxin signaling.

Example 5: Auxin Signaling During Lateral Root Initiation

In this stringent selection, several genes were detected belonging to gene families with known roles in auxin signaling such as Aux/IAAs, ARFs, ATGH3s and an ATSAUR (Hagen and Guilfoyle, 2000). Different mutants in genes belonging to the Aux/IAA gene family have lateral root phenotypes (Fukaki et al., 2002; Park et al., 2002). Their gene products act to repress the activity of ARF transcription factor dimers (Leyser, 2002).

Recently, researchers gained insight into the function of ATGH3-gene products, through the analysis of activation tagged lines (Takase et al., 2004). Several of these GH3 proteins have been shown to adenylate plant hormones and based on their substrate specificity and protein structure, they are subdivided into three major classes (Staswick et al., 2002). The members of group II, such as ATGH3-1, ATGH3-5 and ATGH3-6/DFL1, can adenylate IAA, negatively regulating auxin activity (Takase et al., 2004).

As for the Small Auxin Up RNAs (ATSAUR), very little is known about their function in auxin response. However, their auxin inducibility has been reported for several years (McClure and Guilfoyle, 1989).

Example 6: New Genes in Lateral Root Initiation: Transcription Factors

As transcription factors play central roles in patterning and development (Sabatini et al., 2003), it is obvious that such genes in this selection (19) will be of particular importance in the signaling cascades during lateral root initiation (Table 1). Most of the genes of this selection were recently shown to be specifically expressed in stele tissue (including the pericycle) by a transcript profiling study of the *Arabidopsis* root tip (Birnbaum et al., 2003), justifying the selection criteria used in the study.

Interestingly, two of the AP2 domain transcription factors belong to the same subclade. This implicates that it is likely that these genes have redundant functions. Furthermore, there is one AP2 domain transcription factor that belongs to this same subclade of three genes, which is not represented on the microarray (Alonso et al., 2003). It is hypothesized that this gene (At4g27950) could also be functionally redundant to the two other members of this subclade. Consequently, this gene was also added to the selection, bringing the final number of the selection to 20 genes.

Within the dataset, there are 15 transcription factors for which no role in auxin signaling has been suggested. As for a start of validation, it will be of primary interest to do a functional analysis on these transcription factors with respect to lateral root initiation.

Many of these transcription factors have great potential for involvement in lateral root development, as they have homologues for which a role in organ development has been reported. The ABI3 gene was previously described as a seed-specific gene, but recently, it has been shown to have a role in auxin signaling and lateral root development (Brady et al., 2003). Also, AP2 and several homeobox genes have been shown to be involved in floral organ development, which implies that homologs have great potential to be essential in the development of other organs such as lateral roots (Carpenter and Coen, 1990; Maes et al., 1999).

Interestingly, there is one transcription factor, MYB124, for which the mutant has an aberrant stomatal development. As the result of the mutation, stomata with four guard cells are formed instead of two (Yang and Sack, 1995). Its up-regulation upon auxin treatment of the root implicates that the MYB124 gene product might have as crucial a role in the formative divisions in the pericycle (lateral root initiation) as it has in stomatal development.

Example 7: Identifying Asymmetric Cell Division Genes

Using LRI as a model to genetically dissect the asymmetric cell division, it was investigated which cluster within the ten clusters contained the putative regulators of this type of division.

First, it was analyzed which cluster is strongly linked with the G2-to-M transition by verifying the expression profile during cell cycle progression using the genome-wide expression data for synchronized *Arabidopsis* cell suspensions (Menges et al., 2003). It was found that 48% of the genes in cluster 3 peaked at the G2-to-M transition. This is opposed to less than 10% of the genes that peaked at this transition in all the other clusters. This is a strong overrepresentation of G2-to-M-related genes within this cluster as compared to the other clusters. Furthermore, this is 59% of the G2-to-M-specific genes present in the whole dataset.

Secondly, which cluster is potentially correlated with asymmetric cell division was analyzed. For this, protein sequences of genes were used that are assigned to the functional categories (godatabase.org/cgi-bin/amigo/go.cgi webpage) "asymmetric cell division" and/or "establishment and/or maintenance of cell polarity" in a wide variety of organisms i.e., *Caenorhabditis elegans, Drosophila melanogaster, Schizosaccharomyces pombe*, mouse . . . ). A protein blast analysis was performed with the protein sequences of various organisms and those *Arabidopsis* protein sequences of the genes assigned to the different clusters. This resulted in an overrepresentation of 54 genes putatively correlated with "asymmetric cell division," "cell fate commitment" and/or "establishment and/or maintenance of cell polarity" in cluster 3.

To further analyze the process of asymmetric cell division, focus was on, therefore, the 340 genes within cluster 3. Within this cluster, 25% of the genes have been described; the remaining 75% is unknown, expressed, hypothetical or putative.

In order to even further reduce the number of interesting candidates, those genes were subtracted of which involvement in normal cell division (synchronized, dividing *Arabidopsis* cell suspension cells) is shown (Menges et al., 2003). After that analysis, 190 candidates potentially involved in asymmetric cell division remained.

Example 8: Meta-Analysis for Improvement of the Results

It has been previously demonstrated that cell cycle progression in the pericycle is not sufficient for SOLITARY ROOT/IAA14-mediated lateral root initiation in *Arabidopsis thaliana* (Vanneste et al., 2005).

Figure 5:
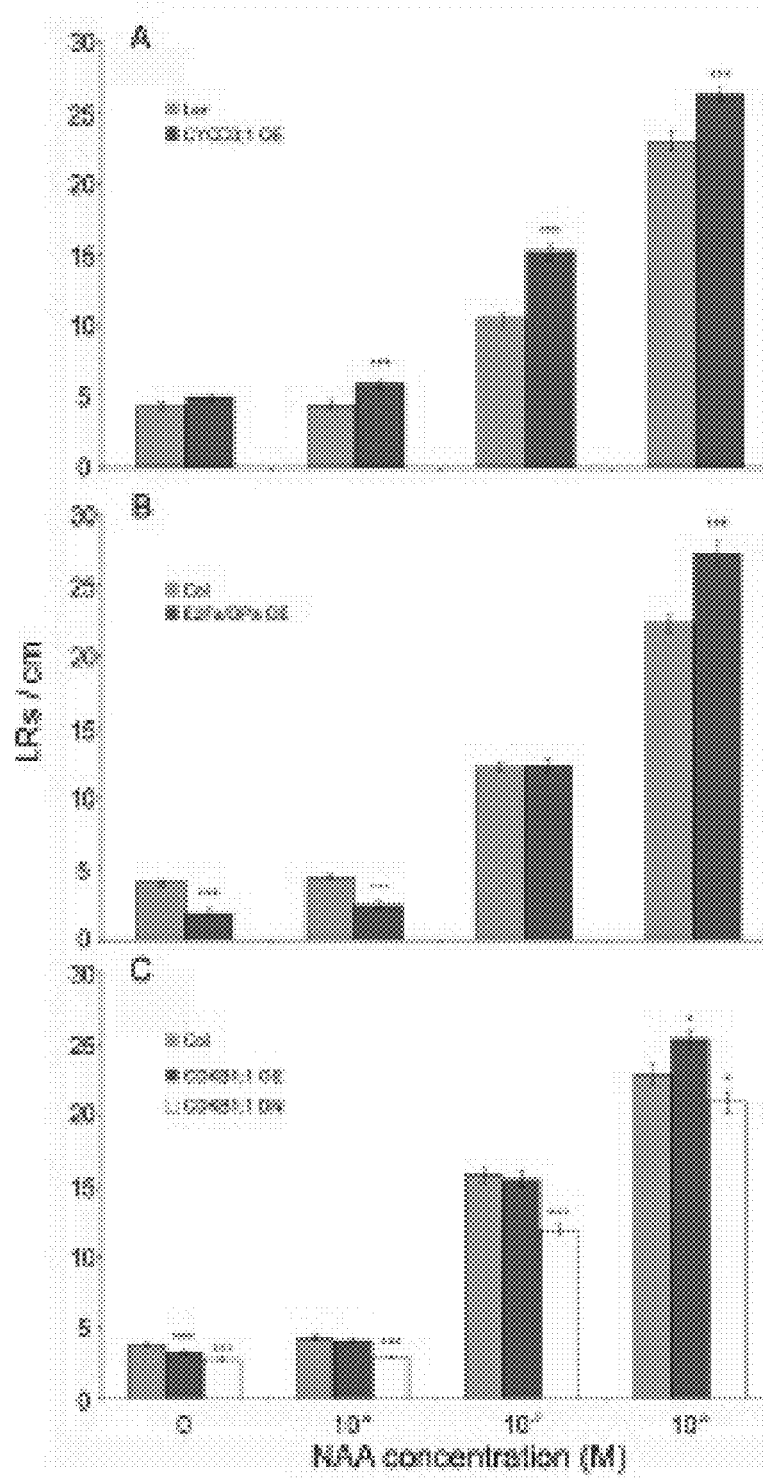
FIG. 5: Overexpression phenotype of CYCD3;1, E2Fa/DPa and CDKB1;1 in 10-day-old seedlings, as compared to wild-type.

To support this finding, the root phenotype of transgenic lines over-expressing (35S) cell cycle genes were analyzed. Based on the cell cycle stage-specific expression profiles upon lateral root induction shown in Himanen et al. (2002) and the dataset, CYCD3;1 (G1-to-S and G2-to-M, Dewitte and Murray, 2003), E2Fa/DPa (G1-to-S, De Veylder et al., 2002) and CDKB1;1 (G2-to-M, Boudolf et al., 2004) were selected. The over-expression phenotype in 10-day-old seedlings of all lines was analyzed and compared to WT (FIG. 5). None of the transgenic lines showed a significant increase in the lateral root density. The double transgenic over-expression line of E2Fa/DPa even showed a strong decrease in the lateral root number compared to the wild-type Col. Also, over-expression of CDKB1;1 resulted in fewer lateral roots. Furthermore, in the case of CDKB1;1, the over-expression of dominant negative allele of CDKB1;1 (CDKB1;1.N161) (Boudolf et al., 2004), resulted in a stronger decrease of the number of lateral roots.

Next, analysis was performed as to whether auxin (NAA) application in combination with increased cell cycle gene expression could result in a higher number of lateral roots compared to the auxin or cell cycle alone. Therefore, five-day-old seedlings of the above-mentioned transgenic *Arabidopsis* lines of E2Fa$^{OE}$, Dpa$^{OEOE}$, CYCD3;1$^{OE}$ and CDKB1;1$^{OE}$ were transferred to increasing concentrations of auxin ($10^{-8}$, $10^{-7}$ and $10^{-6}$ M of NAA) and, after another 5 days of growth, their ability to initiate lateral roots was analyzed. A significant increase was found in the CYCD3;1$^{OE}$ opposed to the wild-type. Similarly, the number of LRs/cm could be significantly increased in the E2Fa/DPa$^{OE}$ transgenic line, until exceeding the wild-type number at high auxin concentration. Even CDKB1;1$^{OE}$ exceeded the WT number upon auxin application, while this was not the case for the CDKB1;1DN$^{OE}$ line.

The above results indicate that stimulating the basic cell cycle machinery is not sufficient for de novo lateral root initiation, but when extra auxin is provided, the enhanced cell cycle competence can be exploited to produce new organs. This corroborates the suggestion by Vanneste et al. (2005) that, next to cell cycle activation, another factor is required to specifically drive lateral root initiation.

Notwithstanding a putative function for CDKB1;1 in lateral root initiation, cell cycle genes are clearly not the key regulators for lateral root initiation. Hence, a search was performed for potential specific regulators of lateral root initiation via meta-analysis within the dataset. This meta-analysis was performed to reduce the number of genes from 1920 significant genes to 15 highly interesting candidates (Table 3). The analysis involved subsequent steps of overlapping and in-depth analysis of subsets of genes as described below.
1) Affymetrix *Arabidopsis* ATH-1 Genome Array (22758 genes);
2) Unique significantly differentially expressed genes (1920);
3) Up-regulated genes in asymmetric cell division during lateral root initiation after selecting 1 cluster based on the following criteria (340) using in-depth analysis with functional categories terms:
highest % G2-M genes
highest % genes involved in asymmetry
highest % genes involved in polarity
highest % genes involved in cell fate;
4) Genes potentially involved in cell fate and cell polarity (190) after subtracting the mitotic apparatus based on Menges et al. (2003);
5) Genes involved in auxin-induced cell fate and/or cell polarity in the xylem pole pericycle during lateral root initiation (15) after overlapping the remaining 190 genes with those lateral root initiation genes (913) depending on rapid SLR/IAA14 degradation for normal auxin responsiveness, as derived from the cross-table (FIG. 4).

Example 9: BDL is Involved in Lateral Root Initiation

As was determined earlier (Vanneste et al., 2005), an important regulator mechanism for lateral root initiation is auxin signaling and transport. Table 4 lists the genes involved in those events and demonstrates that most of them are early up-/down-regulated. A number of genes have been shown to be involved in lateral root formation (ALF1/RTY/SUR1, Celenza et al., 1995, King et al., 1995, Boerjan et al., 1995; DFL1, Nakazawa et al., 2001) and for several Aux/IAAs and ARFs, a role in lateral root initiation and/or formation was shown earlier (IAA19/MSG2, Tatematsu et al., 2004; ARF19, Wilmoth et al., 2004; IAA1/AXR5, Yang et al., 2004; IAA3/SHY2, Tian and Reed, 1999).

Figure 6:
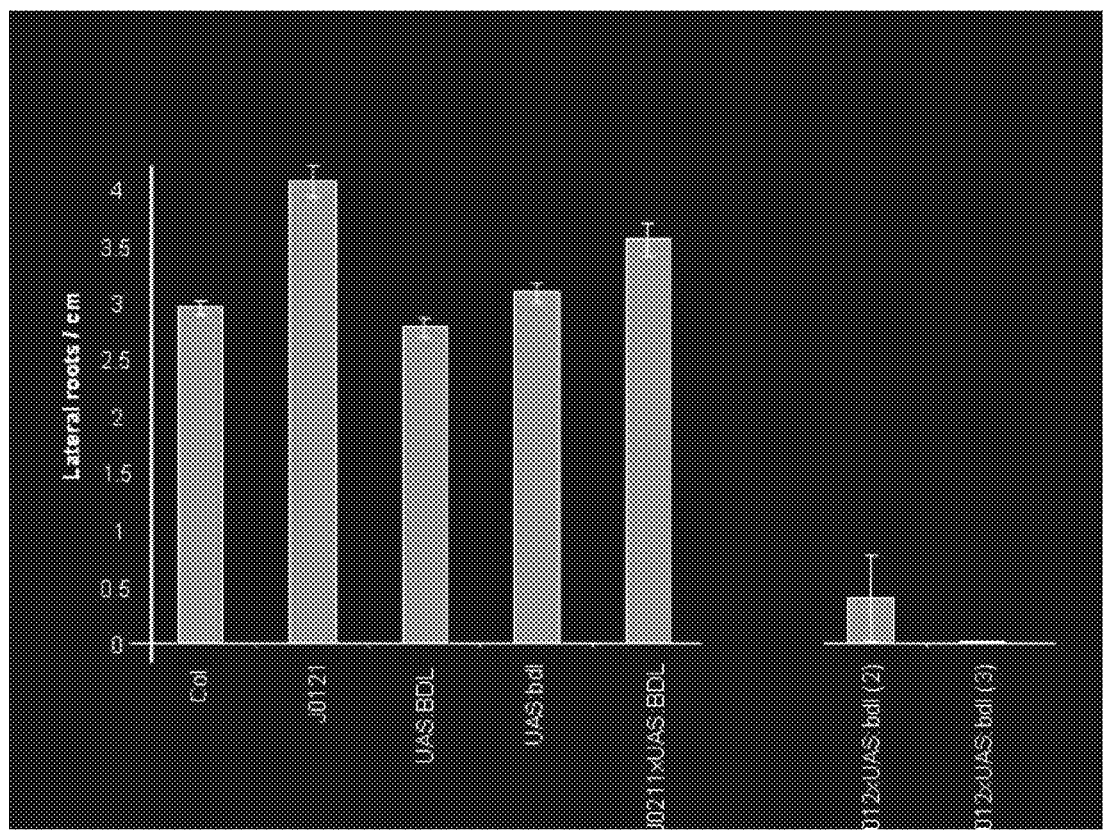
FIG. 6: Xylem pole pericycle specific expression of a stabilized mutant version of the BDL protein in J0121xUAS: bdl (0.0±0.0), resulting in a lateral rootless phenotype, while the control lines Col-0 (3.0±0.1), J0121 (4.1±0.1), UAS:bdl (3.1±0.1), UAS:BDL (2.8±0.1) and J0121xUAS:BDL (3.6±0.1) display no reduction in the number of lateral roots/cm.

For BDL/IAA12, part of a pair of transcriptional regulators with MP/ARF5, the involvement in lateral root initiation was demonstrated. Xylem pole pericycle-specific expression of a stabilized mutant version of the BDL protein in J0121xUAS:bdl (0.0±0.0) resulted in a lateral rootless phenotype, while the control lines Col-0 (3.0±0.1), J0121 (4.1±0.1), UAS:bdl (3.1±0.1), UAS:BDL (2.8±0.1) and J0121xUAS:BDL (3.6±0.1) displayed no reduction in the number of lateral roots/cm (FIG. 6).

Example 10: Role of CYCA2;4 in Lateral Root Formation

Figure 7:
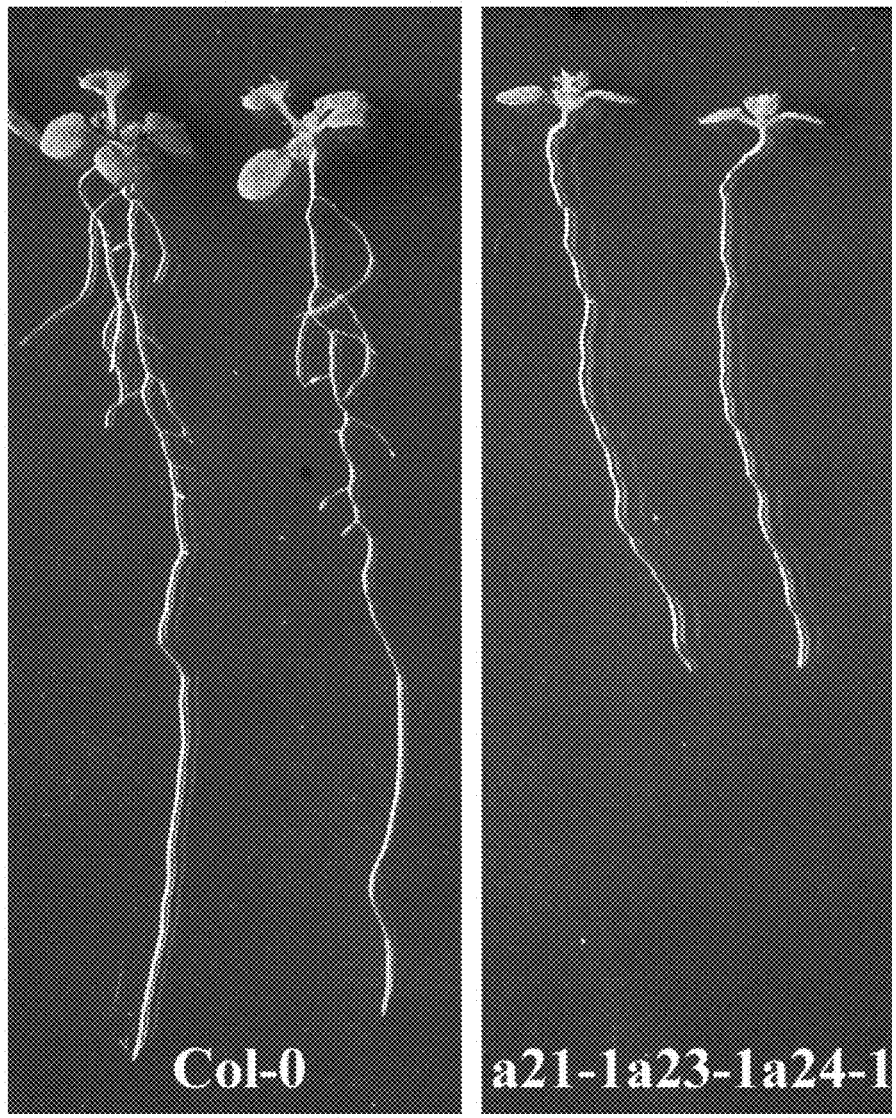
FIG. 7: Combined mutations in various members of the CYCA2;4 family results in dramatic reductions of lateral root density (left panel: Col-0 control; right panel: multiple mutant).

CYCA2;4 was identified as a putative important regulator of cell division during lateral root initiation (Vanneste et al., 2005). However, overexpression of CYCA2;4 did not induce an increase in lateral roots (similar to overexpression of other cell cycle genes), while it did stimulate cell cycle progression as exemplified by a strong reduction of endoreduplication level in cotyledons. Also, in knock-outs, no obvious changes in lateral root density were observed. But, CYCA2;4 belongs to a small gene family consisting of four members. Combining mutations in various members of this family did result in dramatic reductions of lateral root density (FIG. 7). Taken together, these data suggest that A2-type cyclins are required, but not sufficient for lateral root initiation to occur.

Interestingly, CYCA2;4—a core cell cycle gene—is retained in the list of genes after meta-analysis. Unfortunately, the lack of lateral root phenotype in the overexpression lines might suggest that a combination of genes/factors is required to specifically drive asymmetric cell division and lateral root initiation. The most likely candidates that, when combined, will induce lateral root initiation are within the subset of 15 genes identified under Example 8.

Example 11: Mutant Screening

Figure 8:
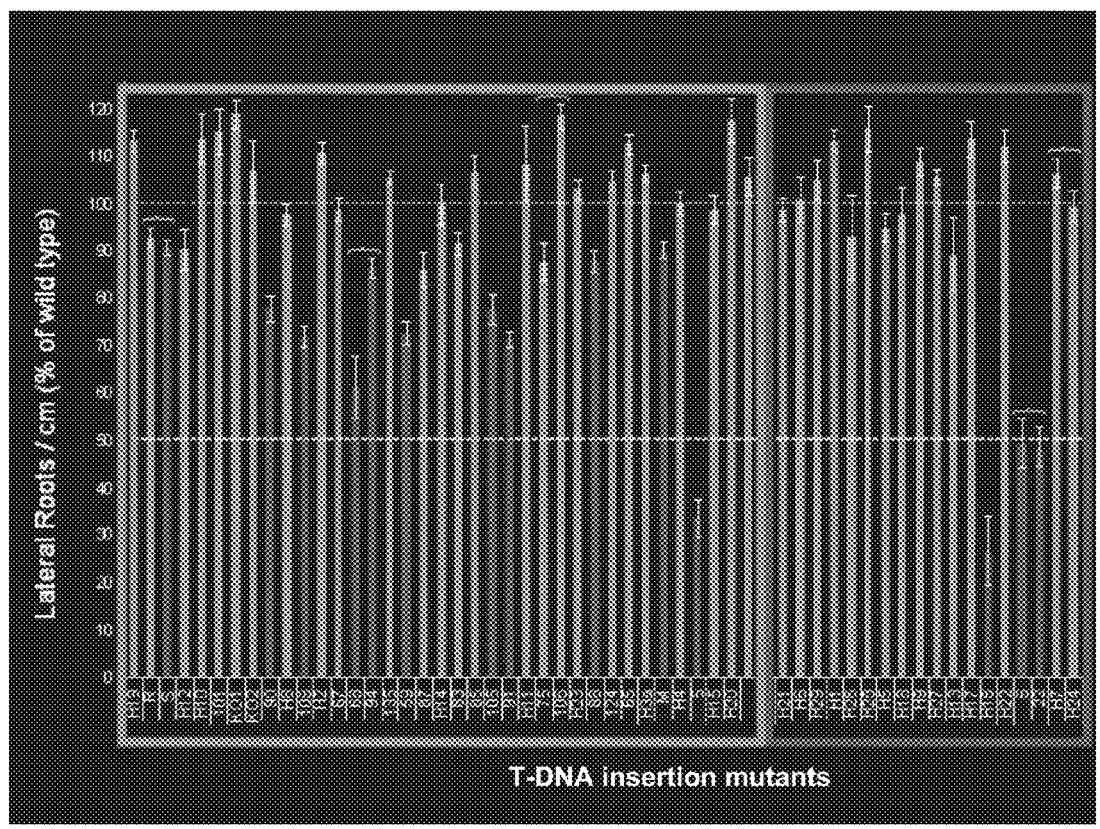
FIG. 8: Analysis of the lateral root phenotype of several homozygous SALK T-DNA insertion mutants, derived from genes in various clusters. The code of the mutants is listed in Table 5.

A number of SALK T-DNA insertion mutants from genes in various clusters were made homozygous and analyzed for their lateral root phenotype (FIG. 8). In the graph, bars of mutants with a significant increase or decrease in the lateral root number are colored green or red, respectively. The green or red box around part of the graph indicates genes from up- or down-regulated clusters, respectively.

In addition to the lateral root phenotype, defects in other processes requiring asymmetric cell divisions were also detected, i.e., stomata formation and embryogenesis.

Example 12: Expression Analysis by GUS/GFP Fusion

Figure 9:
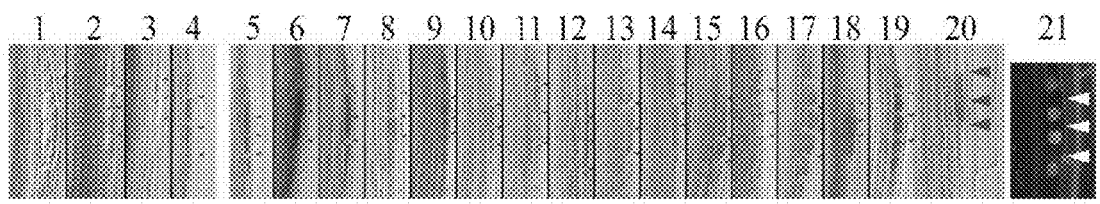
FIG. 9: Detailed analysis during early lateral root formation (asymmetric cell division is indicated by arrowheads) of various up- and down-regulated genes in the complete dataset. The numbers refer to the fusions listed in Table 6.

A number of promoter-GUS/GFP fusions from genes in various clusters were made homozygous and analyzed in detail for their expression pattern (FIG. 9). Mainly, the GUS/GFP expression pattern was in agreement with the up- or down-regulation of the gene in the microarray dataset.

For four genes, the expression pattern was analyzed in detail, and revealed a specific up- or down-regulation of the GUS/GFP in the lateral root initiation site at the time of asymmetric cell division in agreement with the transcript level detected in the microarray (FIG. 10).

Tables

TABLE 1

Overview of shifts in functional categories after filtering

| Functional categories | % in 3110 | % in 266 |
|---|---|---|
| Cell cycle/DNA synthesis | 3.9 | 8.3 |
| Kinase/Phosphatase | 5.5 | 3.4 |
| Metabolism/Energy | 22.7 | 12.4 |
| Protein synthesis/degradation | 9.7 | 9.0 |
| RNA processing | 1.6 | 3.0 |
| Signaling/development | 6.8 | 12.8 |
| Stress | 4.0 | 2.3 |
| Transcriptional activity | 10.9 | 14.7 |
| Transport | 7.2 | 2.3 |
| Other | 5.5 | 7.1 |
| Unclassified/unknown | 22.1 | 24.4 |

Lateral root initiation encrypted in 'lateral root initiation' genes

TABLE 2

List of up-regulated transcription factors that are not responsive in the mutant (slr)

| | | Cluster coordinates | |
|---|---|---|---|
| AGI code | Description | Wild-type | Solitary root |
| At2g33720 | ABI3/VP1-related TF | 4 | 7 |
| At5g53290 | AP2 domain TF | 1 | 4 |
| At4g23750 | AP2 domain TF | 1 | 6 |

TABLE 2-continued

List of up-regulated transcription factors that are not responsive in the mutant (slr)

| | | Cluster coordinates | |
|---|---|---|---|
| AGI code | Description | Wild-type | Solitary root |
| At5g18560 | AP2 domain TF | 1 | 8 |
| At1g28360 | AP2 domain TF | 2 | 8 |
| At5g10510 | AP2 domain TF | 3 | 8 |
| At5g57390 | AP2 domain TF | 3 | 8 |
| At4g28640 | Aux/IAA family (IAA11) | 1 | 2 |
| At4g32280 | Aux/IAA family (IAA29) | 1 | 2 |
| At3g62100 | Aux/IAA family (IAA30) | 1 | 4 |
| At5g43700 | Aux/IAA family (IAA4) | 2 | 5 |
| At5g60450 | Auxin Response Factor (ARF4) | 2 | 8 |
| At4g00940 | DOF zinc finger protein | 4 | 9 |
| At1g27050 | Homeobox TF | 2 | 7 |
| At2g01430 | Homeobox TF | 2 | 7 |
| At1g14350 | MYB domain TF (AtMYB124) | 2 | 5 |
| At1g18570 | MYB domain TF (AtMYB51) | 4 | 9 |
| At2g47260 | WRKY domain TF (WRKY23) | 3 | 7 |
| At5g26930 | GATA zinc finger protein | 1 | 4 |

TABLE 3

List of genes that are up-regulated in the xylem pole pericycle, that are not responsive in the slr mutant, and that show potential involvement in the asymmetric cell division

| AGI code | Description |
|---|---|
| AT5G63950 | SNF2 DOMAIN-CONTAINING PROTEIN/HELICASE DOMAIN-CONTAINING PROTEIN |
| AT5G67100 | DNA-DIRECTED DNA POLYMERASE ALPHA CATALYTIC SUBUNIT, PUTATIVE |
| AT2G33620 | DNA-BINDING FAMILY PROTEIN/AT-HOOK PROTEIN 1 (AHP1) |
| AT2G46990 | AUXIN-RESPONSIVE PROTEIN/INDOLEACETIC ACID-INDUCED PROTEIN 20 (IAA20) |
| AT5G47440 | EXPRESSED PROTEIN STRONG SIMILARITY TO UNKNOWN PROTEIN |
| AT4G32460 | EXPRESSED PROTEIN |
| AT4G13210 | PECTATE LYASE FAMILY PROTEIN |
| AT3G59430 | EXPRESSED PROTEIN |
| AT3G01070 | PLASTOCYANIN-LIKE DOMAIN-CONTAINING PROTEIN |
| AT3G59420 | RECEPTOR PROTEIN KINASE, PUTATIVE (ACR4) |
| AT1G80370 | CYCLIN, PUTATIVE |
| AT1G69530 | EXPANSIN, PUTATIVE (EXP1) |
| AT4G02060 | PROLIFERA PROTEIN (PRL)/DNA REPLICATION LICENSING FACTOR MCM7 (MCM7) |
| AT5G67070 | RAPID ALKALINIZATION FACTOR (RALF) FAMILY PROTEIN |
| AT1G61580 | 60S RIBOSOMAL PROTEIN L3 (RPL3B) |

TABLE 4

Expression in an early stage of genes involved in auxin signaling and transport as determined by the cell sorting approach.

| Gene Name(s) | agi | 0 h | 2 h | 6 h |
|---|---|---|---|---|
| AAP6 | At5g49630 | 0.852584 | 1.25473 | 1.549922 |
| ALF1 SUR1 RTY | AT2g20610 | 3.526627 | 1.659614 | 1.132184 |
| ARF16 | At4g30080 | 0.727253 | 1.044252 | 1.222434 |
| ARF18 | At3g61830 | 1.02858 | 1.042211 | 1.37744 |
| ARF19 | At1g19220 | 0.964729 | 2.260746 | 1.345781 |
| ARF4 | At5g60450 | 0.993832 | 2.433736 | 1.34132 |
| ARF5 IAA24 MP | At1g19850 | 0.805484 | 1.062866 | 1.646489 |
| AtGH3_1 | At2g14960 | 0.993763 | 14.46607 | 12.64589 |
| AtGH3_4 | At1g59500 | 1.832319 | 11.94342 | 5.062107 |
| AtGH3_5 | AT4g27260 | 4.933415 | 36.44469 | 28.02028 |
| AtGH3_6 DFL1 | At5g54510 | 4.107676 | 33.98892 | 33.18595 |
| ATSAUR32 | At2g46690 | 0.745399 | 1.083697 | 1.357203 |
| ATSAUR51 | At1g75580 | 0.641888 | 0.861681 | 1.394927 |
| DFL1 | AT5G54510 | 4.107676 | 33.98892 | 33.18595 |
| HAT2 | AT5G47370 | 3.866166 | 5.905478 | 1.72286 |
| IAA1 | AT4G14560 | 1.444098 | 2.650251 | 3.498028 |
| IAA11 | AT4G28640 | 1.081115 | 2.990535 | 3.893183 |
| IAA12 BDL | AT1G04550 | 1.070244 | 2.483024 | 2.141742 |
| IAA13 | AT2G33310 | 3.386846 | 16.95071 | 17.15706 |
| IAA17 AXR3 | AT1G04250 | 4.20049 | 5.560019 | 1.337217 |
| IAA19 MSG2 | AT3G15540 | 8.950041 | 37.74343 | 43.64249 |
| IAA20 | AT2G46990 | 0.643367 | 0.719127 | 1.830361 |
| IAA26 PAP1 | AT3G16500 | 1.67767 | 4.3412 | 2.185664 |
| IAA29 | AT4G32280 | 1.230655 | 15.62485 | 12.44667 |
| IAA3 SHY2 | AT1G04240 | 0.649735 | 1.143323 | 0.778411 |
| IAA5 | AT1G15580 | 0.800279 | 1.701733 | 2.127686 |
| PINOID-LIKE | At3g44610 | 0.730512 | 0.863134 | 2.114596 |

TABLE 5 code of the mutants used

| Code on graph | AGI |
|---|---|
| H19 | At3g59850 |
| R | At4g23750 |
| S | At4g23750 |
| H12 | At4g38210 |
| H10 | At5g15080 |
| 101 | At5g51560 |
| KO1 | At1g11140 |
| KO2 | At1g55580 |
| 90 | At1g57820 |
| H8 | At1g69530 |
| 108 | At1g72250 |
| H2 | At2g06850 |
| 67 | At2g22610 |
| 68 | At2g28620 |
| 94 | At2g28620 |
| 135 | AT2G33620 |
| 59 | At3g51280 |
| 87 | At3g51740 |
| H14 | At3g53190 |
| 83 | At4g02150 |
| 85 | At4g05190 |
| 105 | At4g18570 |
| 91 | At4g21820 |
| H11 | At4g29360 |
| 75 | At4g32830 |
| 106 | At4g32830 |
| H23 | At5g08000 |
| 88 | At5g45780 |
| 124 | At5g47440 |
| 65 | At5g48460 |
| H3a | At1g08840 |
| M | At1g72310 |
| H4 | At1g75640 |
| 5 | At4g28640 |
| H15 | At1g64390 |
| H20 | At3g58040 |
| H21 | At1g14720 |
| H6 | At1g29050 |
| H29 | At1g53500 |
| H1 | At1g60610 |
| H26 | At2g45470 |
| H28 | At3g10810 |
| H5 | At3g52370 |
| H18 | At4g03960 |
| H9 | At4g14130 |
| H27 | At5g18650 |
| H13 | At5g38895 |
| H17 | At5g54160 |
| H16 | At5g57740 |
| H22 | At5g03650 |

TABLE 5-continued code of the mutants used

| Code on graph | AGI |
|---|---|
| 6 | At2g33830 |
| 22 | At2g33830 |
| H7 | At3g54920 |
| H24 | At3g54920 |

TABLE 6 genes used in GUS fusion

| | |
|---|---|
| 1 | pAt4g13770::GUS |
| 2 | pAT2G20610::GUS |
| 3 | pAt3g46130::GUS |
| 4 | pAt3g11280::GUS |
| 5 | pAt1g49740::GUS |
| 6 | pAt1g64405::GUS |
| 7 | pAt3g55620::GUS |
| 8 | pCYCB1;1::GUS |
| 9 | pCYCB1;3::GUS |
| 10 | pCYCB2;2::GUS |
| 11 | pCYCB2;4::GUS |
| 12 | pCYCA2;2::GUS |
| 13 | pCYCA2;3::GUS |
| 14 | pCDKB2;2::GUS |
| 15 | pCKS2::GUS |
| 16 | pDEL3::GUS |
| 17 | pAt3g58100::GUS |
| 18 | pAt1g54990::GUS |
| 19 | pAt5g26930::GUS |
| 20 | pAT1G69530::GUS |
| 21 | pACR4>>H2B::YFP (Gifford et al., 2003) |

REFERENCES

Alonso J. M., A. N. Stepanova, T. J. Leisse, C. J. Kim, H. Chen, P. Shinn, D. K. Stevenson, J. Zimmerman, P. Barajas, R. Cheuk, C. Gadrinab, C. Heller, A. Jeske, E. Koesema, C. C. Meyers, H. Parker, L. Prednis, Y. Ansari, N. Choy, H. Deen, M. Geralt, N. Hazari, E. Hom, M. Karnes, C. Mulholland, R. Ndubaku, I. Schmidt, P. Guzman, L. Aguilar-Henonin, M. Schmid, D. Weigel, D. E. Carter, T. Marchand, E. Risseeuw, D. Brogden, A. Zeko, W. L. Crosby, C. C. Berry, and J. R. Ecker (2003). Genome-wide insertional mutagenesis of *Arabidopsis thaliana*. *Science* 301:653-657.

Altschul Stephen F., Thomas L. Madden, Alejandro A. Schäffer, Jinghui Zhang, Zheng Zhang, Webb Miller, and David J. Lipman (1997). Gapped BLAST and PSI-BLAST: a new generation of protein database search programs. *Nucleic Acids Res.* 25:3389-3402.

Becker J. D., L. C. Boavida, J. Carneiro, M. Haury, and J. A. Feijo (2003). Transcriptional profiling of *Arabidopsis* tissues reveals the unique characteristics of the pollen transcriptome. *Plant Physiol.* 133:713-725.

Birnbaum K., D. E. Shasha, J. Y. Wang, J. W. Jung, G. M. Lambert, D. W. Galbraith, and P. N. Benfey (2003). A gene expression map of the *Arabidopsis* root. *Science* 302:1956-1960.

Birnbaum K., J. W. Jung, J. Y. Wang, G. M. Lambert, J. A. Hirst, D. W. Galbraith, and P. N. Benfey (2005). Cell type-specific expression profiling in plants via cell sorting of protoplasts from fluorescent reporter lines. *Nat. Methods* 2(8):615-619.

Boerjan W., M.-T. Cervera, M. Delarue, T. Beeckman, W. Dewitte, C. Bellini, M. Caboche, H. Van Onckelen, M. Van Montagu, and D. Inzé (1995). Superroot, a recessive mutation in *Arabidopsis*, confers auxin overproduction. *Plant Cell* 7:1405-1419.

Boudolf V., K. Vlieghe, G. T. Beemster, Z. Magyar, J. A. Torres Acosta, S. Maes, E. Van Der Schueren, D. Inze, and L. De Veylder (2004). The plant-specific cyclin-dependent kinase CDKB1;1 and transcription factor E2Fa-Dpa control the balance of mitotically dividing and endoreduplicating cells in *Arabidopsis*. *Plant Cell* 16:2683-2692.

Brady S. M., S. F. Sarkar, D. Bonetta, and P. McCourt (2003). The ABSCISIC ACID INSENSITIVE 3 (ABI3) gene is modulated by farnesylation and is involved in auxin signaling and lateral root development in *Arabidopsis*. *The Plant Journal* 34:67-75.

Carpenter R. and E. S. Coen (1990). Floral homeotic mutations produced by transposon-mutagenesis in *Antirrhinum majus*. *Genes and Development* 4:1483-1493.

Casero P. J., I. Casimiro, L. Rodriguez-Gallardo, G. Martin-Partido, and P. G. Lloret (1993). Lateral root initiation by means of asymmetric transversal divisions of the pericycle cells in adventitious roots of *Allium cepa*. *Protoplasma* 176:138-144.

Casimiro I., T. Beeckman, N. Graham, R. Bhalerao, H. Zhang, P. Casero, G. Sandberg and M. J. Bennett (2003). Dissecting *Arabidopsis* lateral root development. *Trends in Plant Science* 8:165-171.

Celenza J. L. Jr., P. L. Grisafi and G. R. Fink (1995). A pathway for lateral root formation in *Arabidopsis thaliana*. *Genes Develop.* 9:2131-2142.

Chu T. M., B. Weir, and R. Wolfinger (2002). A systematic statistical linear modeling approach to oligonucleotide array experiments. *Math. Biosci.* 176:35-51.

Chu T. M., B. W. Weir, and R. D. Wolfinger (2004). Comparison of Li-Wong and log linear mixed models for the statistical analysis of oligonucleotide arrays. *Bioinformatics* 20:500-506.

De Veylder L., T. Beeckman, G. T. Beemster, J. de Almeida Engler, S. Ormenese, S. Maes, M. Naudts, E. Van der Schueren, A. Jacqmard, G. Engler, and D. Inze (2002). Control of proliferation, endoreduplication and differentiation by the *Arabidopsis* E2Fa-Dpa transcription factor. *EMBO J.* 15:1360-1368.

Dewitte W. and J. A. Murray (2003). The plant cell cycle. *Ann. Rev. of Plant Biology* 54:235-264.

Dolan L., K. Janmaat, V. Willemsen, P. Linstead, S. Poethig, K. Roberts, and B. Scheres (1993). Cellular organisation of the *Arabidopsis thaliana* root. *Development* 119(1):71-84.

Egger B., R. Leemans, T. Loop, L. Kammermeier, Y. Fan, T. Radimerski, M. C. Strahm, U. Certa, and H. Reichert (2002). Gliogenesis in *Drosophila*: genome-wide analysis of downstream genes of glial cells missing in the embryonic nervous system. *Development* 129(14):3295-3309.

Fukaki H., S. Tameda, H. Masuda, and M. Tasaka (2002). Lateral root formation is blocked by a gain-of-function mutation in the SOLITARY-ROOT/IAA14 gene of *Arabidopsis*. *The Plant Journal* 29:153-168.

Hagen, G. and T. Guilfoyle (2002). Auxin-responsive gene expression: genes, promoters and regulatory factors. *Plant Molecular Biology* 49:373-385.

Himanen K., E. Boucheron, S. Vanneste, J. de Almeida Engler, D. Inzé, and T. Beeckman (2002). Auxin-mediated cell cycle activation during early lateral root initiation. *Plant Cell* 14:2339-2351.

Himanen K., M. Vuylsteke, S. Vanneste, S. Vercruysse, E. Boucheron, E., Alard, P., Chriqui, D., Van Montagu, M., Inzé, and T. Beeckman (2004). Auxin-mediated cell cycle activation during early lateral root initiation. *Proc. Nat. Acad. Sci.* 101(14):5146-5151.

Honys D., and D. Twell (2003). Comparative analysis of the *Arabidopsis* pollen transcriptome. *Plant Physiol.* 132(2):640-652.

Honys D., and D. Twell (2004). Transcriptome analysis of haploid male gametophyte development in *Arabidopsis*. *Genome Biol.* 5(11):R85.

Horvitz H. R., and I. Herskowitz (1992). Mechanisms of asymmetric cell division: two Bs or not two Bs, that is the question. *Cell* 68(2):237-255.

Jürgens G., and U. Mayer (1994). "*Arabidopsis*. In A Colour Atlas of Developing Embryos," J. Bard, ed. (London: Wolfe Publishing), pp. 7-21.

King J. J., D. P. Stimart, R. H. Fisher, and A. B. Bleecker (1995). A mutation altering auxin homeostasis and plant morphology in *Arabidopsis*. *Plant Cell* 7:2023-2037.

Larkin J. C., M. D. Marks, J. Nadeau, and F. Sack (1997). Epidermal cell fate and patterning in leaves. *Plant Cell* 9(7):1109-1120.

Leyser O. (2002). Molecular genetics of auxin signaling. *Annu. Rev. Plant Biol.* 53:377-398.

Maes T., M. Van Montagu, and T. Gerats (1999). The inflorescence architecture of Petunia hybrida is modified by the *Arabidopsis thaliana* Ap2 gene. *Developmental Genetics* 25:199-208.

Mansfield S. G., and L. G. Briarty (1991). Early embryogenesis in *Arabidopsis thaliana* II. The developing embryo. *Canadian Journal of Botany* 69:461-476.

McClure B. A. and T. Guilfoyle (1989). Rapid redistribution of auxin-regulated RNAs during gravitropism. *Science* 243:91-93.

Menges M., L. Hennig, W. Gruissem and J. A. Murray (2003). Genome-wide gene expression in an *Arabidopsis* cell suspension. *Plant Mol. Biol.* 53(4):423-442.

Nakazawa M., N. Yabe, T. Ichikawa, Y. Y. Yamamoto, T. Yoshizumi, K. Hasunuma, and M. Matsui (2001). DFL1, an auxin-responsive GH3 gene homologue, negatively regulates shoot cell elongation and lateral root formation, and positively regulates the light response of hypocotyl length. *Plant J.* 25:213-221.

Park J. Y, H. J. Kim, and J. Kim (2002). Mutation in domain II of IAA1 confers diverse auxin-related phenotypes and represses auxin-activated expression of Aux/IAA genes in steroid regulator-inducible system. *The Plant Journal* 32:669-683.

Sabatini S., R. Heidstra, M. Wildwater, and B. Scheres (2003). SCARECROW is involved in positioning the stem cell niche in the *Arabidopsis* root meristem. *Genes and Development* 17:354-358.

Saeed A. I., V. Sharov, J. White, J. Li, W. Liang, N. Bhagabati, J. Braisted, M. Klapa, T. Currier, M. Thiagarajan, A. Sturn, M. Snuffin, A. Rezantsev, D. Popov, A. Ryltsov, E. Kostukovich, I. Borisovsky, Z. Liu, A. Vinsavich, V. Trush, and J. Quackenbush (2003). TM4: a free, open-source system for microarray data management and analysis. *Biotechniques* 34(2):374-378.

Scheres B., and P. N. Benfey (1999). Asymmetric cell division in plants. *Annu. Rev. Plant Physiol. Plant Mol. Biol.* 50:505-537.

Staswick P. E., I. Tiryaki, and M. L. Rowe (2002). Jasmonate response locus JAR1 and several related *Arabidopsis* genes encode enzymes of the firefly luciferase superfamily that show activity on jasmonic, salicylic, and indole-3-acetic acids in an assay for adenylation. *Plant Cell* 14:1405-1415.

Takase T., M. Nakazawa, A. Ishikawa, M. Kawashima, T. Ichikawa, N. Takahashi, H. Shimada, K. Manambe, and M. Matsui (2004). Ydk1-D, an auxin-responsive GH3 mutant that is involved in hypocotyl and root elongation. *The Plant Journal* 37:471-481.

Tatematsu K., S. Kumagai, H. Muto, A. Sato, M. K. Watahiki, R. M. Harper, E. Liscum, and K. T. Yamamoto (2004). MASSUGU2 encodes Aux/IAA19, an auxin-regulated protein that functions together with the transcriptional activator NPH4/ARF7 to regulate differential growth responses of hypocotyl and formation of lateral roots in *Arabidopsis thaliana*. *Plant Cell* 16:379-393.

Tian Q. and J. W. Reed (1999). Control of auxin-regulated root development by the *Arabidopsis thaliana* SHY2/IAA3 gene. *Development* 126:711-721.

Twell D., S. K. Park, and E. Lalanne (1998). Asymmetric division and cell fate determination in developing pollen. *Trends Plant Sci.* 3:305-310.

van den Berg C., V. Willemsen, W. Hage, P. Weisbeek, and B. Scheres (1995). Cell fate in the *Arabidopsis* root meristem determined by directional signaling. *Nature* 378(6552):62-65.

Vanneste S., B. De Rybel, G. T. Beemster, K. Ljung, I. De Smet, G. Van Isterdael, M. Naudts, R. Iida, W. Gruissem, M. Tasaka, D. Inze, H. Fukaki, and T. Beeckman (2005). Cell cycle progression in the pericycle is not sufficient for SOLITARY ROOT/IAA14-mediated lateral root initiation in *Arabidopsis thaliana*. *Plant Cell* 17:3035-3050.

Wilmoth J. C., S. Wang, S. B. Tiwari, A. D. Joshi, G. Hagen, T. J. Guilfoyle, J. M. Alonso, J. R. Ecker, and J. W. Reed (2005). NPH4/ARF7 and ARF19 promote leaf expansion and auxin-induced lateral root formation. *Plant J.* 43(1):118-130.

Yang, M. and F. D. Sack (1995). The too many mouths and four lips mutations affect stomatal production in *Arabidopsis*. *Plant Cell* 7:2227-2239.

Yang X., S. Lee, J. H. So, S. Dharmasiri, N. Dharmasiri, L. Ge, C. Jensen, R. Hangarter, L. Hobbie, and M. Estelle (2004). The IAA1 protein is encoded by AXR5 and is a substrate of SCFTIR1. *Plant J.* 40:772-782.

What is claimed is:

1. A method of inducing early lateral root initiation, the method comprising:
   introducing into a plant or plant cell a nucleic acid molecule encoding the protein of SEQ ID NO: 2, wherein the nucleic acid molecule is operably linked to a heterologous promoter; and
   selecting a plant or plant cell for early lateral root initiation relative to a corresponding wild-type plant or plant cell.

2. The method according to claim 1, wherein the nucleic acid molecule encodes a transcription factor.

3. A method of inducing lateral root formation, the method comprising:
   introducing into a plant or plant cell an expression construct for inducing asymmetric cell division comprising a nucleic acid molecule encoding a protein involved in asymmetric cell division comprising the protein of SEQ ID NO: 2, wherein the nucleic acid molecule is operably linked to a heterologous promoter; and
   selecting a plant or plant cell for early lateral root formation relative to a corresponding wild-type plant or plant cell.

4. A method for production of a plant having early lateral root initiation, the method comprising:
   introducing into a plant or plant cell a nucleic acid molecule encoding the protein of SEQ ID NO: 2, wherein the nucleic acid molecule is operably linked to a heterologous promoter; and
   selecting a plant for early lateral root initiation relative to a corresponding wild-type plant.

\* \* \* \* \*

SEQUENCE LISTING

```
<160> NUMBER OF SEQ ID NOS: 34

<210> SEQ ID NO 1
<211> LENGTH: 326
<212> TYPE: PRT
<213> ORGANISM: Arabidopsis thaliana
<220> FEATURE:
<221> NAME/KEY: MISC_FEATURE
<223> OTHER INFORMATION: At2g33720

<400> SEQUENCE: 1
```

```
Met Lys Met Pro Pro Phe Ser Ala Ser Lys Thr Gln Tyr Leu Phe
1               5                   10                  15

His Asp Glu Ser Ser Glu Asn Ser Lys Lys Ser Leu Val Ser Thr Thr
            20                  25                  30

Leu Ser Leu Ser Ser Cys Glu Asn Pro Asn Lys Arg Lys Met Asn Ser
                35                  40                  45

Asp Glu Val Leu Asn Ile Ser Cys Ile Pro Arg Asp Tyr Lys Leu Thr
50                      55                  60

Gln Val Glu Arg Lys Ile Ala Arg Met Arg Asn Leu Ser Tyr Gln Glu
65                  70                  75                  80

Lys Ala Glu Asp Glu Trp Tyr Gly Val Ser Thr Glu Leu Thr Leu Phe
                85                  90                  95

Lys Asp Pro Trp Ile Ile Lys Lys Val Phe His Phe Ala Ser Val Leu
                100                 105                 110

Asp Met Ala Pro Asn Ser Val Ser Asn Thr His Cys Leu Leu Asp Thr
            115                 120                 125

Glu Ser Pro Glu Asn Ala Glu Glu Ser Leu Val Ser Leu Asp Leu Cys
130                 135                 140

Phe Tyr Asp Lys Thr Trp Pro His Asp Pro Asn Val Ala Tyr Asn Lys
145                 150                 155                 160

Pro Thr Ser Glu Glu Ala Ile Asn Leu Ala Trp Met Arg Thr Met Ser
                165                 170                 175

Lys Arg Ala Arg Lys Glu Glu Lys Tyr Tyr Val Ser Thr Glu Leu
                180                 185                 190

Thr Leu Leu Thr Val Ala Asp Pro Trp Thr Leu Lys Met Ala Met Thr
            195                 200                 205

Lys Ser Ser Ile Gly Asn Leu Tyr Arg Leu Val Leu Lys Ala Ser Phe
210                 215                 220

Val Asp Ile His Ile Leu Arg Tyr Leu Pro Leu Asp Asp Gln Met Met
225                 230                 235                 240

Val Lys Glu Asp Ser Gly Leu Ala Val Glu Val Tyr Asp His Asp Thr
                245                 250                 255

Asp Ser Val His Asn Leu Ala Leu Lys Lys Trp Ala Lys Ser Ser Ser
            260                 265                 270

Phe Val Leu Val Ser Gly Trp Arg Lys Cys Phe Val Asp Arg Arg Gly
            275                 280                 285

Leu Gln Val Gly Asp Val Ile Gly Met Tyr Trp Asp Arg Ser Glu Ser
            290                 295                 300

Lys Leu His Phe Cys Val Leu Ser Arg Ser Glu Thr Met Asp Ser Ala
305                 310                 315                 320

Pro Leu Pro Pro Ser Pro
                325

<210> SEQ ID NO 2
<211> LENGTH: 354
<212> TYPE: PRT
<213> ORGANISM: Arabidopsis thaliana
<220> FEATURE:
<221> NAME/KEY: MISC_FEATURE
<223> OTHER INFORMATION: At5g53290

<400> SEQUENCE: 2

Met Asp Glu Tyr Ile Asp Phe Arg Pro Leu Lys Tyr Thr Glu His Lys
1               5                   10                  15

Thr Ser Met Thr Lys Tyr Thr Lys Lys Ser Ser Glu Lys Leu Ser Gly
```

```
            20                  25                  30
Gly Lys Ser Leu Lys Lys Val Ser Ile Cys Tyr Thr Asp Pro Asp Ala
             35                  40                  45

Thr Asp Ser Ser Ser Asp Glu Asp Glu Glu Asp Phe Leu Phe Pro Arg
     50                  55                  60

Arg Arg Val Lys Arg Phe Val Asn Glu Ile Thr Val Glu Pro Ser Cys
 65                  70                  75                  80

Asn Asn Val Val Thr Gly Val Ser Met Lys Asp Arg Lys Arg Leu Ser
                 85                  90                  95

Ser Ser Ser Asp Glu Thr Gln Ser Pro Ala Ser Ser Arg Gln Arg Pro
            100                 105                 110

Asn Asn Lys Val Ser Val Ser Gly Gln Ile Lys Lys Phe Arg Gly Val
            115                 120                 125

Arg Gln Arg Pro Trp Gly Lys Trp Ala Ala Glu Ile Arg Asp Pro Glu
        130                 135                 140

Gln Arg Arg Arg Ile Trp Leu Gly Thr Phe Glu Thr Ala Glu Glu Ala
145                 150                 155                 160

Ala Val Val Tyr Asp Asn Ala Ala Ile Arg Leu Arg Gly Pro Asp Ala
                165                 170                 175

Leu Thr Asn Phe Ser Ile Pro Pro Gln Glu Glu Glu Glu Glu Glu Glu
            180                 185                 190

Pro Glu Pro Val Ile Glu Glu Lys Pro Val Ile Met Thr Thr Pro Thr
        195                 200                 205

Pro Thr Thr Ser Ser Ser Glu Ser Thr Glu Glu Asp Leu Gln His Leu
    210                 215                 220

Ser Ser Pro Thr Ser Val Leu Asn His Arg Ser Glu Glu Ile Gln Gln
225                 230                 235                 240

Val Gln Gln Pro Phe Lys Ser Ala Lys Pro Glu Pro Gly Val Ser Asn
                245                 250                 255

Ala Pro Trp Trp His Thr Gly Phe Asn Thr Gly Leu Gly Glu Ser Asp
            260                 265                 270

Asp Ser Phe Pro Leu Asp Thr Pro Phe Leu Asp Asn Tyr Phe Asn Glu
        275                 280                 285

Ser Pro Pro Glu Met Ser Ile Phe Asp Gln Pro Met Asp Gln Ile Phe
    290                 295                 300

Cys Glu Asn Asp Asp Ile Phe Asn Asp Met Leu Phe Leu Gly Gly Glu
305                 310                 315                 320

Thr Met Asn Ile Glu Asp Glu Leu Thr Ser Ser Ile Lys Asp Met
                325                 330                 335

Gly Ser Thr Phe Ser Asp Phe Asp Asp Ser Leu Ile Ser Asp Leu Leu
            340                 345                 350

Val Ala

<210> SEQ ID NO 3
<211> LENGTH: 343
<212> TYPE: PRT
<213> ORGANISM: Arabidopsis thaliana
<220> FEATURE:
<221> NAME/KEY: MISC_FEATURE
<223> OTHER INFORMATION: At4g23750

<400> SEQUENCE: 3

Met Glu Ala Glu Lys Lys Met Val Leu Pro Arg Ile Lys Phe Thr Glu
 1               5                  10                  15

His Lys Thr Asn Thr Thr Thr Ile Val Ser Glu Leu Thr Asn Thr His
```

```
                 20                  25                  30

Gln Thr Arg Ile Leu Arg Ile Ser Val Thr Asp Pro Asp Ala Thr Asp
                     35                  40                  45

Ser Ser Ser Asp Asp Glu Glu Glu His Gln Arg Phe Val Ser Lys
         50                  55                  60

Arg Arg Arg Val Lys Lys Phe Val Asn Glu Val Tyr Leu Asp Ser Gly
         65                  70                  75                  80

Ala Val Val Thr Gly Ser Cys Gly Gln Met Glu Ser Lys Lys Arg Gln
                         85                  90                  95

Lys Arg Ala Val Lys Ser Glu Ser Thr Val Ser Pro Val Val Ser Ala
                    100                 105                 110

Thr Thr Thr Thr Thr Gly Glu Lys Lys Phe Arg Gly Val Arg Gln Arg
                    115                 120                 125

Pro Trp Gly Lys Trp Ala Ala Glu Ile Arg Asp Pro Leu Lys Arg Val
            130                 135                 140

Arg Leu Trp Leu Gly Thr Tyr Asn Thr Ala Glu Glu Ala Ala Met Val
        145                 150                 155                 160

Tyr Asp Asn Ala Ala Ile Gln Leu Arg Gly Pro Asp Ala Leu Thr Asn
                        165                 170                 175

Phe Ser Val Thr Pro Thr Thr Ala Thr Glu Lys Lys Ala Pro Pro Pro
                    180                 185                 190

Ser Pro Val Lys Lys Lys Lys Lys Asn Asn Lys Ser Lys Lys Ser
                    195                 200                 205

Val Thr Ala Ser Ser Ser Ile Ser Arg Ser Ser Asn Asp Cys Leu
            210                 215                 220

Cys Ser Pro Val Ser Val Leu Arg Ser Pro Phe Ala Val Asp Glu Phe
        225                 230                 235                 240

Ser Gly Ile Ser Ser Ser Pro Val Ala Ala Val Val Lys Glu Glu
                        245                 250                 255

Pro Ser Met Thr Thr Val Ser Glu Thr Phe Ser Asp Phe Ser Ala Pro
                    260                 265                 270

Leu Phe Ser Asp Asp Asp Val Phe Asp Phe Arg Ser Ser Val Val Pro
                    275                 280                 285

Asp Tyr Leu Gly Gly Asp Leu Phe Gly Glu Asp Leu Phe Thr Ala Asp
            290                 295                 300

Met Cys Thr Asp Met Asn Phe Gly Phe Asp Phe Gly Ser Gly Leu Ser
        305                 310                 315                 320

Ser Trp His Met Glu Asp His Phe Gln Asp Ile Gly Asp Leu Phe Gly
                        325                 330                 335

Ser Asp Pro Leu Leu Ala Val
                    340

<210> SEQ ID NO 4
<211> LENGTH: 348
<212> TYPE: PRT
<213> ORGANISM: Arabidopsis thaliana
<220> FEATURE:
<221> NAME/KEY: MISC_FEATURE
<223> OTHER INFORMATION: At5g18560

<400> SEQUENCE: 4

Met Ser Thr Ser Lys Thr Leu Asp His Asn Lys Pro Phe Glu Thr Ser
        1               5                   10                  15

Gln Thr Gln Met Gly Phe Ala Leu Ile His Gln Asn Thr Ser Ala Asn
                        20                  25                  30
```

Thr Thr Thr Thr Thr Thr Thr Gly Glu Arg Arg Gly Arg Ser Lys
        35                  40                  45

Gln Ala Glu Pro Gly Arg Phe Leu Gly Val Arg Arg Pro Trp Gly
 50                  55                  60

Arg Tyr Ala Ala Glu Ile Arg Asp Pro Thr Thr Lys Glu Arg His Trp
 65                  70                  75                  80

Leu Gly Thr Phe Asp Thr Ala His Glu Ala Leu Ala Tyr Asp Arg
                 85                  90                  95

Ala Ala Leu Ser Met Arg Gly Thr Gln Ala Arg Thr Asn Phe Val Tyr
                100                 105                 110

Thr Pro Thr Asp Val His Thr Ile Leu Thr Asn Pro Asn Leu His Ser
                115                 120                 125

Leu Ile Val Ser Pro Tyr Asn Asn Asn Gln Ser Phe Leu Pro Asn Ser
130                 135                 140

Ser Pro Gln Phe Val Ile Asp His His Pro His Tyr Gln Asn Tyr His
145                 150                 155                 160

Gln Pro Gln Gln Pro Lys His Thr Leu Pro Gln Thr Val Leu Pro Ala
                165                 170                 175

Ala Ser Phe Lys Thr Pro Val Arg His Gln Ser Val Asp Ile Gln Ala
                180                 185                 190

Phe Gly Asn Ser Pro Gln Asn Ser Ser Asn Gly Ser Leu Ser Ser
                195                 200                 205

Ser Leu Asp Glu Glu Asn Asn Phe Phe Phe Ser Leu Thr Ser Glu Glu
        210                 215                 220

His Asn Lys Ser Asn Asn Asn Ser Gly Tyr Leu Asp Cys Ile Val Pro
225                 230                 235                 240

Asn His Cys Leu Lys Pro Pro Glu Ala Thr Thr Thr Gln Asn Gln
                245                 250                 255

Ala Gly Ala Ser Phe Thr Thr Pro Val Ala Ser Lys Ala Ser Glu Pro
                260                 265                 270

Tyr Gly Gly Phe Ser Asn Ser Tyr Phe Glu Asp Gly Glu Met Met Met
                275                 280                 285

Met Asn His His Glu Phe Gly Ser Cys Asp Leu Ser Ala Met Ile Thr
290                 295                 300

Asn Tyr Gly Ala Ala Ala Ser Met Ser Met Glu Asp Tyr Gly Met
305                 310                 315                 320

Met Glu Pro Gln Asp Leu Ser Ser Ser Ile Ala Ala Phe Gly Asp
                325                 330                 335

Val Val Ala Asp Thr Thr Gly Phe Tyr Ser Val Phe
                340                 345

<210> SEQ ID NO 5
<211> LENGTH: 189
<212> TYPE: PRT
<213> ORGANISM: Arabidopsis thaliana
<220> FEATURE:
<221> NAME/KEY: MISC_FEATURE
<223> OTHER INFORMATION: At1g28360

<400> SEQUENCE: 5

Met Ala Ser Thr Thr Cys Ala Arg Glu Val His Tyr Arg Gly Val Arg
1               5                   10                  15

Lys Arg Pro Trp Gly Arg Tyr Ala Ala Glu Ile Arg Asp Pro Trp Lys
                20                  25                  30

Lys Thr Arg Val Trp Leu Gly Thr Phe Asp Thr Pro Glu Glu Ala Ala
                35                  40                  45

```
Leu Ala Tyr Asp Gly Ala Ala Arg Phe Leu Arg Gly Ile Lys Ala Lys
        50                  55                  60

Thr Asn Phe Pro Ser Pro Leu Ser Leu Asp Leu Asn His Leu Pro Ser
 65                  70                  75                  80

Ala Pro Ser Ala Ala Thr Ala Ala Asn Asn Gln Pro His Gln His
                85                  90                  95

Gln Gln Leu Trp Phe Ala Ala Pro Pro Val Pro Pro Ser Ser Asp
            100                 105                 110

His His His Gln His His Arg Ile Phe Leu Arg Thr Gly Val Leu Asn
            115                 120                 125

Asp Lys Thr Ser Asp Tyr Ser Ser Thr Glu Ala Pro Leu Tyr Phe Thr
        130                 135                 140

Ser Ser Pro Asn Thr Ala Thr Ser Ser Pro Gly Tyr Gln Val Val Gly
145                 150                 155                 160

Phe Pro Met Met Asn Ser Ser Pro Ser Pro Val Thr Val Arg Arg Gly
                165                 170                 175

Leu Ala Ile Asp Leu Asn Glu Pro Pro Pro Leu Trp Leu
                180                 185
```

<210> SEQ ID NO 6
<211> LENGTH: 566
<212> TYPE: PRT
<213> ORGANISM: Arabidopsis thaliana
<220> FEATURE:
<221> NAME/KEY: MISC_FEATURE
<223> OTHER INFORMATION: At5g10510

<400> SEQUENCE: 6

```
Met Glu Met Leu Arg Ser Ser Asp Gln Ser Gln Phe Val Ser Tyr Asp
 1               5                  10                  15

Ala Ser Ser Ala Ala Ser Ser Pro Tyr Leu Leu Asp Asn Phe Tyr
                20                  25                  30

Gly Trp Ser Asn Gln Lys Pro Gln Glu Phe Phe Lys Glu Glu Ala Gln
            35                  40                  45

Leu Ala Ala Ala Ala Ser Met Ala Asp Ser Thr Ile Leu Thr Thr Phe
        50                  55                  60

Val Asp Pro Gln Ser His His Ser Gln Asn His Ile Pro Lys Leu Glu
 65                  70                  75                  80

Asp Phe Leu Gly Asp Ser Ser Ile Val Arg Tyr Ser Asp Asn Ser
                85                  90                  95

Gln Thr Asp Thr Gln Asp Ser Ser Leu Thr Gln Ile Tyr Asp Pro Arg
            100                 105                 110

His His His Asn Gln Thr Gly Phe Tyr Ser Asp His His Asp Phe Lys
            115                 120                 125

Thr Met Ala Gly Phe Gln Ser Ala Phe Ser Thr Asn Ser Gly Ser Glu
        130                 135                 140

Val Asp Asp Ser Ala Ser Ile Gly Arg Thr His Leu Ala Gly Asp Tyr
145                 150                 155                 160

Leu Gly His Val Val Glu Ser Ser Gly Pro Glu Leu Gly Phe His Gly
                165                 170                 175

Gly Ser Thr Gly Ala Leu Ser Leu Gly Val Asn Val Asn Asn Thr
            180                 185                 190

Asn His Arg Asn Asp Asn Asp Asn His Tyr Arg Gly Asn Asn Gly
        195                 200                 205

Glu Arg Ile Asn Asn Asn Asn Asn Asp Asn Glu Lys Thr Asp Ser
```

Glu Lys Glu Lys Ala Val Val Ala Val Glu Thr Ser Asp Cys Ser Asn
225                 230                 235                 240

Lys Lys Ile Ala Asp Thr Phe Gly Gln Arg Thr Ser Ile Tyr Arg Gly
            245                 250                 255

Val Thr Arg His Arg Trp Thr Gly Arg Tyr Glu Ala His Leu Trp Asp
            260                 265                 270

Asn Ser Cys Arg Arg Glu Gly Gln Ala Arg Lys Gly Arg Gln Gly Gly
            275                 280                 285

Tyr Asp Lys Glu Asp Lys Ala Ala Arg Ala Tyr Asp Leu Ala Ala Leu
        290                 295                 300

Lys Tyr Trp Asn Ala Thr Ala Thr Thr Asn Phe Pro Ile Thr Asn Tyr
305                 310                 315                 320

Ser Lys Glu Val Glu Glu Met Lys His Met Thr Lys Gln Glu Phe Ile
            325                 330                 335

Ala Ser Leu Arg Arg Lys Ser Ser Gly Phe Ser Arg Gly Ala Ser Ile
            340                 345                 350

Tyr Arg Gly Val Thr Arg His His Gln Gln Gly Arg Trp Gln Ala Arg
        355                 360                 365

Ile Gly Arg Val Ala Gly Asn Lys Asp Leu Tyr Leu Gly Thr Phe Ala
370                 375                 380

Thr Glu Glu Glu Ala Ala Glu Ala Tyr Asp Ile Ala Ala Ile Lys Phe
385                 390                 395                 400

Arg Gly Ile Asn Ala Val Thr Asn Phe Glu Met Asn Arg Tyr Asp Val
            405                 410                 415

Glu Ala Ile Met Lys Ser Ala Leu Pro Ile Gly Gly Ala Ala Lys Arg
            420                 425                 430

Leu Lys Leu Ser Leu Glu Ala Ala Ser Ser Glu Gln Lys Pro Ile
        435                 440                 445

Leu Gly His His Gln Leu His His Phe Gln Gln Gln Gln Gln Gln
        450                 455                 460

Gln Leu Gln Leu Gln Ser Ser Pro Asn His Ser Ser Ile Asn Phe Ala
465                 470                 475                 480

Leu Cys Pro Asn Ser Ala Val Gln Ser Gln Gln Ile Ile Pro Cys Gly
            485                 490                 495

Ile Pro Phe Glu Ala Ala Ala Leu Tyr His His His Gln Gln Gln Gln
            500                 505                 510

Gln His Gln Gln Gln Gln Gln Gln Asn Phe Phe Gln His Phe Pro
        515                 520                 525

Ala Asn Ala Ala Ser Asp Ser Thr Gly Ser Asn Asn Asn Ser Asn Val
        530                 535                 540

Gln Gly Thr Met Gly Leu Met Ala Pro Asn Pro Ala Glu Phe Phe Leu
545                 550                 555                 560

Trp Pro Asn Gln Ser Tyr
            565

<210> SEQ ID NO 7
<211> LENGTH: 555
<212> TYPE: PRT
<213> ORGANISM: Arabidopsis thaliana
<220> FEATURE:
<221> NAME/KEY: MISC_FEATURE
<223> OTHER INFORMATION: At5g57390

<400> SEQUENCE: 7

```
Met Lys Asn Asn Asn Lys Ser Ser Ser Ser Ser Tyr Asp Ser
 1               5                  10                  15
Ser Leu Ser Pro Ser Ser Ser Ser Ser His Gln Asn Trp Leu Ser
            20              25                  30
Phe Ser Leu Ser Asn Asn Asn Asn Phe Asn Ser Ser Ser Asn Pro
            35              40                  45
Asn Leu Thr Ser Ser Thr Ser Asp His His His Pro His Pro Ser His
 50                  55                  60
Leu Ser Leu Phe Gln Ala Phe Ser Thr Ser Pro Val Glu Arg Gln Asp
 65                  70                  75                  80
Gly Ser Pro Gly Val Ser Pro Ser Asp Ala Thr Ala Val Leu Ser Val
                 85                  90                  95
Tyr Pro Gly Gly Pro Lys Leu Glu Asn Phe Leu Gly Gly Ala Ser
                100                 105                 110
Thr Thr Thr Thr Arg Pro Met Gln Gln Val Gln Ser Leu Gly Gly Val
            115                 120                 125
Val Phe Ser Ser Asp Leu Gln Pro Pro Leu His Pro Pro Ser Ala Ala
    130                 135                 140
Glu Ile Tyr Asp Ser Glu Leu Lys Ser Ile Ala Ala Ser Phe Leu Gly
145                 150                 155                 160
Asn Tyr Ser Gly Gly His Ser Ser Glu Val Ser Ser Val His Lys Gln
                165                 170                 175
Gln Pro Asn Pro Leu Ala Val Ser Glu Ala Ser Pro Thr Pro Lys Lys
            180                 185                 190
Asn Val Glu Ser Phe Gly Gln Arg Thr Ser Ile Tyr Arg Gly Val Thr
    195                 200                 205
Arg His Arg Trp Thr Gly Arg Tyr Glu Ala His Leu Trp Asp Asn Ser
210                 215                 220
Cys Arg Arg Glu Gly Gln Ser Arg Lys Gly Arg Gln Gly Gly Tyr Asp
225                 230                 235                 240
Lys Glu Asp Lys Ala Ala Arg Ala Tyr Asp Leu Ala Ala Leu Lys Tyr
                245                 250                 255
Trp Gly Pro Thr Thr Thr Thr Asn Phe Pro Ile Ser Asn Tyr Glu Ser
                260                 265                 270
Glu Leu Glu Glu Met Lys His Met Thr Arg Gln Glu Phe Val Ala Ser
            275                 280                 285
Leu Arg Arg Lys Ser Ser Gly Phe Ser Arg Gly Ala Ser Met Tyr Arg
    290                 295                 300
Gly Val Thr Arg His His Gln His Gly Arg Trp Gln Ala Arg Ile Gly
305                 310                 315                 320
Arg Val Ala Gly Asn Lys Asp Leu Tyr Leu Gly Thr Phe Ser Thr Gln
                325                 330                 335
Glu Glu Ala Ala Glu Ala Tyr Asp Ile Ala Ala Ile Lys Phe Arg Gly
                340                 345                 350
Leu Asn Ala Val Thr Asn Phe Asp Ile Ser Arg Tyr Asp Val Lys Ser
            355                 360                 365
Ile Ala Ser Cys Asn Leu Pro Val Gly Gly Leu Met Pro Lys Pro Ser
    370                 375                 380
Pro Ala Thr Ala Ala Asp Lys Thr Val Asp Leu Ser Pro Ser Asp
385                 390                 395                 400
Ser Pro Ser Leu Thr Thr Pro Ser Leu Thr Phe Asn Val Ala Thr Pro
                405                 410                 415
Val Asn Asp His Gly Gly Thr Phe Tyr His Thr Gly Ile Pro Ile Lys
```

```
                420                 425                 430
Pro Asp Pro Ala Asp His Tyr Trp Ser Asn Ile Phe Gly Phe Gln Ala
            435                 440                 445

Asn Pro Lys Ala Glu Met Arg Pro Leu Ala Asn Phe Gly Ser Asp Leu
    450                 455                 460

His Asn Pro Ser Pro Gly Tyr Ala Ile Met Pro Val Met Gln Glu Gly
465                 470                 475                 480

Glu Asn Asn Phe Gly Gly Ser Phe Val Gly Ser Asp Gly Tyr Asn Asn
                485                 490                 495

His Ser Ala Ala Ser Asn Pro Val Ser Ala Ile Pro Leu Ser Ser Thr
            500                 505                 510

Thr Thr Met Ser Asn Gly Asn Glu Gly Tyr Gly Gly Asn Ile Asn Trp
        515                 520                 525

Ile Asn Asn Asn Ile Ser Ser Ser Tyr Gln Thr Ala Lys Ser Asn Leu
                530                 535                 540

Ser Val Leu His Thr Pro Val Phe Gly Leu Glu
545                 550                 555

<210> SEQ ID NO 8
<211> LENGTH: 246
<212> TYPE: PRT
<213> ORGANISM: Arabidopsis thaliana
<220> FEATURE:
<221> NAME/KEY: MISC_FEATURE
<223> OTHER INFORMATION: At4g28640

<400> SEQUENCE: 8

Met Glu Gly Gly Ser Ala Ser Gly Ser Ala Ser Ala Leu Ser Asn Asp
1               5                   10                  15

Glu Asn Leu Val Val Ser Cys Glu Asp Ser Ser Ser Pro Ile Gly Asn
            20                  25                  30

Glu Leu Glu Leu Gly Leu Thr Leu Ser Leu Gly Arg Lys Gly Tyr Arg
        35                  40                  45

Asp Cys Arg Val Tyr Ala Asp Asp Ser Ser Ser Ser Ser Ser Ser Ser
    50                  55                  60

Ser Leu Ser Arg Ala Ser Val Ile Ala Gly Ile Lys Arg Thr Ala Asp
65                  70                  75                  80

Ser Met Ala Ala Thr Ser Gly Gln Val Val Gly Trp Pro Pro Ile Arg
                85                  90                  95

Thr Tyr Arg Met Asn Ser Met Val Asn Gln Ala Lys Ala Ser Ala Thr
            100                 105                 110

Glu Asp Pro Asn Leu Glu Ile Ser Gln Ala Val Asn Lys Asn Arg Ser
        115                 120                 125

Asp Ser Thr Lys Met Arg Asn Ser Met Phe Val Lys Val Thr Met Asp
    130                 135                 140

Gly Ile Pro Ile Gly Arg Lys Ile Asp Leu Asn Ala His Lys Cys Tyr
145                 150                 155                 160

Glu Ser Leu Ser Asn Thr Leu Glu Glu Met Phe Leu Lys Pro Lys Leu
                165                 170                 175

Gly Ser Arg Thr Leu Glu Thr Asp Gly His Met Glu Thr Pro Val Lys
            180                 185                 190

Ile Leu Pro Asp Gly Ser Ser Gly Leu Val Leu Thr Tyr Glu Asp Lys
        195                 200                 205

Glu Gly Asp Trp Met Leu Val Gly Asp Val Pro Trp Gly Met Phe Ile
    210                 215                 220
```

Gly Ser Val Arg Arg Leu Arg Ile Met Lys Thr Ser Glu Ala Thr Gly
225                 230                 235                 240

Lys Ala Gln Met Ile Leu
            245

<210> SEQ ID NO 9
<211> LENGTH: 251
<212> TYPE: PRT
<213> ORGANISM: Arabidopsis thaliana
<220> FEATURE:
<221> NAME/KEY: MISC_FEATURE
<223> OTHER INFORMATION: At4g32280

<400> SEQUENCE: 9

Met Glu Leu Asp Leu Gly Leu Ser Leu Ser Pro His Lys Ser Lys
1               5                   10                  15

Leu Gly Phe Asn Phe Asp Leu Asn Lys His Cys Ala Ile Glu Gly Ala
            20                  25                  30

Ala Ser Cys Leu Gly Thr Glu Lys Leu Arg Phe Glu Ala Thr Phe Gly
            35                  40                      45

Leu Gly Asn Val Glu Glu Asn Cys Tyr Met Pro Lys Gln Arg Leu Phe
50                  55                      60

Ala Leu Asn Gly Gln Pro Asn Glu Glu Asp Glu Asp Pro Leu Glu Ser
65                  70                  75                  80

Glu Ser Ser Ile Val Tyr Asp Asp Glu Glu Asn Ser Glu Val Val
                85                  90                  95

Gly Trp Pro Pro Val Lys Thr Cys Met Ile Lys Tyr Gly Ser Tyr His
                100                 105                 110

His Arg His Ile Arg Asn His His His Cys Pro Tyr His His Arg Gly
            115                 120                 125

Arg Arg Ile Thr Ala Met Asn Asn Asn Ile Ser Asn Pro Thr Thr Ala
130                 135                 140

Thr Val Gly Ser Ser Ser Ser Ser Ile Ser Ser Arg Ser Ser Met
145                 150                 155                 160

Tyr Val Lys Val Lys Met Asp Gly Val Ala Ile Ala Arg Lys Val Asp
                165                 170                 175

Ile Lys Leu Phe Asn Ser Tyr Glu Ser Leu Thr Asn Ser Leu Ile Thr
            180                 185                 190

Met Phe Thr Glu Tyr Glu Asp Cys Asp Arg Glu Asp Thr Asn Tyr Thr
        195                 200                 205

Phe Thr Phe Gln Gly Lys Glu Gly Asp Trp Leu Leu Arg Gly Asp Val
210                 215                 220

Thr Trp Lys Ile Phe Ala Glu Ser Val His Arg Ile Ser Ile Ile Arg
225                 230                 235                 240

Asp Arg Pro Cys Ala Tyr Thr Arg Cys Leu Phe
                245                 250

<210> SEQ ID NO 10
<211> LENGTH: 172
<212> TYPE: PRT
<213> ORGANISM: Arabidopsis thaliana
<220> FEATURE:
<221> NAME/KEY: MISC_FEATURE
<223> OTHER INFORMATION: At3g62100

<400> SEQUENCE: 10

Met Gly Arg Gly Arg Ser Ser Ser Ser Ser Ile Glu Ser Ser Cys
1               5                   10                  15

-continued

```
Lys Ser Asn Pro Phe Gly Val Ser Ser Asn Thr Arg Asn Leu Ser
             20                  25                  30

Thr Asp Leu Arg Leu Gly Leu Ser Phe Gly Ser Ser Ser Gly Gln Tyr
         35                  40                  45

Tyr Asn Gly Gly Asp Asn His Glu Tyr Asp Gly Val Gly Ala Ala Glu
 50                  55                  60

Glu Met Met Ile Met Glu Glu Glu Gln Asn Glu Cys Asn Ser Val
 65              70                  75                  80

Gly Ser Phe Tyr Val Lys Val Asn Met Glu Gly Val Pro Ile Gly Arg
                 85                  90                  95

Lys Ile Asp Leu Leu Ser Leu Asn Gly Tyr His Asp Leu Ile Thr Thr
                100                 105                 110

Leu Asp Tyr Met Phe Asn Ala Ser Ile Leu Trp Ala Glu Glu Glu Asp
            115                 120                 125

Met Cys Ser Glu Lys Ser His Val Leu Thr Tyr Ala Asp Lys Glu Gly
130                 135                 140

Asp Trp Met Met Val Gly Asp Val Pro Trp Glu Met Phe Leu Ser Ser
145                 150                 155                 160

Val Arg Arg Leu Lys Ile Ser Arg Ala Tyr His Tyr
                165                 170

<210> SEQ ID NO 11
<211> LENGTH: 186
<212> TYPE: PRT
<213> ORGANISM: Arabidopsis thaliana
<220> FEATURE:
<221> NAME/KEY: MISC_FEATURE
<223> OTHER INFORMATION: At5g43700

<400> SEQUENCE: 11

Met Glu Lys Val Asp Val Tyr Asp Glu Leu Val Asn Leu Lys Ala Thr
  1               5                  10                  15

Glu Leu Arg Leu Gly Leu Pro Gly Thr Glu Glu Thr Val Ser Cys Gly
             20                  25                  30

Lys Ser Asn Lys Arg Val Leu Pro Glu Ala Thr Glu Lys Glu Ile Glu
         35                  40                  45

Ser Thr Gly Lys Thr Glu Thr Ala Ser Pro Pro Lys Ala Gln Ile Val
 50                  55                  60

Gly Trp Pro Pro Val Arg Ser Tyr Arg Lys Asn Asn Val Gln Thr Lys
 65                  70                  75                  80

Lys Ser Glu Ser Glu Gly Gln Gly Asn Tyr Val Lys Val Ser Met Asp
                 85                  90                  95

Gly Ala Pro Tyr Leu Arg Lys Ile Asp Leu Thr Met Tyr Lys Gln Tyr
                100                 105                 110

Pro Glu Leu Met Lys Ser Leu Glu Asn Met Phe Lys Phe Ser Val Gly
            115                 120                 125

Glu Tyr Phe Glu Arg Glu Gly Tyr Lys Gly Ser Asp Phe Val Pro Thr
130                 135                 140

Tyr Glu Asp Lys Asp Gly Asp Trp Met Leu Val Gly Asp Val Pro Trp
145                 150                 155                 160

Glu Met Phe Val Ser Ser Cys Lys Arg Leu Arg Ile Met Lys Gly Ser
                165                 170                 175

Glu Val Lys Gly Leu Gly Cys Gly Gly Leu
            180                 185

<210> SEQ ID NO 12
```

<211> LENGTH: 788
<212> TYPE: PRT
<213> ORGANISM: Arabidopsis thaliana
<220> FEATURE:
<221> NAME/KEY: MISC_FEATURE
<223> OTHER INFORMATION: At5g60450

<400> SEQUENCE: 12

```
Met Glu Phe Asp Leu Asn Thr Glu Ile Ala Glu Val Glu Glu Glu
1               5                   10                  15

Asn Asp Asp Val Gly Val Gly Val Gly Gly Thr Arg Ile Asp Lys
            20                  25                  30

Gly Arg Leu Gly Ile Ser Pro Ser Ser Ser Ser Cys Ser Ser Gly
        35                  40                  45

Ser Ser Ser Ser Ser Ser Thr Gly Ser Ala Ser Ser Ile Tyr Ser
    50                  55                  60

Glu Leu Trp His Ala Cys Ala Gly Pro Leu Thr Cys Leu Pro Lys Lys
65                  70                  75                  80

Gly Asn Val Val Val Tyr Phe Pro Gln Gly His Leu Glu Gln Asp Ala
                85                  90                  95

Met Val Ser Tyr Ser Ser Pro Leu Glu Ile Pro Lys Phe Asp Leu Asn
            100                 105                 110

Pro Gln Ile Val Cys Arg Val Val Asn Val Gln Leu Leu Ala Asn Lys
        115                 120                 125

Asp Thr Asp Glu Val Tyr Thr Gln Val Thr Leu Leu Pro Leu Gln Glu
    130                 135                 140

Phe Ser Met Leu Asn Gly Glu Gly Lys Glu Val Lys Glu Leu Gly Gly
145                 150                 155                 160

Glu Glu Glu Arg Asn Gly Ser Ser Ser Val Lys Arg Thr Pro His Met
                165                 170                 175

Phe Cys Lys Thr Leu Thr Ala Ser Asp Thr Ser Thr His Gly Gly Phe
            180                 185                 190

Ser Val Pro Arg Arg Ala Ala Glu Asp Cys Phe Ala Pro Leu Asp Tyr
        195                 200                 205

Lys Gln Gln Arg Pro Ser Gln Glu Leu Ile Ala Lys Asp Leu His Gly
    210                 215                 220

Val Glu Trp Lys Phe Arg His Ile Tyr Arg Gly Gln Pro Arg Arg His
225                 230                 235                 240

Leu Leu Thr Thr Gly Trp Ser Ile Phe Val Ser Gln Lys Asn Leu Val
                245                 250                 255

Ser Gly Asp Ala Val Leu Phe Leu Arg Asp Glu Gly Gly Glu Leu Arg
            260                 265                 270

Leu Gly Ile Arg Arg Ala Ala Arg Pro Arg Asn Gly Leu Pro Asp Ser
        275                 280                 285

Ile Ile Glu Lys Asn Ser Cys Ser Asn Ile Leu Ser Leu Val Ala Asn
    290                 295                 300

Ala Val Ser Thr Lys Ser Met Phe His Val Phe Tyr Ser Pro Arg Ala
305                 310                 315                 320

Thr His Ala Glu Phe Val Ile Pro Tyr Glu Lys Tyr Ile Thr Ser Ile
                325                 330                 335

Arg Ser Pro Val Cys Ile Gly Thr Arg Phe Arg Met Arg Phe Glu Met
            340                 345                 350

Asp Asp Ser Pro Glu Arg Arg Cys Ala Gly Val Val Thr Gly Val Cys
        355                 360                 365

Asp Leu Asp Pro Tyr Arg Trp Pro Asn Ser Lys Trp Arg Cys Leu Leu
```

```
                370                 375                 380
Val Arg Trp Asp Glu Ser Phe Val Ser Asp His Gln Glu Arg Val Ser
385                 390                 395                 400

Pro Trp Glu Ile Asp Pro Ser Val Ser Leu Pro His Leu Ser Ile Gln
                405                 410                 415

Ser Ser Pro Arg Pro Lys Arg Pro Trp Ala Gly Leu Leu Asp Thr Thr
                420                 425                 430

Pro Pro Gly Asn Pro Ile Thr Lys Arg Gly Gly Phe Leu Asp Phe Glu
                435                 440                 445

Glu Ser Val Arg Pro Ser Lys Val Leu Gln Gly Gln Glu Asn Ile Gly
                450                 455                 460

Ser Ala Ser Pro Ser Gln Gly Phe Asp Val Met Asn Arg Arg Ile Leu
465                 470                 475                 480

Asp Phe Ala Met Gln Ser His Ala Asn Pro Val Leu Val Ser Ser Arg
                485                 490                 495

Val Lys Asp Arg Phe Gly Glu Phe Val Asp Ala Thr Gly Val Asn Pro
                500                 505                 510

Ala Cys Ser Gly Val Met Asp Leu Asp Arg Phe Pro Arg Val Leu Gln
                515                 520                 525

Gly Gln Glu Ile Cys Ser Leu Lys Ser Phe Pro Gln Phe Ala Gly Phe
                530                 535                 540

Ser Pro Ala Ala Pro Asn Pro Phe Ala Tyr Gln Ala Asn Lys Ser
545                 550                 555                 560

Ser Tyr Tyr Pro Leu Ala Leu His Gly Ile Arg Ser Thr His Val Pro
                565                 570                 575

Tyr Gln Asn Pro Tyr Asn Ala Gly Asn Gln Ser Ser Gly Pro Pro Ser
                580                 585                 590

Arg Ala Ile Asn Phe Gly Glu Thr Arg Lys Phe Asp Ala Gln Asn
                595                 600                 605

Glu Gly Gly Leu Pro Asn Asn Val Thr Ala Asp Leu Pro Phe Lys Ile
                610                 615                 620

Asp Met Met Gly Lys Gln Lys Gly Ser Glu Leu Asn Met Asn Ala Ser
625                 630                 635                 640

Ser Gly Cys Lys Leu Phe Gly Phe Ser Leu Pro Val Glu Thr Pro Ala
                645                 650                 655

Ser Lys Pro Gln Ser Ser Ser Arg Ile Cys Thr Lys Val His Lys
                660                 665                 670

Gln Gly Ser Gln Val Gly Arg Ala Ile Asp Leu Ser Arg Leu Asn Gly
                675                 680                 685

Tyr Asp Asp Leu Leu Met Glu Leu Glu Arg Leu Phe Asn Met Glu Gly
                690                 695                 700

Leu Leu Arg Asp Pro Glu Lys Gly Trp Arg Ile Leu Tyr Thr Asp Ser
705                 710                 715                 720

Glu Asn Asp Met Met Val Val Gly Asp Asp Pro Trp His Asp Phe Cys
                725                 730                 735

Asn Val Val Trp Lys Ile His Leu Tyr Thr Lys Glu Val Glu Asn
                740                 745                 750

Ala Asn Asp Asp Asn Lys Ser Cys Leu Glu Gln Ala Ala Leu Met Met
                755                 760                 765

Glu Ala Ser Lys Ser Ser Ser Val Ser Gln Pro Asp Ser Ser Pro Thr
                770                 775                 780

Ile Thr Arg Val
785
```

<210> SEQ ID NO 13
<211> LENGTH: 294
<212> TYPE: PRT
<213> ORGANISM: Arabidopsis thaliana
<220> FEATURE:
<221> NAME/KEY: MISC_FEATURE
<223> OTHER INFORMATION: At4g00940

<400> SEQUENCE: 13

```
Met Asp His His Gln Tyr His His Asp Gln Tyr Gln His Gln Met
1               5                   10                  15

Met Thr Ser Thr Asn Asn Ser Tyr Asn Thr Ile Val Thr Thr Gln
            20                  25                  30

Pro Pro Pro Thr Thr Thr Thr Met Asp Ser Thr Ala Thr Thr Met
            35                  40                  45

Ile Met Asp Asp Glu Lys Lys Leu Met Thr Thr Met Ser Thr Arg Pro
50                  55                  60

Gln Glu Pro Arg Asn Cys Pro Arg Cys Asn Ser Ser Asn Thr Lys Phe
65                  70                  75                  80

Cys Tyr Tyr Asn Asn Tyr Ser Leu Ala Gln Pro Arg Tyr Leu Cys Lys
                    85                  90                  95

Ser Cys Arg Arg Tyr Trp Thr Glu Gly Gly Ser Leu Arg Asn Val Pro
                100                 105                 110

Val Gly Gly Gly Ser Arg Lys Asn Lys Lys Leu Pro Phe Pro Asn Ser
                115                 120                 125

Ser Thr Ser Ser Ser Thr Lys Asn Leu Pro Asp Leu Asn Pro Pro Phe
130                 135                 140

Val Phe Thr Ser Ser Ala Ser Ser Ser Asn Pro Ser Lys Thr His Gln
145                 150                 155                 160

Asn Asn Asn Asp Leu Ser Leu Ser Phe Ser Ser Pro Met Gln Asp Lys
                    165                 170                 175

Arg Ala Gln Gly His Tyr Gly His Phe Ser Glu Gln Val Val Thr Gly
                180                 185                 190

Gly Gln Asn Cys Leu Phe Gln Ala Pro Met Gly Met Ile Gln Phe Arg
                195                 200                 205

Gln Glu Tyr Asp His Glu His Pro Lys Lys Asn Leu Gly Phe Ser Leu
210                 215                 220

Asp Arg Asn Glu Glu Glu Ile Gly Asn His Asp Asn Phe Val Val Asn
225                 230                 235                 240

Glu Glu Gly Ser Lys Met Met Tyr Pro Tyr Gly Asp His Glu Asp Arg
                    245                 250                 255

Gln Gln His His His Val Arg His Asp Asp Gly Asn Lys Lys Arg Glu
                260                 265                 270

Gly Gly Ser Ser Asn Glu Leu Trp Ser Gly Ile Ile Leu Gly Gly Asp
                275                 280                 285

Ser Gly Gly Pro Thr Trp
        290
```

<210> SEQ ID NO 14
<211> LENGTH: 444
<212> TYPE: PRT
<213> ORGANISM: Arabidopsis thaliana
<220> FEATURE:
<221> NAME/KEY: MISC_FEATURE
<223> OTHER INFORMATION: At1g27050

<400> SEQUENCE: 14

```
Met Asp Glu Glu Asp Val Cys Glu Ser Tyr Met Met Arg Glu Ile Thr
1               5                   10                  15
Lys Lys Arg Lys Leu Thr Pro Ile Gln Leu Arg Leu Leu Glu Glu Ser
            20                  25                  30
Phe Glu Glu Lys Arg Leu Glu Pro Asp Arg Lys Leu Trp Leu Ala
        35                  40                  45
Glu Lys Leu Gly Leu Gln Pro Ser Gln Val Ala Val Trp Phe Gln Asn
    50                  55                  60
Arg Arg Ala Arg Tyr Lys Thr Lys Gln Leu Glu His Asp Cys Asp Ser
65                  70                  75                  80
Leu Lys Ala Ser Tyr Ala Lys Leu Lys Thr Asp Trp Asp Ile Leu Phe
                85                  90                  95
Val Gln Asn Gln Thr Leu Lys Ser Lys Val Gln Phe Leu Asn Arg Leu
            100                 105                 110
Thr Ser His Tyr Phe Gln Glu Ser Val Gln Asn Phe Asp Asp Thr Phe
        115                 120                 125
Lys Gln Val Asp Leu Leu Lys Glu Lys Leu Lys Met Gln Glu Asn Leu
    130                 135                 140
Glu Thr Gln Ser Ile Glu Arg Lys Arg Leu Gly Glu Glu Gly Ser Ser
145                 150                 155                 160
Val Lys Ser Asp Asn Thr Gln Tyr Ser Glu Glu Gly Leu Glu Asn
                165                 170                 175
Gln Tyr Ser Phe Pro Glu Leu Ala Val Leu Gly Phe Tyr Tyr Asp Pro
            180                 185                 190
Thr Leu Thr Ala Ser Asn Leu Arg Gln Glu Pro Leu Lys Val Thr Cys
        195                 200                 205
Ala Asp Gln Met Thr Gln Ile Gln Ile Ser Asp Val Thr Glu Pro Ala
    210                 215                 220
Ser Ser Ala His Lys Lys Ile Glu Val Thr Gln Arg Ser Ser Ser Met
225                 230                 235                 240
Ser Arg Lys Arg Asp Lys Pro Tyr Thr Asn Arg His Thr Pro Ala Arg
                245                 250                 255
Ile Ser Lys Arg Arg Pro Trp Ala Pro Ser Ser Glu His Asp
            260                 265                 270
Glu Ile Ile Asp Lys Pro Ile Thr Lys Pro Pro Pro Pro Ala Leu
        275                 280                 285
Val Val Met Gly Leu Pro Ala Asn Cys Ser Val Leu Glu Leu Lys Ser
    290                 295                 300
Arg Phe Glu Ile Tyr Gly Ser Ile Ser Arg Ile Arg Ile His Lys Asp
305                 310                 315                 320
Gly Ile Gly Ser Val Ser Tyr Arg Thr Ala Glu Ser Ala Glu Ala Ala
                325                 330                 335
Ile Ala Gly Ser His Glu Pro Ser Phe Gly Ile Ser Ile Asp Ser Lys
            340                 345                 350
Lys Leu Glu Val Val Trp Ala Thr Asp Pro Leu Val Lys Trp Lys Glu
        355                 360                 365
Gly Val Thr Ala Gly Glu Gly Lys Glu Arg Thr Ser Ser Phe Ser Ser
    370                 375                 380
Lys Leu Leu Arg Pro Val Met Pro Leu Arg Lys His Gly Arg Ser Ser
385                 390                 395                 400
Arg Leu Ala Ser Ala Ile Val Asn Pro Arg Ser Asp Asn Thr Lys Gly
                405                 410                 415
```

```
Ile Ser Gly Asp Gly Gly Ile Ser Ser Pro Ala Thr Thr Ser Glu Val
            420                 425                 430

Lys Gln Arg Asn Ile Val Thr Tyr Asp Asp Ile Val
            435                 440

<210> SEQ ID NO 15
<211> LENGTH: 275
<212> TYPE: PRT
<213> ORGANISM: Arabidopsis thaliana
<220> FEATURE:
<221> NAME/KEY: MISC_FEATURE
<223> OTHER INFORMATION: At2g01430

<400> SEQUENCE: 15

Met Ile Lys Leu Leu Phe Thr Tyr Ile Cys Thr Tyr Thr Tyr Lys Leu
1               5                   10                  15

Tyr Ala Leu Tyr His Met Asp Tyr Ala Cys Val Cys Met Tyr Lys Tyr
            20                  25                  30

Lys Gly Ile Val Thr Leu Gln Val Cys Leu Phe Tyr Ile Lys Leu Arg
        35                  40                  45

Val Phe Leu Ser Asn Phe Thr Phe Ser Ser Ser Ile Leu Ala Leu Lys
    50                  55                  60

Asn Pro Asn Asn Ser Leu Ile Lys Ile Met Ala Ile Leu Pro Glu Asn
65                  70                  75                  80

Ser Ser Asn Leu Asp Leu Thr Ile Ser Val Pro Gly Phe Ser Ser Ser
                85                  90                  95

Pro Leu Ser Asp Glu Gly Ser Gly Gly Gly Arg Asp Gln Leu Arg Leu
            100                 105                 110

Asp Met Asn Arg Leu Pro Ser Ser Glu Asp Gly Asp Glu Glu Phe
            115                 120                 125

Ser His Asp Asp Gly Ser Ala Pro Pro Arg Lys Lys Leu Arg Leu Thr
        130                 135                 140

Arg Glu Gln Ser Arg Leu Leu Glu Asp Ser Phe Arg Gln Asn His Thr
145                 150                 155                 160

Leu Asn Pro Lys Gln Lys Glu Val Leu Ala Lys His Leu Met Leu Arg
                165                 170                 175

Pro Arg Gln Ile Glu Val Trp Phe Gln Asn Arg Arg Ala Arg Ser Lys
            180                 185                 190

Leu Lys Gln Thr Glu Met Glu Cys Glu Tyr Leu Lys Arg Trp Phe Gly
        195                 200                 205

Ser Leu Thr Glu Glu Asn His Arg Leu His Arg Glu Val Glu Glu Leu
    210                 215                 220

Arg Ala Met Lys Val Gly Pro Thr Thr Val Asn Ser Ala Ser Ser Leu
225                 230                 235                 240

Thr Met Cys Pro Arg Cys Glu Arg Val Thr Pro Ala Ala Ser Pro Ser
                245                 250                 255

Arg Ala Val Val Pro Val Pro Ala Lys Lys Thr Phe Pro Pro Gln Glu
            260                 265                 270

Arg Asp Arg
        275

<210> SEQ ID NO 16
<211> LENGTH: 436
<212> TYPE: PRT
<213> ORGANISM: Arabidopsis thaliana
<220> FEATURE:
<221> NAME/KEY: MISC_FEATURE
<223> OTHER INFORMATION: At1g14350
```

<400> SEQUENCE: 16

```
Met Glu Asp Thr Lys Lys Lys Lys Asn Ile Asn Asn Asn Gln
1               5                   10                  15

Asp Ser Lys Lys Lys Glu Arg His Ile Val Thr Trp Ser Gln Glu Glu
            20                  25                  30

Asp Val Ile Leu Arg Glu Gln Ile Thr Leu His Gly Thr Glu Asn Trp
                35                  40                  45

Ala Ile Ile Ala Ser Lys Phe Lys Asp Lys Ser Thr Arg Gln Cys Arg
        50                  55                  60

Arg Arg Trp Tyr Thr Tyr Leu Asn Ser Asp Phe Lys Arg Gly Gly Trp
65                  70                  75                  80

Ser Pro Glu Glu Asp Met Leu Leu Cys Glu Ala Gln Arg Val Phe Gly
                85                  90                  95

Asn Arg Trp Thr Glu Ile Ala Lys Val Val Ser Gly Arg Thr Asp Asn
            100                 105                 110

Ala Val Lys Asn Arg Phe Thr Thr Leu Cys Lys Lys Arg Ala Lys His
                115                 120                 125

Glu Ala Met Thr Lys Asp Ser Asn Ser Asn Thr Lys Arg Met Leu Phe
130                 135                 140

Leu Asp Gly Ile Ser Thr Pro Arg Lys Ser Glu Asn Glu Thr Pro Ile
145                 150                 155                 160

Ala Lys Lys Leu Lys Arg Ser His Ile Leu Asp Leu Thr Glu Ile Ser
                165                 170                 175

Asn Tyr Gly Arg Ala Glu Ala Cys Val Asn Gln Gln Ile Arg Ser Pro
            180                 185                 190

Phe Ser Val Leu Ala Arg Asn Ala Thr Gly Ile Asp Ser Leu Glu Glu
                195                 200                 205

Gln Asn Gln Thr Ser Asn Val Asn Glu Ser Asp Gly Glu Gly Met Phe
        210                 215                 220

Leu Lys Lys Asp Asp Pro Lys Val Thr Ala Leu Met Gln Gln Ala Glu
225                 230                 235                 240

Leu Leu Ser Ser Leu Ala Gln Lys Val Asn Ala Asp Asn Thr Glu Gln
                245                 250                 255

Ser Met Glu Asn Ala Trp Lys Val Leu Gln Asp Phe Leu Asn Lys Gly
            260                 265                 270

Lys Glu Asn Asp Leu Phe Arg Tyr Gly Ile Pro Asp Ile Asp Phe Lys
                275                 280                 285

Ile Glu Glu Phe Lys Asp Leu Ile Glu Asp Leu Arg Ser Gly Tyr Glu
290                 295                 300

Asp Asn Gln Leu Ser Trp Arg Gln Pro Asp Leu His Asp Ser Pro Ala
305                 310                 315                 320

Ser Ser Glu Tyr Ser Ser Gly Ser Thr Ile Met Val Asp Gln Ser Gly
                325                 330                 335

Asp Lys Thr Gln Pro Phe Ser Ala Asp Thr Gln Thr Glu His Lys Gln
                340                 345                 350

Val Gly Glu Glu Leu Leu Val Pro Lys Asn Pro Asp Glu Asn Met Pro
            355                 360                 365

Ile Ser Gly Glu Glu Lys Phe Ser Ser Pro Ile Gln Val Thr Pro Leu
                370                 375                 380

Phe Arg Ser Leu Ala Asp Gly Ile Pro Ser Pro Gln Phe Ser Glu Ser
385                 390                 395                 400

Glu Arg Ser Phe Leu Leu Lys Thr Leu Gly Ile Glu Ser Ser Ser Pro
```

```
                    405                 410                 415
Cys Pro Ser Ala Asn Pro Ser Lys Pro Pro Cys Lys Arg Val Leu
                420                 425                 430

Leu His Ser Leu
        435

<210> SEQ ID NO 17
<211> LENGTH: 352
<212> TYPE: PRT
<213> ORGANISM: Arabidopsis thaliana
<220> FEATURE:
<221> NAME/KEY: MISC_FEATURE
<223> OTHER INFORMATION: At1g18570

<400> SEQUENCE: 17

Met Val Arg Thr Pro Cys Cys Lys Ala Glu Leu Gly Leu Lys Lys Gly
1               5                   10                  15

Ala Trp Thr Pro Glu Glu Asp Gln Lys Leu Leu Ser Tyr Leu Asn Arg
                20                  25                  30

His Gly Glu Gly Gly Trp Arg Thr Leu Pro Glu Lys Ala Gly Leu Lys
            35                  40                  45

Arg Cys Gly Lys Ser Cys Arg Leu Arg Trp Ala Asn Tyr Leu Arg Pro
        50                  55                  60

Asp Ile Lys Arg Gly Glu Phe Thr Asp Glu Glu Arg Ser Ile Ile
65                  70                  75                  80

Ser Leu His Ala Leu His Gly Asn Lys Trp Ser Ala Ile Ala Arg Gly
                85                  90                  95

Leu Pro Gly Arg Thr Asp Asn Glu Ile Lys Asn Tyr Trp Asn Thr His
            100                 105                 110

Ile Lys Lys Arg Leu Ile Lys Lys Gly Ile Asp Pro Val Thr His Lys
        115                 120                 125

Gly Ile Thr Ser Gly Thr Asp Lys Ser Glu Asn Leu Pro Glu Lys Gln
130                 135                 140

Asn Val Asn Leu Thr Thr Ser Asp His Asp Leu Asp Asn Asp Lys Ala
145                 150                 155                 160

Lys Lys Asn Asn Lys Asn Phe Gly Leu Ser Ser Ala Ser Phe Leu Asn
                165                 170                 175

Lys Val Ala Asn Arg Phe Gly Lys Arg Ile Asn Gln Ser Val Leu Ser
            180                 185                 190

Glu Ile Ile Gly Ser Gly Gly Pro Leu Ala Ser Thr Ser His Thr Thr
        195                 200                 205

Asn Thr Thr Thr Ser Val Ser Val Asp Ser Glu Ser Val Lys Ser
210                 215                 220

Thr Ser Ser Ser Phe Ala Pro Thr Ser Asn Leu Leu Cys His Gly Thr
225                 230                 235                 240

Val Ala Thr Thr Pro Val Ser Ser Asn Phe Asp Val Asp Gly Asn Val
                245                 250                 255

Asn Leu Thr Cys Ser Ser Ser Thr Phe Ser Asp Ser Ser Val Asn Asn
            260                 265                 270

Pro Leu Met Tyr Cys Asp Asn Phe Val Gly Asn Asn Asn Val Asp Asp
        275                 280                 285

Glu Asp Thr Ile Gly Phe Ser Thr Phe Leu Asn Asp Glu Asp Phe Met
    290                 295                 300

Met Leu Glu Glu Ser Cys Val Glu Asn Thr Ala Phe Met Lys Glu Leu
305                 310                 315                 320
```

-continued

Thr Arg Phe Leu His Glu Asp Glu Asn Asp Val Val Asp Val Thr Pro
                    325                 330                 335

Val Tyr Glu Arg Gln Asp Leu Phe Asp Glu Ile Asp Asn Tyr Phe Gly
                340                 345                 350

<210> SEQ ID NO 18
<211> LENGTH: 337
<212> TYPE: PRT
<213> ORGANISM: Arabidopsis thaliana
<220> FEATURE:
<221> NAME/KEY: MISC_FEATURE
<223> OTHER INFORMATION: At2g47260

<400> SEQUENCE: 18

Met Glu Phe Thr Asp Phe Ser Lys Thr Ser Phe Tyr Tyr Pro Ser Ser
1               5                   10                  15

Gln Ser Val Trp Asp Phe Gly Asp Leu Ala Ala Ala Glu Arg His Ser
            20                  25                  30

Leu Gly Phe Met Glu Leu Leu Ser Ser Gln Gln His Gln Asp Phe Ala
        35                  40                  45

Thr Val Ser Pro His Ser Phe Leu Leu Gln Thr Ser Gln Pro Gln Thr
    50                  55                  60

Gln Thr Gln Pro Ser Ala Lys Leu Ser Ser Ser Ile Ile Gln Ala Pro
65                  70                  75                  80

Pro Ser Glu Gln Leu Val Thr Ser Lys Val Glu Ser Leu Cys Ser Asp
                85                  90                  95

His Leu Leu Ile Asn Pro Pro Ala Thr Pro Asn Ser Ser Ser Ile Ser
            100                 105                 110

Ser Ala Ser Ser Glu Ala Leu Asn Glu Glu Lys Pro Lys Thr Glu Asp
        115                 120                 125

Asn Glu Glu Glu Gly Gly Glu Asp Gln Gln Glu Lys Ser His Thr Lys
    130                 135                 140

Lys Gln Leu Lys Ala Lys Lys Asn Asn Gln Lys Arg Gln Arg Glu Ala
145                 150                 155                 160

Arg Val Ala Phe Met Thr Lys Ser Glu Val Asp His Leu Glu Asp Gly
                165                 170                 175

Tyr Arg Trp Arg Lys Tyr Gly Gln Lys Ala Val Lys Asn Ser Pro Phe
            180                 185                 190

Pro Arg Ser Tyr Tyr Arg Cys Thr Thr Ala Ser Cys Asn Val Lys Lys
        195                 200                 205

Arg Val Glu Arg Ser Phe Arg Asp Pro Ser Thr Val Val Thr Thr Tyr
    210                 215                 220

Glu Gly Gln His Thr His Ile Ser Pro Leu Thr Ser Arg Pro Ile Ser
225                 230                 235                 240

Thr Gly Gly Phe Phe Gly Ser Ser Gly Ala Ala Ser Ser Leu Gly Asn
                245                 250                 255

Gly Cys Phe Gly Phe Pro Ile Asp Gly Ser Thr Leu Ile Ser Pro Gln
            260                 265                 270

Phe Gln Gln Leu Val Gln Tyr His His Gln Gln Gln Gln Gln Glu Leu
        275                 280                 285

Met Ser Cys Phe Gly Gly Val Asn Glu Tyr Leu Asn Ser His Ala Asn
    290                 295                 300

Glu Tyr Gly Asp Asp Asn Arg Val Lys Lys Ser Arg Val Leu Val Lys
305                 310                 315                 320

Asp Asn Gly Leu Leu Gln Asp Val Val Pro Ser His Met Leu Lys Glu
                325                 330                 335

Glu

```
<210> SEQ ID NO 19
<211> LENGTH: 120
<212> TYPE: PRT
<213> ORGANISM: Arabidopsis thaliana
<220> FEATURE:
<221> NAME/KEY: MISC_FEATURE
<223> OTHER INFORMATION: At5g26930

<400> SEQUENCE: 19
```

| Met | Asp | Pro | Arg | Lys | Leu | Leu | Ser | Cys | Ser | Ser | Tyr | Val | Ser | Val |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Arg | Met | Lys | Glu | Glu | Lys | Gly | Thr | Ile | Arg | Cys | Cys | Ser | Glu | Cys | Lys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Thr | Thr | Lys | Thr | Pro | Met | Trp | Arg | Gly | Gly | Pro | Thr | Gly | Pro | Lys | Ser |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Leu | Cys | Asn | Ala | Cys | Gly | Ile | Arg | His | Arg | Lys | Gln | Arg | Arg | Ser | Glu |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Leu | Leu | Gly | Ile | His | Ile | Ile | Arg | Ser | His | Lys | Ser | Leu | Ala | Ser | Lys |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Lys | Ile | Asn | Leu | Leu | Ser | Ser | His | Gly | Val | Ala | Val | Lys | Lys |
|-----|-----|-----|-----|-----|-----|-----|-----|-----|-----|-----|-----|-----|-----|
|     |     |     |     | 85  |     |     |     |     | 90  |     |     |     | 95  |

| Arg | Arg | Ser | Leu | Lys | Glu | Glu | Glu | Gln | Ala | Ala | Leu | Cys | Leu | Leu | Leu |
|-----|-----|-----|-----|-----|-----|-----|-----|-----|-----|-----|-----|-----|-----|-----|-----|
|     |     |     |     | 100 |     |     |     |     | 105 |     |     |     |     | 110 |     |

| Leu | Ser | Cys | Ser | Ser | Val | Leu | Ala |
|-----|-----|-----|-----|-----|-----|-----|-----|
|     |     |     | 115 |     |     |     | 120 |

```
<210> SEQ ID NO 20
<211> LENGTH: 1090
<212> TYPE: PRT
<213> ORGANISM: Arabidopsis thaliana
<220> FEATURE:
<221> NAME/KEY: MISC_FEATURE
<223> OTHER INFORMATION: At5G63950

<400> SEQUENCE: 20
```

| Met | Ala | Glu | Asn | Thr | Ala | Ser | His | Arg | Arg | Lys | Pro | Arg | Ser | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Arg | His | Tyr | Ser | Ile | Leu | Gln | Asp | Leu | Ser | Ala | Pro | Pro | Arg | Gln |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Pro | Pro | Ser | Ser | Ser | His | Gly | Glu | Asp | Glu | Glu | Thr | Lys | Lys | Ser | Met |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Ile | Lys | Leu | Ala | Gly | Arg | Arg | Arg | Leu | Cys | Lys | Ala | Leu | Pro | Lys | Glu |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Asp | Glu | Ala | Asp | Gly | Tyr | Asp | Asp | Pro | Asp | Leu | Val | Asp | Phe | Tyr | Ser |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Pro | Val | Lys | Gly | Glu | Thr | Ser | Leu | Asp | Ser | Ala | Gly | Ile | Gly | Asn | Lys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Phe | Thr | Ser | Trp | Asp | Glu | Ser | Lys | Glu | Ala | Asn | Thr | Glu | Leu | Ala | Gly |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Glu | Pro | Asn | Phe | Ser | Ile | Ile | Thr | Asp | Phe | Cys | Ser | Pro | Ser | Pro | Gln |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Leu | Lys | Gln | Lys | Glu | Glu | Met | Gln | Gly | Asp | Gly | Arg | Asn | Glu | Ile |
|-----|-----|-----|-----|-----|-----|-----|-----|-----|-----|-----|-----|-----|-----|-----|
|     |     | 130 |     |     |     |     | 135 |     |     |     |     | 140 |     |     |

| Met | Gly | Ile | Leu | Asp | Asp | Leu | Thr | Ser | Lys | Leu | Gly | Thr | Met | Ser | Ile |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

-continued

```
Gln Lys Lys Lys Asp Ser Gln Ser Asn Asp Phe Asp Ala Cys Gly Val
                165                 170                 175
Lys Ser Gln Val Asp Lys Phe Asp Phe Glu Asp Ala Lys Ser Ser Phe
            180                 185                 190
Ser Leu Leu Ser Asp Leu Ser Lys Ser Ser Pro Asp Val Val Thr Thr
        195                 200                 205
Tyr Asn Ala Gly Val Asn Ser Ile Lys Asp Lys Gln Gly Lys Ser Gly
    210                 215                 220
Phe Ala Ile Arg Glu Glu Gln Thr Ser Lys Glu Phe Ser Arg Glu Trp
225                 230                 235                 240
Glu Glu Arg Ile Ser Asn Val Gly Lys Gln Asn Ser Tyr Ser Gly Arg
                245                 250                 255
His Phe Asp Asp Asn Ser Glu Asp Asn Arg Gln Gly Tyr Asn Leu Asp
            260                 265                 270
Arg Gly Lys Ser Gln Cys Lys Glu Val Asp Gln Ser Met Lys Thr Thr
        275                 280                 285
Arg His Ile Glu Val Ser Glu Lys Ile Arg Thr Val Gly Arg Ser Asn
    290                 295                 300
Ala Ala Lys Leu Arg Asp Leu Asp Glu Asp Asp Asp Asp Asp Asp Cys
305                 310                 315                 320
Leu Ile Leu Ser Gly Lys Lys Ala Ala Glu Met Lys Ile Asn Lys Pro
                325                 330                 335
Ala Arg Ser Tyr Asn Ala Lys Arg His Gly Tyr Asp Glu Arg Ser Leu
            340                 345                 350
Glu Asp Glu Gly Ser Ile Thr Leu Thr Gly Leu Asn Leu Ser Tyr Thr
        355                 360                 365
Leu Pro Gly Lys Ile Ala Thr Met Leu Tyr Pro His Gln Arg Glu Gly
    370                 375                 380
Leu Asn Trp Leu Trp Ser Leu His Thr Gln Gly Lys Gly Gly Ile Leu
385                 390                 395                 400
Gly Asp Asp Met Gly Leu Gly Lys Thr Met Gln Ile Cys Ser Phe Leu
                405                 410                 415
Ala Gly Leu Phe His Ser Lys Leu Ile Lys Arg Ala Leu Val Val Ala
            420                 425                 430
Pro Lys Thr Leu Leu Pro His Trp Met Lys Glu Leu Ala Thr Val Gly
        435                 440                 445
Leu Ser Gln Met Thr Arg Glu Tyr Tyr Gly Thr Ser Thr Lys Ala Arg
    450                 455                 460
Glu Tyr Asp Leu His His Ile Leu Gln Gly Lys Gly Ile Leu Leu Thr
465                 470                 475                 480
Thr Tyr Asp Ile Val Arg Asn Asn Thr Lys Ala Leu Gln Gly Asp Asp
                485                 490                 495
His Tyr Thr Asp Glu Asp Asp Glu Asp Gly Asn Lys Trp Asp Tyr Met
            500                 505                 510
Ile Leu Asp Glu Gly His Leu Ile Lys Asn Pro Asn Thr Gln Arg Ala
        515                 520                 525
Lys Ser Leu Leu Glu Ile Pro Ser Ser His Arg Ile Ile Ile Ser Gly
    530                 535                 540
Thr Pro Ile Gln Asn Asn Leu Lys Glu Leu Trp Ala Leu Phe Asn Phe
545                 550                 555                 560
Ser Cys Pro Gly Leu Leu Gly Asp Lys Asn Trp Phe Lys Gln Asn Tyr
                565                 570                 575
Glu His Tyr Ile Leu Arg Gly Thr Asp Lys Asn Ala Thr Asp Arg Glu
```

```
                580             585             590
    Gln Arg Ile Gly Ser Thr Val Ala Lys Asn Leu Arg Glu His Ile Gln
                595             600             605
    Pro Phe Phe Leu Arg Arg Leu Lys Ser Glu Val Phe Gly Asp Asp Gly
                610             615             620
    Ala Thr Ser Lys Leu Ser Lys Lys Asp Glu Ile Val Val Trp Leu Arg
    625             630             635             640
    Leu Thr Ala Cys Gln Arg Gln Leu Tyr Glu Ala Phe Leu Asn Ser Glu
                645             650             655
    Ile Val Leu Ser Ala Phe Asp Gly Ser Pro Leu Ala Ala Leu Thr Ile
                660             665             670
    Leu Lys Lys Ile Cys Asp His Pro Leu Leu Leu Thr Lys Arg Ala Ala
                675             680             685
    Glu Asp Val Leu Glu Gly Met Asp Ser Thr Leu Thr Gln Glu Glu Ala
                690             695             700
    Gly Val Ala Glu Arg Leu Ala Met His Ile Ala Asp Asn Val Asp Thr
    705             710             715             720
    Asp Asp Phe Gln Thr Lys Asn Asp Ser Ile Ser Cys Lys Leu Ser Phe
                725             730             735
    Ile Met Ser Leu Leu Glu Asn Leu Ile Pro Glu Gly His Arg Val Leu
                740             745             750
    Ile Phe Ser Gln Thr Arg Lys Met Leu Asn Leu Ile Gln Asp Ser Leu
                755             760             765
    Thr Ser Asn Gly Tyr Ser Phe Leu Arg Ile Asp Gly Thr Thr Lys Ala
                770             775             780
    Pro Asp Arg Leu Lys Thr Val Glu Glu Phe Gln Glu Gly His Val Ala
    785             790             795             800
    Pro Ile Phe Leu Leu Thr Ser Gln Val Gly Gly Leu Gly Leu Thr Leu
                805             810             815
    Thr Lys Ala Asp Arg Val Ile Val Val Asp Pro Ala Trp Asn Pro Ser
                820             825             830
    Thr Asp Asn Gln Ser Val Asp Arg Ala Tyr Arg Ile Gly Gln Thr Lys
                835             840             845
    Asp Val Ile Val Tyr Arg Leu Met Thr Ser Ala Thr Val Glu Glu Lys
                850             855             860
    Ile Tyr Arg Lys Gln Val Tyr Lys Gly Gly Leu Phe Lys Thr Ala Thr
    865             870             875             880
    Glu His Lys Glu Gln Ile Arg Tyr Phe Ser Gln Gln Asp Leu Arg Glu
                885             890             895
    Leu Phe Ser Leu Pro Lys Gly Gly Phe Asp Val Ser Pro Thr Gln Gln
                900             905             910
    Gln Leu Tyr Glu Glu His Tyr Asn Gln Ile Lys Leu Asp Glu Lys Leu
                915             920             925
    Glu Ser His Val Lys Phe Leu Glu Thr Leu Gly Ile Ala Gly Val Ser
                930             935             940
    His His Ser Leu Leu Phe Ser Lys Thr Ala Pro Ile Gln Ala Ile Gln
    945             950             955             960
    Lys Asp Glu Glu Glu Gln Ile Arg Arg Glu Thr Ala Leu Leu Leu Gly
                965             970             975
    Arg Ala Ser Ala Ser Ile Ser Gln Asp Thr Val Ile Asn Gly Ala Asp
                980             985             990
    Tyr Ala Phe Lys Pro Lys Asp Val Asn Leu Asp Lys Arg Ile Asn Ile
                995             1000            1005
```

-continued

Ser Pro Val Asp Asp Lys Glu Leu Ser Glu Ser Val Ile Lys Ala
    1010                1015                1020

Arg Leu Asn Arg Leu Thr Met Leu Leu Gln Asn Lys Gly Thr Val
    1025                1030                1035

Ser Arg Leu Pro Asp Gly Gly Ala Lys Ile Gln Lys Gln Ile Ala
    1040                1045                1050

Glu Leu Thr Arg Glu Leu Lys Asp Met Lys Ala Ala Glu Arg Ile
    1055                1060                1065

Asn Met Pro Gln Val Ile Asp Leu Glu Glu Asp Ile Ser Arg Lys
    1070                1075                1080

Met Gln Lys Gly Leu Asn Leu
    1085                1090

<210> SEQ ID NO 21
<211> LENGTH: 406
<212> TYPE: PRT
<213> ORGANISM: Arabidopsis thaliana
<220> FEATURE:
<221> NAME/KEY: MISC_FEATURE
<223> OTHER INFORMATION: At5G47440

<400> SEQUENCE: 21

Met Glu Gly Gly Phe Tyr Ser Asp Trp Asn Asp Ser Ser Ser Leu
1               5                   10                  15

Phe Gly Ser Glu Asn Pro Glu His Glu Leu Glu Glu Gly Asn Val Arg
                20                  25                  30

Ser Glu Glu Ile Val Ser Gln Ile Pro Gln Pro Gln Thr Pro Arg Glu
            35                  40                  45

Pro Met Lys Phe Leu Ser Arg Ser Trp Ser Leu Ser Ala Ser Glu Ile
        50                  55                  60

Ser Lys Ala Leu Ala Gln Lys Gln Arg Gln Gln Arg Asp Leu Phe Ser
65                  70                  75                  80

Val Ser Gln Asn Ser Pro Arg Gly Phe Phe Gln Asp Val Ala Ala Asp
                85                  90                  95

Pro Leu Met Ala Glu Asn Ile Met Asn Ser Ala Gly Thr Arg Arg Ser
            100                 105                 110

Gly Arg Leu Ser Lys Trp Phe His His Lys Gln His Thr Asn Pro Ser
        115                 120                 125

Thr Met Arg Ile Pro Arg Lys Lys Asp Lys Ala Arg Val Gln Lys Ala
    130                 135                 140

His Val His Ser Ala Val Ser Ile Ala Ala Leu Ala Ala Gly Leu Ala
145                 150                 155                 160

Ser Val Thr Ser Glu Glu Ser Cys Ser Lys Glu Ser Cys Ser Met Met
                165                 170                 175

Ala Leu Ala Leu Ala Ser Ala Thr Glu Leu Leu Ala Ser His Cys Ile
            180                 185                 190

Asp Met Ala Glu Gln Ala Gly Asp His Thr Cys Val Ala Ser Thr
        195                 200                 205

Val Arg Ser Ser Val Asp Ile His Ser Pro Gly Asp Leu Met Thr Leu
    210                 215                 220

Thr Ala Ala Ala Ala Thr Ala Leu Arg Gly Glu Ala Leu Lys Val
225                 230                 235                 240

Arg Gln Pro Lys Glu Ser Arg Lys Asn Ala Thr Ile Thr Pro Cys Glu
                245                 250                 255

Arg Ser Phe Ser Asp Ser His Trp Pro Gly Glu Asn Cys Gln Phe Arg

```
                260                 265                 270
Leu Glu Glu Pro Asn Leu Pro Leu Glu Gly Glu Leu Val Gln Cys Ala
            275                 280                 285

Arg Asn Gly Leu Gln Arg Asn Lys Arg Val Cys Val Tyr Ile Asn Lys
        290                 295                 300

Lys Ser Gln Val Met Ile Lys Leu Lys Ser Lys His Val Gly Gly Ala
305                 310                 315                 320

Phe Ser Lys Lys Ile Lys Cys Val Val Tyr Gly Val Cys Asp Glu Ile
                325                 330                 335

Ser Ala Trp Pro Cys Arg Lys Glu Arg Glu Asn Ser Glu Glu Val Tyr
            340                 345                 350

Phe Gly Leu Lys Thr Gly Gln Gly Leu Leu Glu Phe Lys Cys Lys Ser
        355                 360                 365

Lys Ile Gln Lys Gln Arg Trp Val Ala Gly Ile Gln Ser Asn Leu Arg
    370                 375                 380

Leu Val Ser Cys Leu Glu Ala Ala Lys Cys Ser Leu Glu Ser Leu Ser
385                 390                 395                 400

Leu Ser Asn Arg Met Arg
                405

<210> SEQ ID NO 22
<211> LENGTH: 250
<212> TYPE: PRT
<213> ORGANISM: Arabidopsis thaliana
<220> FEATURE:
<221> NAME/KEY: MISC_FEATURE
<223> OTHER INFORMATION: At1G69530

<400> SEQUENCE: 22

Met Ala Leu Val Thr Phe Leu Phe Ile Ala Thr Leu Gly Ala Met Thr
1               5                   10                  15

Ser His Val Asn Gly Tyr Ala Gly Gly Gly Trp Val Asn Ala His Ala
            20                  25                  30

Thr Phe Tyr Gly Gly Gly Asp Ala Ser Gly Thr Met Gly Gly Ala Cys
        35                  40                  45

Gly Tyr Gly Asn Leu Tyr Ser Gln Gly Tyr Gly Thr Asn Thr Ala Ala
    50                  55                  60

Leu Ser Thr Ala Leu Phe Asn Asn Gly Leu Ser Cys Gly Ala Cys Phe
65                  70                  75                  80

Glu Ile Arg Cys Gln Asn Asp Gly Lys Trp Cys Leu Pro Gly Ser Ile
                85                  90                  95

Val Val Thr Ala Thr Asn Phe Cys Pro Pro Asn Asn Ala Leu Pro Asn
            100                 105                 110

Asn Ala Gly Gly Trp Cys Asn Pro Pro Gln Gln His Phe Asp Leu Ser
        115                 120                 125

Gln Pro Val Phe Gln Arg Ile Ala Gln Tyr Arg Ala Gly Ile Val Pro
    130                 135                 140

Val Ala Tyr Arg Arg Val Pro Cys Val Arg Arg Gly Gly Ile Arg Phe
145                 150                 155                 160

Thr Ile Asn Gly His Ser Tyr Phe Asn Leu Val Leu Ile Thr Asn Val
                165                 170                 175

Gly Gly Ala Gly Asp Val His Ser Ala Met Val Lys Gly Ser Arg Thr
            180                 185                 190

Gly Trp Gln Ala Met Ser Arg Asn Trp Gly Gln Asn Trp Gln Ser Asn
        195                 200                 205
```

Ser Tyr Leu Asn Gly Gln Ser Leu Ser Phe Lys Val Thr Thr Ser Asp
   210                 215                 220

Gly Gln Thr Ile Val Ser Asn Val Ala Asn Ala Gly Trp Ser Phe
225                 230                 235                 240

Gly Gln Thr Phe Thr Gly Ala Gln Leu Arg
                245                 250

<210> SEQ ID NO 23
<211> LENGTH: 365
<212> TYPE: PRT
<213> ORGANISM: Arabidopsis thaliana
<220> FEATURE:
<221> NAME/KEY: MISC_FEATURE
<223> OTHER INFORMATION: At4G32460

<400> SEQUENCE: 23

Met Lys Glu Met Gly Val Ile Val Leu Leu Leu His Ser Phe Phe
1               5                   10                  15

Tyr Val Ala Phe Cys Phe Asn Asp Gly Leu Pro Asn Gly Asp Phe
                20                  25                  30

Glu Leu Gly Pro Arg His Ser Asp Met Lys Gly Thr Gln Val Ile Asn
            35                  40                  45

Ile Thr Ala Ile Pro Asn Trp Glu Leu Ser Gly Phe Val Glu Tyr Ile
50                  55                  60

Pro Ser Gly His Lys Gln Gly Asp Met Ile Leu Val Val Pro Lys Gly
65                  70                  75                  80

Ala Phe Ala Val Arg Leu Gly Asn Glu Ala Ser Ile Lys Gln Lys Ile
                85                  90                  95

Ser Val Lys Lys Gly Ser Tyr Tyr Ser Ile Thr Phe Ser Ala Ala Arg
                100                 105                 110

Thr Cys Ala Gln Asp Glu Arg Leu Asn Val Ser Val Ala Pro His His
            115                 120                 125

Ala Val Met Pro Ile Gln Thr Val Tyr Ser Ser Ser Gly Trp Asp Leu
        130                 135                 140

Tyr Ser Trp Ala Phe Lys Ala Gln Ser Asp Tyr Ala Asp Ile Val Ile
145                 150                 155                 160

His Asn Pro Gly Val Glu Glu Asp Pro Ala Cys Gly Pro Leu Ile Asp
                165                 170                 175

Gly Val Ala Met Arg Ala Leu Phe Pro Pro Arg Pro Thr Asn Lys Asn
                180                 185                 190

Ile Leu Lys Asn Gly Gly Phe Glu Glu Gly Pro Trp Val Leu Pro Asn
            195                 200                 205

Ile Ser Ser Gly Val Leu Ile Pro Pro Asn Ser Ile Asp Asp His Ser
210                 215                 220

Pro Leu Pro Gly Trp Met Val Glu Ser Leu Lys Ala Val Lys Tyr Ile
225                 230                 235                 240

Asp Ser Asp His Phe Ser Val Pro Gln Gly Arg Arg Ala Val Glu Leu
                245                 250                 255

Val Ala Gly Lys Glu Ser Ala Val Ala Gln Val Val Arg Thr Ile Pro
                260                 265                 270

Gly Lys Thr Tyr Val Leu Ser Phe Ser Val Gly Asp Ala Ser Asn Ala
            275                 280                 285

Cys Ala Gly Ser Met Ile Val Glu Ala Phe Ala Gly Lys Asp Thr Ile
        290                 295                 300

Lys Val Pro Tyr Glu Ser Lys Gly Lys Gly Phe Lys Arg Ser Ser
305                 310                 315                 320

```
Leu Arg Phe Val Ala Val Ser Ser Arg Thr Arg Val Met Phe Tyr Ser
                325                 330                 335

Thr Phe Tyr Ala Met Arg Asn Asp Asp Phe Ser Ser Leu Cys Gly Pro
            340                 345                 350

Val Ile Asp Asp Val Lys Leu Leu Ser Ala Arg Arg Pro
        355                 360                 365

<210> SEQ ID NO 24
<211> LENGTH: 129
<212> TYPE: PRT
<213> ORGANISM: Arabidopsis thaliana
<220> FEATURE:
<221> NAME/KEY: MISC_FEATURE
<223> OTHER INFORMATION: At5G67070

<400> SEQUENCE: 24

Met Ala Ala Ser Ser Leu Asn Leu Leu Ile Leu Ser Leu Leu Thr
1               5                   10                  15

Phe Ile Ser Leu Gln Arg Ser Glu Ser Leu Ser Asp Asn Pro Ser Leu
                20                  25                  30

Thr Leu Leu Pro Asp Gly Phe Asp Trp Pro Ile Ser His Ser Asp Glu
            35                  40                  45

Phe Asp Ile Ile Asp Gly Glu Glu Ser Phe Glu Val Thr Glu Glu Asp
    50                  55                  60

Asp Gly Val Thr Asp Arg Ser Leu Tyr Trp Arg Arg Thr Lys Tyr
65                  70                  75                  80

Tyr Ile Ser Tyr Gly Ala Leu Ser Ala Asn Arg Val Pro Cys Pro Pro
                85                  90                  95

Arg Ser Gly Arg Ser Tyr Tyr Thr His Asn Cys Phe Arg Ala Arg Gly
            100                 105                 110

Pro Val His Pro Tyr Ser Arg Gly Cys Ser Ser Ile Thr Arg Cys Arg
        115                 120                 125

Arg

<210> SEQ ID NO 25
<211> LENGTH: 418
<212> TYPE: PRT
<213> ORGANISM: Arabidopsis thaliana
<220> FEATURE:
<221> NAME/KEY: MISC_FEATURE
<223> OTHER INFORMATION: At4G13210

<400> SEQUENCE: 25

Met Val Val Ala Arg Thr Leu Phe Ser Ile Ser Ala Thr Leu Ile Ile
1               5                   10                  15

Phe Leu Ala Leu Phe Leu His Val Asn Ala Leu Ser Asp Gly Glu Trp
                20                  25                  30

His Glu His Ala Val Lys Asp Pro Glu Glu Ile Ala Ala Met Val Asp
            35                  40                  45

Met Ser Ile Arg Asn Ser Thr Tyr Arg Arg Lys Leu Gly Phe Phe Ser
    50                  55                  60

Ser Cys Ser Thr Gly Asn Pro Ile Asp Asp Cys Trp Arg Cys Asp Lys
65                  70                  75                  80

Lys Trp His Arg Arg Lys Arg Leu Ala Asp Cys Ala Ile Gly Phe
                85                  90                  95

Gly Arg Asn Ala Val Gly Gly Asp Gly Arg Tyr Tyr Ile Val Thr
            100                 105                 110
```

```
Asp Pro Ser Asp His Asp Pro Val Thr Pro Lys Pro Gly Thr Leu Arg
            115                 120                 125

Tyr Ala Val Ile Gln Asp Glu Pro Leu Trp Ile Val Phe Lys Arg Asp
130                 135                 140

Met Val Ile Thr Leu Ser Gln Glu Leu Ile Met Asn Ser Phe Lys Thr
145                 150                 155                 160

Ile Asp Gly Arg Gly Val Asn Val His Ile Ala Gly Gly Ala Cys Leu
                165                 170                 175

Thr Val Gln Tyr Val Thr Asn Ile Ile His Gly Ile Asn Ile His
            180                 185                 190

Asp Cys Lys Arg Thr Gly Asn Ala Met Val Arg Ser Ser Glu Ser His
            195                 200                 205

Tyr Gly Trp Arg Thr Met Ala Asp Gly Asp Gly Ile Ser Ile Phe Gly
            210                 215                 220

Ser Ser His Ile Trp Ile Asp His Asn Ser Leu Ser Ser Cys Ala Asp
225                 230                 235                 240

Gly Leu Ile Asp Ala Ile Met Gly Ser Thr Ala Ile Thr Ile Ser Asn
                245                 250                 255

Asn Tyr Leu Thr His His Asn Glu Ala Ile Leu Leu Gly His Thr Asp
            260                 265                 270

Ser Tyr Thr Arg Asp Lys Met Met Gln Val Thr Ile Ala Tyr Asn His
            275                 280                 285

Phe Gly Glu Gly Leu Ile Gln Arg Met Pro Arg Cys Arg His Gly Tyr
            290                 295                 300

Phe His Val Val Asn Asn Asp Tyr Thr His Trp Glu Met Tyr Ala Ile
305                 310                 315                 320

Gly Gly Ser Ala Asn Pro Thr Ile Asn Ser Gln Gly Asn Arg Phe Leu
                325                 330                 335

Ala Pro Gly Asn Arg Phe Ala Lys Glu Val Thr Lys Arg Val Gly Ala
            340                 345                 350

Gly Lys Gly Glu Trp Asn Asn Trp Asn Trp Arg Ser Gln Gly Asp Leu
            355                 360                 365

Met Leu Asn Gly Ala Tyr Phe Thr Ser Ser Gly Ala Gly Ala Ser Ala
370                 375                 380

Asn Tyr Ala Arg Ala Ser Ser Leu Ala Ala Lys Ser Ser Ser Leu Val
385                 390                 395                 400

Gly Met Leu Thr Ser Ser Ser Gly Ala Leu Lys Cys Arg Ile Gly Thr
                405                 410                 415

Leu Cys

<210> SEQ ID NO 26
<211> LENGTH: 461
<212> TYPE: PRT
<213> ORGANISM: Arabidopsis thaliana
<220> FEATURE:
<221> NAME/KEY: MISC_FEATURE
<223> OTHER INFORMATION: At1G80370

<400> SEQUENCE: 26

Met Gly Lys Glu Asn Ala Val Ser Gly Asn Ser Ile Pro Ile His Gly
1               5                   10                  15

Arg Pro Val Thr Arg Ala Leu Ala Ser Ala Leu Arg Ala Ser Ser Lys
                20                  25                  30

Leu Ile Thr Ser Ser Glu Val Ala Ala Thr Thr Gln Asn Gln Gly Arg
            35                  40                  45
```

```
Val Leu Arg Ala Lys Ser Lys Arg Thr Ala Leu Asp Glu Lys Lys Ala
 50                  55                  60

Asn Ala Pro Lys Lys Arg Ala Val Leu Lys Asp Ile Thr Asn Val Thr
 65                  70                  75                  80

Cys Glu Asn Ser Tyr Thr Ser Cys Phe Ser Val Ala Val Glu Asn Ile
                 85                  90                  95

Lys Gln Ile Lys Lys Gly Arg Gln Ser Ser Ser Ser Lys Val Ala
            100                 105                 110

Ser Ser Ser Ala Thr Ser Gln Val Thr Asp Ala Lys Val Glu Val Val
        115                 120                 125

Ser Asn Ser Ala Gly Ala Ser Leu Ser Val Phe Thr Asp Thr Ser Leu
130                 135                 140

Gly Thr Asn Glu Thr Ser Tyr Ser Ile Ile Ala Lys Pro Ser Ser Arg
145                 150                 155                 160

Ser Pro Pro Arg Pro Phe Gly Thr Val Glu Arg Ser Cys Gly Gly Ala
                165                 170                 175

Ser Ser Pro Lys Phe Val Asp Ile Asp Ser Asp Lys Asp Pro Leu
        180                 185                 190

Leu Cys Ser Leu Tyr Ala Pro Asp Ile Tyr Tyr Asn Leu Arg Val Ala
        195                 200                 205

Glu Leu Lys Arg Arg Pro Phe Pro Asp Phe Met Glu Lys Thr Gln Arg
210                 215                 220

Asp Val Thr Glu Thr Met Arg Gly Ile Leu Val Asp Trp Leu Val Glu
225                 230                 235                 240

Val Ser Glu Glu Tyr Thr Leu Val Pro Asp Thr Leu Tyr Leu Thr Val
                245                 250                 255

Tyr Leu Ile Asp Trp Phe Leu His Gly Asn Tyr Val Glu Arg Gln Arg
            260                 265                 270

Leu Gln Leu Leu Gly Ile Thr Cys Met Leu Ile Ala Ser Lys Tyr Glu
        275                 280                 285

Glu Ile His Ala Pro Arg Ile Glu Glu Phe Cys Phe Ile Thr Asp Asn
        290                 295                 300

Thr Tyr Thr Arg Asp Gln Val Leu Glu Met Glu Ser Gln Val Leu Lys
305                 310                 315                 320

His Phe Ser Phe Gln Ile Tyr Thr Pro Thr Ser Lys Thr Phe Leu Arg
                325                 330                 335

Arg Phe Leu Arg Ala Ala Gln Val Ser Phe Pro Asn Gln Ser Leu Glu
            340                 345                 350

Met Glu Phe Leu Ala Asn Tyr Leu Thr Glu Leu Thr Leu Met Asp Tyr
        355                 360                 365

Pro Phe Leu Lys Phe Leu Pro Ser Ile Ile Ala Ala Ser Ala Val Phe
370                 375                 380

Leu Ala Lys Trp Thr Leu Asn Gln Ser Ser His Pro Trp Asn Pro Thr
385                 390                 395                 400

Leu Glu His Tyr Thr Thr Tyr Lys Ala Ser Asp Leu Lys Ala Ser Val
                405                 410                 415

His Ala Leu Gln Asp Leu Gln Leu Asn Thr Lys Gly Cys Ser Leu Asn
            420                 425                 430

Ser Ile Arg Met Lys Tyr Arg Gln Asp Lys Phe Lys Ser Val Ala Val
        435                 440                 445

Phe Ser Ser Gly Glu Leu Pro Asp Lys Leu Phe Ile Ser
450                 455                 460
```

```
<210> SEQ ID NO 27
<211> LENGTH: 167
<212> TYPE: PRT
<213> ORGANISM: Arabidopsis thaliana
<220> FEATURE:
<221> NAME/KEY: MISC_FEATURE
<223> OTHER INFORMATION: At3G01070

<400> SEQUENCE: 27

Met Ala Arg Val Ala Val Leu Val Ala Gly Ala Val Leu Ala Phe Leu
1               5                   10                  15

Leu Ala Ala Thr Asn Val Thr Ala Lys Arg Trp Thr Val Gly Asp Asn
                20                  25                  30

Lys Phe Trp Asn Pro Asn Ile Asn Tyr Thr Ile Trp Ala Gln Asp Lys
            35                  40                  45

His Phe Tyr Leu Asp Asp Trp Leu Tyr Phe Val Tyr Glu Arg Asn Gln
    50                  55                  60

Tyr Asn Val Ile Glu Val Asn Glu Thr Asn Tyr Ile Ser Cys Asn Pro
65                  70                  75                  80

Asn Asn Pro Ile Ala Asn Trp Ser Arg Gly Ala Gly Arg Asp Leu Val
                85                  90                  95

His Leu Asn Val Thr Arg His Tyr Tyr Leu Ile Ser Gly Asn Gly Gly
            100                 105                 110

Gly Cys Tyr Gly Gly Met Lys Leu Ala Val Leu Val Glu Lys Pro Pro
        115                 120                 125

Pro Pro Pro Ala Ala Ala Pro Asn Lys Asn Ser Ala Arg Arg Thr Phe
    130                 135                 140

Ser Val Ser Gly Phe Ala Tyr Gln Phe Leu Ile Pro Val Ala Val Phe
145                 150                 155                 160

Ala Ala Val Gly Thr Arg Tyr
                165

<210> SEQ ID NO 28
<211> LENGTH: 390
<212> TYPE: PRT
<213> ORGANISM: Arabidopsis thaliana
<220> FEATURE:
<221> NAME/KEY: MISC_FEATURE
<223> OTHER INFORMATION: At1G61580

<400> SEQUENCE: 28

Met Ser His Arg Lys Phe Glu His Pro Arg His Gly Ser Leu Gly Phe
1               5                   10                  15

Leu Pro Arg Lys Arg Ala Ser Arg His Arg Gly Lys Val Lys Ala Phe
                20                  25                  30

Pro Lys Asp Asp Pro Thr Lys Pro Cys Arg Leu Thr Ser Phe Leu Gly
            35                  40                  45

Tyr Lys Ala Gly Met Thr His Ile Val Arg Asp Val Glu Lys Pro Gly
    50                  55                  60

Ser Lys Leu His Lys Lys Glu Thr Cys Glu Ala Val Thr Ile Ile Glu
65                  70                  75                  80

Thr Pro Pro Met Val Val Val Gly Val Val Gly Tyr Val Lys Thr Pro
                85                  90                  95

Arg Gly Leu Arg Ser Leu Cys Thr Val Trp Ala Gln His Leu Ser Glu
            100                 105                 110

Glu Leu Arg Arg Arg Phe Tyr Lys Asn Trp Ala Lys Ser Lys Lys Lys
        115                 120                 125

Ala Phe Thr Arg Tyr Ser Lys Lys His Glu Thr Glu Glu Gly Lys Lys
```

```
                    130                 135                 140
Asp Ile Gln Ser Gln Leu Glu Lys Met Lys Lys Tyr Cys Ser Val Ile
145                 150                 155                 160

Arg Val Leu Ala His Thr Gln Ile Arg Lys Met Lys Gly Leu Lys Gln
                    165                 170                 175

Lys Lys Ala His Leu Asn Glu Ile Gln Ile Asn Gly Gly Asp Ile Ala
                    180                 185                 190

Lys Lys Val Asp Tyr Ala Cys Ser Leu Phe Glu Lys Gln Val Pro Val
                    195                 200                 205

Asp Ala Ile Phe Gln Lys Asp Glu Met Ile Asp Ile Ile Gly Val Thr
                    210                 215                 220

Lys Gly Lys Gly Tyr Glu Gly Val Val Thr Arg Trp Gly Val Thr Arg
225                 230                 235                 240

Leu Pro Arg Lys Thr His Arg Gly Leu Arg Lys Val Ala Cys Ile Gly
                    245                 250                 255

Ala Trp His Pro Ala Arg Val Ser Tyr Thr Val Ala Arg Ala Gly Gln
                    260                 265                 270

Asn Gly Tyr His His Arg Thr Glu Met Asn Lys Lys Val Tyr Arg Val
                    275                 280                 285

Gly Lys Val Gly Gln Glu Thr His Ser Ala Met Thr Glu Tyr Asp Arg
                    290                 295                 300

Thr Glu Lys Asp Ile Thr Pro Met Gly Gly Phe Pro His Tyr Gly Ile
305                 310                 315                 320

Val Lys Glu Asp Tyr Leu Met Ile Lys Gly Cys Cys Val Gly Pro Lys
                    325                 330                 335

Lys Arg Val Val Thr Leu Arg Gln Thr Leu Leu Lys Gln Thr Ser Arg
                    340                 345                 350

Leu Ala Met Glu Glu Ile Lys Leu Lys Phe Ile Asp Ala Ala Ser Asn
                    355                 360                 365

Gly Gly His Gly Arg Phe Gln Thr Ser Gln Glu Lys Ala Lys Phe Tyr
                    370                 375                 380

Gly Arg Thr Ile Lys Ala
385                 390

<210> SEQ ID NO 29
<211> LENGTH: 175
<212> TYPE: PRT
<213> ORGANISM: Arabidopsis thaliana
<220> FEATURE:
<221> NAME/KEY: MISC_FEATURE
<223> OTHER INFORMATION: At2G46990

<400> SEQUENCE: 29

Met Gly Arg Gly Arg Ser Ser Ser Ser Ile Glu Ser Ser
1               5                   10                  15

Lys Ser Asn Pro Phe Gly Ala Ser Ser Thr Arg Asn Leu Ser Thr
                    20                  25                  30

Asp Leu Arg Leu Gly Leu Ser Phe Gly Thr Ser Ser Gly Thr Gln Tyr
                    35                  40                  45

Phe Asn Gly Gly Tyr Gly Tyr Ser Val Ala Ala Pro Ala Val Glu Asp
                    50                  55                  60

Ala Glu Tyr Val Ala Ala Val Glu Glu Glu Glu Asn Glu Cys Asn
65                  70                  75                  80

Ser Val Gly Ser Phe Tyr Val Lys Val Asn Met Glu Gly Val Pro Ile
                    85                  90                  95
```

```
Gly Arg Lys Ile Asp Leu Met Ser Leu Asn Gly Tyr Arg Asp Leu Ile
                100                 105                 110

Arg Thr Leu Asp Phe Met Phe Asn Ala Ser Ile Leu Trp Ala Glu Glu
            115                 120                 125

Glu Asp Met Cys Asn Glu Lys Ser His Val Leu Thr Tyr Ala Asp Lys
        130                 135                 140

Glu Gly Asp Trp Met Met Val Gly Asp Val Pro Trp Glu Met Phe Leu
145                 150                 155                 160

Ser Thr Val Arg Arg Leu Lys Ile Ser Arg Ala Asn Tyr His Tyr
                165                 170                 175

<210> SEQ ID NO 30
<211> LENGTH: 716
<212> TYPE: PRT
<213> ORGANISM: Arabidopsis thaliana
<220> FEATURE:
<221> NAME/KEY: MISC_FEATURE
<223> OTHER INFORMATION: At4G02060

<400> SEQUENCE: 30

Met Lys Asp His Asp Phe Asp Gly Asp Lys Gly Leu Ala Lys Gly Phe
1               5                   10                  15

Leu Glu Asn Phe Ala Asp Ala Asn Gly Arg Ser Lys Tyr Met Glu Ile
                20                  25                  30

Leu Gln Glu Val Ser Asn Arg Lys Ile Arg Ala Ile Gln Val Asp Leu
            35                  40                  45

Asp Asp Leu Phe Asn Tyr Lys Asp Glu Ser Glu Glu Phe Leu Gly Arg
        50                  55                  60

Leu Thr Glu Asn Thr Arg Arg Tyr Val Ser Ile Phe Ser Ala Ala Val
65              70                  75                  80

Asp Glu Leu Leu Pro Glu Pro Thr Glu Ala Phe Pro Asp Asp His
                85                  90                  95

Asp Ile Leu Met Thr Gln Arg Ala Asp Asp Gly Thr Asp Asn Pro Asp
                100                 105                 110

Val Ser Asp Pro His Gln Gln Ile Pro Ser Glu Ile Lys Arg Tyr Tyr
            115                 120                 125

Glu Val Tyr Phe Lys Ala Pro Ser Lys Gly Arg Pro Ser Thr Ile Arg
        130                 135                 140

Glu Val Lys Ala Ser His Ile Gly Gln Leu Val Arg Ile Ser Gly Ile
145                 150                 155                 160

Val Thr Arg Cys Ser Asp Val Lys Pro Leu Met Ala Val Ala Val Tyr
                165                 170                 175

Thr Cys Glu Asp Cys Gly His Glu Ile Tyr Gln Glu Val Thr Ser Arg
                180                 185                 190

Val Phe Met Pro Leu Phe Lys Cys Pro Ser Ser Arg Cys Arg Leu Asn
            195                 200                 205

Ser Lys Ala Gly Asn Pro Ile Leu Gln Leu Arg Ala Ser Lys Phe Leu
        210                 215                 220

Lys Phe Gln Glu Ala Lys Met Gln Glu Leu Ala Glu His Val Pro Lys
225                 230                 235                 240

Gly His Ile Pro Arg Ser Met Thr Val His Leu Arg Gly Glu Leu Thr
                245                 250                 255

Arg Lys Val Ser Pro Gly Asp Val Val Glu Phe Ser Gly Ile Phe Leu
                260                 265                 270

Pro Ile Pro Tyr Thr Gly Phe Lys Ala Leu Arg Ala Gly Leu Val Ala
            275                 280                 285
```

-continued

Asp Thr Tyr Leu Glu Ala Thr Ser Val Thr His Phe Lys Lys Tyr
    290                 295                 300

Glu Glu Tyr Glu Phe Gln Lys Asp Glu Glu Gln Ile Ala Arg Leu
305                 310                 315                 320

Ala Glu Asp Gly Asp Ile Tyr Asn Lys Leu Ser Arg Ser Leu Ala Pro
                325                 330                 335

Glu Ile Tyr Gly His Glu Asp Ile Lys Lys Ala Leu Leu Leu Leu
            340                 345                 350

Val Gly Ala Pro His Arg Gln Leu Lys Asp Gly Met Lys Ile Arg Gly
            355                 360                 365

Asp Val His Ile Cys Leu Met Gly Asp Pro Gly Val Ala Lys Ser Gln
370                 375                 380

Leu Leu Lys His Ile Ile Asn Val Ala Pro Arg Gly Val Tyr Thr Thr
385                 390                 395                 400

Gly Lys Gly Ser Ser Gly Val Gly Leu Thr Ala Ala Val Met Arg Asp
                405                 410                 415

Gln Val Thr Asn Glu Met Val Leu Glu Gly Gly Ala Leu Val Leu Ala
            420                 425                 430

Asp Met Gly Ile Cys Ala Ile Asp Glu Phe Asp Lys Met Asp Glu Ser
            435                 440                 445

Asp Arg Thr Ala Ile His Glu Val Met Glu Gln Gln Thr Val Ser Ile
450                 455                 460

Ala Lys Ala Gly Ile Thr Thr Ser Leu Asn Ala Arg Thr Ala Val Leu
465                 470                 475                 480

Ala Ala Ala Asn Pro Ala Trp Gly Arg Tyr Asp Leu Arg Arg Thr Pro
                485                 490                 495

Ala Glu Asn Ile Asn Leu Pro Pro Ala Leu Leu Ser Arg Phe Asp Leu
            500                 505                 510

Leu Trp Leu Ile Leu Asp Arg Ala Asp Met Asp Ser Asp Leu Glu Leu
            515                 520                 525

Ala Lys His Val Leu His Val His Gln Thr Glu Glu Ser Pro Ala Leu
530                 535                 540

Gly Phe Glu Pro Leu Glu Pro Asn Ile Leu Arg Ala Tyr Ile Ser Ala
545                 550                 555                 560

Ala Arg Arg Leu Ser Pro Tyr Val Pro Ala Glu Leu Glu Glu Tyr Ile
                565                 570                 575

Ala Thr Ala Tyr Ser Ser Ile Arg Gln Glu Glu Ala Lys Ser Asn Thr
            580                 585                 590

Pro His Ser Tyr Thr Thr Val Arg Thr Leu Leu Ser Ile Leu Arg Ile
            595                 600                 605

Ser Ala Ala Leu Ala Arg Leu Arg Phe Ser Gly Ser Val Ala Gln Ser
610                 615                 620

Asp Val Asp Glu Ala Leu Arg Leu Met Gln Met Ser Lys Ile Ser Leu
625                 630                 635                 640

Tyr Ala Asp Asp Arg Gln Lys Ala Gly Leu Asp Ala Ile Ser Asp Thr
                645                 650                 655

Tyr Ser Ile Ile Arg Asp Glu Ala Ala Arg Ser Lys Lys Thr His Val
            660                 665                 670

Ser Tyr Ala Asn Ala Leu Asn Trp Ile Ser Arg Lys Gly Tyr Ser Glu
            675                 680                 685

Ala Gln Leu Lys Glu Cys Leu Glu Glu Tyr Ala Ala Leu Asn Val Trp
690                 695                 700

Gln Ile Asp Pro His Thr Phe Asp Ile Arg Phe Ile
705                 710                 715

<210> SEQ ID NO 31
<211> LENGTH: 351
<212> TYPE: PRT
<213> ORGANISM: Arabidopsis thaliana
<220> FEATURE:
<221> NAME/KEY: MISC_FEATURE
<223> OTHER INFORMATION: At2G33620

<400> SEQUENCE: 31

Met Ser Gly Ser Glu Thr Gly Leu Met Ala Ala Thr Arg Glu Ser Met
1               5                   10                  15

Gln Phe Thr Met Ala Leu His Gln Gln Gln His Ser Gln Ala Gln
            20                  25                  30

Pro Gln Gln Ser Gln Asn Arg Pro Leu Ser Phe Gly Gly Asp Asp Gly
            35                  40                  45

Thr Ala Leu Tyr Lys Gln Pro Met Arg Ser Val Ser Pro Pro Gln Gln
        50                  55                  60

Tyr Gln Pro Asn Ser Ala Gly Glu Asn Ser Val Leu Asn Met Asn Leu
65                  70                  75                  80

Pro Gly Gly Glu Ser Gly Gly Met Thr Gly Thr Gly Ser Glu Pro Val
                85                  90                  95

Lys Lys Arg Arg Gly Arg Pro Arg Lys Tyr Gly Pro Asp Ser Gly Glu
            100                 105                 110

Met Ser Leu Gly Leu Asn Pro Gly Ala Pro Ser Phe Thr Val Ser Gln
        115                 120                 125

Pro Ser Gly Gly Asp Gly Gly Glu Lys Lys Arg Gly Arg Pro Pro
130                 135                 140

Gly Ser Ser Ser Lys Arg Leu Lys Leu Gln Ala Leu Gly Ser Thr Gly
145                 150                 155                 160

Ile Gly Phe Thr Pro His Val Leu Thr Val Leu Ala Gly Glu Asp Val
                165                 170                 175

Ser Ser Lys Ile Met Ala Leu Thr His Asn Gly Pro Arg Ala Val Cys
            180                 185                 190

Val Leu Ser Ala Asn Gly Ala Ile Ser Asn Val Thr Leu Arg Gln Ser
        195                 200                 205

Ala Thr Ser Gly Gly Thr Val Thr Tyr Glu Gly Arg Phe Glu Ile Leu
    210                 215                 220

Ser Leu Ser Gly Ser Phe His Leu Leu Glu Asn Asn Gly Gln Arg Ser
225                 230                 235                 240

Arg Thr Gly Gly Leu Ser Val Ser Leu Ser Ser Pro Asp Gly Asn Val
                245                 250                 255

Leu Gly Gly Ser Val Ala Gly Leu Leu Ile Ala Ala Ser Pro Val Gln
            260                 265                 270

Ile Val Val Gly Ser Phe Leu Pro Asp Gly Glu Lys Glu Pro Lys Gln
        275                 280                 285

His Val Gly Gln Met Gly Leu Ser Ser Pro Val Leu Pro Arg Val Ala
    290                 295                 300

Pro Thr Gln Val Leu Met Thr Pro Ser Pro Gln Ser Arg Gly Thr
305                 310                 315                 320

Met Ser Glu Ser Ser Cys Gly Gly Gly His Gly Ser Pro Ile His Gln
                325                 330                 335

Ser Thr Gly Gly Pro Tyr Asn Asn Thr Ile Asn Met Pro Trp Lys
            340                 345                 350

<210> SEQ ID NO 32
<211> LENGTH: 1492
<212> TYPE: PRT
<213> ORGANISM: Arabidopsis thaliana
<220> FEATURE:
<221> NAME/KEY: MISC_FEATURE
<223> OTHER INFORMATION: At5G67100

<400> SEQUENCE: 32

```
Met Ser Gly Asp Asn Ser Thr Glu Thr Gly Arg Arg Ser Arg Gly
1               5                   10                  15

Ala Glu Ala Ser Ser Arg Lys Asp Thr Leu Glu Arg Leu Lys Ala Ile
            20                  25                  30

Arg Gln Gly Gly Ile Arg Ser Ala Ser Gly Gly Gly Tyr Asp Ile Arg
        35                  40                  45

Leu Gln Lys Pro Ile Phe Asp Thr Val Asp Asp Glu Glu Tyr Asp Ala
    50                  55                  60

Leu Val Ser Arg Arg Glu Glu Ala Arg Gly Phe Val Val Glu Asp
65                  70                  75                  80

Gly Glu Gly Gly Asp Leu Gly Tyr Leu Asp Glu Gly Glu Glu Asp
                85                  90                  95

Trp Ser Lys Pro Ser Gly Pro Glu Ser Thr Asp Glu Ser Asp Asp Gly
            100                 105                 110

Gly Arg Phe Ser Gly Arg Leu Lys Lys Lys Lys Gly Lys Glu Gln
        115                 120                 125

Thr Gln Gln Pro Gln Val Lys Lys Val Asn Pro Ala Leu Lys Ala Ala
130                 135                 140

Ala Thr Ile Thr Gly Glu Gly Arg Leu Ser Ser Met Phe Thr Ser Ser
145                 150                 155                 160

Ser Phe Lys Lys Val Lys Glu Thr Asp Lys Ala Gln Tyr Glu Gly Ile
                165                 170                 175

Leu Asp Glu Ile Ile Ala Gln Val Thr Pro Asp Glu Ser Asp Arg Lys
            180                 185                 190

Lys His Thr Arg Arg Lys Leu Pro Gly Thr Val Pro Val Thr Ile Phe
        195                 200                 205

Lys Asn Lys Lys Leu Phe Ser Val Ala Ser Ser Met Gly Met Lys Glu
    210                 215                 220

Ser Glu Pro Thr Pro Ser Thr Tyr Glu Gly Asp Ser Val Ser Met Asp
225                 230                 235                 240

Asn Glu Leu Met Lys Glu Glu Asp Met Lys Glu Ser Glu Val Ile Pro
                245                 250                 255

Ser Glu Thr Met Glu Leu Leu Gly Ser Asp Ile Val Lys Glu Asp Gly
            260                 265                 270

Ser Asn Lys Ile Arg Lys Thr Glu Val Lys Ser Glu Leu Gly Val Lys
        275                 280                 285

Glu Val Phe Thr Leu Asn Ala Thr Ile Asp Met Lys Glu Lys Asp Ser
    290                 295                 300

Ala Leu Ser Ala Thr Ala Gly Trp Lys Glu Ala Met Gly Lys Val Gly
305                 310                 315                 320

Thr Glu Asn Gly Ala Leu Leu Gly Ser Ser Glu Gly Lys Thr Glu
                325                 330                 335

Phe Asp Leu Asp Ala Asp Gly Ser Leu Arg Phe Phe Ile Leu Asp Ala
            340                 345                 350

Tyr Glu Glu Ala Phe Gly Ala Ser Met Gly Thr Ile Tyr Leu Phe Gly
```

```
            355                 360                 365
Lys Val Lys Met Gly Asp Thr Tyr Lys Ser Cys Cys Val Val Lys
            370                 375                 380

Asn Ile Gln Arg Cys Val Tyr Ala Ile Pro Asn Asp Ser Ile Phe Pro
385                         390                 395                 400

Ser His Glu Leu Ile Met Leu Glu Gln Glu Val Lys Asp Ser Arg Leu
                    405                 410                 415

Ser Pro Glu Ser Phe Arg Gly Lys Leu His Glu Met Ala Ser Lys Leu
                420                 425                 430

Lys Asn Glu Ile Ala Gln Glu Leu Leu Gln Leu Asn Val Ser Asn Phe
            435                 440                 445

Ser Met Ala Pro Val Lys Arg Asn Tyr Ala Phe Glu Arg Pro Asp Val
    450                 455                 460

Pro Ala Gly Glu Gln Tyr Val Leu Lys Ile Asn Tyr Ser Phe Lys Asp
465                 470                 475                 480

Arg Pro Leu Pro Glu Asp Leu Lys Gly Glu Ser Phe Ser Ala Leu Leu
                485                 490                 495

Gly Ser His Thr Ser Ala Leu Glu His Phe Ile Leu Lys Arg Lys Ile
            500                 505                 510

Met Gly Pro Cys Trp Leu Lys Ile Ser Ser Phe Ser Thr Cys Ser Pro
        515                 520                 525

Ser Glu Gly Val Ser Trp Cys Lys Phe Glu Val Thr Val Gln Ser Pro
    530                 535                 540

Lys Asp Ile Thr Ile Leu Val Ser Glu Glu Lys Val Val His Pro Pro
545                 550                 555                 560

Ala Val Val Thr Ala Ile Asn Leu Lys Thr Ile Val Asn Glu Lys Gln
                565                 570                 575

Asn Ile Ser Glu Ile Val Ser Ala Ser Val Leu Cys Phe His Asn Ala
            580                 585                 590

Lys Ile Asp Val Pro Met Pro Ala Pro Glu Arg Lys Arg Ser Gly Ile
        595                 600                 605

Leu Ser His Phe Thr Val Val Arg Asn Pro Glu Gly Thr Gly Tyr Pro
    610                 615                 620

Ile Gly Trp Lys Lys Glu Val Ser Asp Arg Asn Ser Lys Asn Gly Cys
625                 630                 635                 640

Asn Val Leu Ser Ile Glu Asn Ser Glu Arg Ala Leu Leu Asn Arg Leu
                645                 650                 655

Phe Leu Glu Leu Asn Lys Leu Asp Ser Asp Ile Leu Val Gly His Asn
            660                 665                 670

Ile Ser Gly Phe Asp Leu Asp Val Leu Leu Gln Arg Ala Gln Ala Cys
        675                 680                 685

Lys Val Gln Ser Ser Met Trp Ser Lys Ile Gly Arg Leu Lys Arg Ser
    690                 695                 700

Phe Met Pro Lys Leu Lys Gly Asn Ser Asn Tyr Gly Ser Gly Ala Thr
705                 710                 715                 720

Pro Gly Leu Met Ser Cys Ile Ala Gly Arg Leu Leu Cys Asp Thr Asp
                725                 730                 735

Leu Cys Ser Arg Asp Leu Leu Lys Glu Val Ser Tyr Ser Leu Thr Asp
            740                 745                 750

Leu Ser Lys Thr Gln Leu Asn Arg Asp Arg Lys Glu Ile Ala Pro Asn
        755                 760                 765

Asp Ile Pro Lys Met Phe Gln Ser Ser Lys Thr Leu Val Glu Leu Ile
770                 775                 780
```

Glu Cys Gly Glu Thr Asp Ala Trp Leu Ser Met Glu Leu Met Phe His
785                 790                 795                 800

Leu Ser Val Leu Pro Leu Thr Leu Gln Leu Thr Asn Ile Ser Gly Asn
            805                 810                 815

Leu Trp Gly Lys Thr Leu Gln Gly Ala Arg Ala Gln Arg Ile Glu Tyr
            820                 825                 830

Tyr Leu Leu His Thr Phe His Ser Lys Lys Phe Ile Leu Pro Asp Lys
            835                 840                 845

Ile Ser Gln Arg Met Lys Glu Ile Lys Ser Ser Lys Arg Arg Met Asp
850                 855                 860

Tyr Ala Pro Glu Asp Arg Asn Val Asp Glu Leu Asp Ala Asp Leu Thr
865                 870                 875                 880

Leu Glu Asn Asp Pro Ser Lys Gly Ser Lys Thr Lys Lys Gly Pro Ala
            885                 890                 895

Tyr Ala Gly Gly Leu Val Leu Glu Pro Lys Arg Gly Leu Tyr Asp Lys
            900                 905                 910

Tyr Val Leu Leu Leu Asp Phe Asn Ser Leu Tyr Pro Ser Ile Ile Gln
            915                 920                 925

Glu Tyr Asn Ile Cys Phe Thr Thr Ile Pro Arg Ser Glu Asp Gly Val
930                 935                 940

Pro Arg Leu Pro Ser Ser Gln Thr Pro Gly Ile Leu Pro Lys Leu Met
945                 950                 955                 960

Glu His Leu Val Ser Ile Arg Lys Ser Val Lys Leu Lys Met Lys Lys
            965                 970                 975

Glu Thr Gly Leu Lys Tyr Trp Glu Leu Asp Ile Arg Gln Gln Ala Leu
            980                 985                 990

Lys Leu Thr Ala Asn Ser Met Tyr Gly Cys Leu Gly Phe Ser Asn Ser
            995                 1000                1005

Arg Phe Tyr Ala Lys Pro Leu Ala Glu Leu Ile Thr Leu Gln Gly
    1010                1015                1020

Arg Asp Ile Leu Gln Arg Thr Val Asp Leu Val Gln Asn His Leu
    1025                1030                1035

Asn Leu Glu Val Ile Tyr Gly Asp Thr Asp Ser Ile Met Ile His
    1040                1045                1050

Ser Gly Leu Asp Asp Ile Glu Val Lys Ala Ile Lys Ser Lys
    1055                1060                1065

Val Ile Gln Glu Val Asn Lys Lys Tyr Arg Cys Leu Lys Ile Asp
    1070                1075                1080

Cys Asp Gly Ile Tyr Lys Arg Met Leu Leu Leu Arg Lys Lys Lys
    1085                1090                1095

Tyr Ala Ala Val Lys Leu Gln Phe Lys Asp Gly Lys Pro Cys Glu
    1100                1105                1110

Asp Ile Glu Arg Lys Gly Val Asp Met Val Arg Arg Asp Trp Ser
    1115                1120                1125

Leu Leu Ser Lys Glu Ile Gly Asp Leu Cys Leu Ser Lys Ile Leu
    1130                1135                1140

Tyr Gly Gly Ser Cys Glu Asp Val Val Glu Ala Ile His Asn Glu
    1145                1150                1155

Leu Met Lys Ile Lys Glu Glu Met Arg Asn Gly Gln Val Ala Leu
    1160                1165                1170

Glu Lys Tyr Val Ile Thr Lys Thr Leu Thr Lys Pro Pro Ala Ala
    1175                1180                1185

```
Tyr Pro Asp Ser Lys Ser Gln Pro His Val Gln Val Ala Leu Arg
    1190            1195                1200
Met Arg Gln Arg Gly Tyr Lys Glu Gly Phe Asn Ala Lys Asp Thr
    1205            1210                1215
Val Pro Tyr Ile Ile Cys Tyr Glu Gln Gly Asn Ala Ser Ser Ala
    1220            1225                1230
Ser Ser Ala Gly Ile Ala Glu Arg Ala Arg His Pro Asp Glu Val
    1235            1240                1245
Lys Ser Glu Gly Ser Arg Trp Leu Val Asp Ile Asp Tyr Tyr Leu
    1250            1255                1260
Ala Gln Gln Ile His Pro Val Val Ser Arg Leu Cys Ala Glu Ile
    1265            1270                1275
Gln Gly Thr Ser Pro Glu Arg Leu Ala Glu Cys Leu Gly Leu Asp
    1280            1285                1290
Pro Ser Lys Tyr Arg Ser Lys Ser Asn Asp Ala Thr Ser Ser Asp
    1295            1300                1305
Pro Ser Thr Ser Leu Leu Phe Ala Thr Ser Asp Glu Glu Ser Lys
    1310            1315                1320
Lys Pro Ala Thr Pro Glu Thr Glu Glu Ser Asp Ser Thr Phe Trp
    1325            1330                1335
Leu Lys Leu His Cys Pro Lys Cys Gln Gln Glu Asp Ser Thr Gly
    1340            1345                1350
Ile Ile Ser Pro Ala Met Ile Ala Asn Gln Val Lys Arg Gln Ile
    1355            1360                1365
Asp Gly Phe Val Ser Met Tyr Tyr Lys Gly Ile Met Val Cys Glu
    1370            1375                1380
Asp Glu Ser Cys Lys His Thr Arg Ser Pro Asn Phe Arg Leu
    1385            1390                1395
Leu Gly Glu Arg Glu Arg Gly Thr Val Cys Pro Asn Tyr Pro Asn
    1400            1405                1410
Cys Asn Gly Thr Leu Leu Arg Lys Tyr Thr Glu Ala Asp Leu Tyr
    1415            1420                1425
Lys Gln Leu Ser Tyr Phe Cys His Ile Leu Asp Thr Gln Cys Ser
    1430            1435                1440
Leu Glu Lys Met Asp Val Gly Val Arg Ile Gln Val Glu Lys Ala
    1445            1450                1455
Met Thr Lys Ile Arg Pro Ala Val Lys Ser Ala Ala Ala Ile Thr
    1460            1465                1470
Arg Ser Ser Arg Asp Arg Cys Ala Tyr Gly Trp Met Gln Leu Thr
    1475            1480                1485
Asp Ile Val Ile
    1490

<210> SEQ ID NO 33
<211> LENGTH: 895
<212> TYPE: PRT
<213> ORGANISM: Arabidopsis thaliana
<220> FEATURE:
<221> NAME/KEY: MISC_FEATURE
<223> OTHER INFORMATION: At3G59420

<400> SEQUENCE: 33

Met Arg Met Phe Glu Thr Arg Ala Arg Glu Trp Ile Leu Leu Val Lys
1               5                   10                  15

Leu Val Leu Phe Thr Ser Ile Trp Gln Leu Ala Ser Ala Leu Gly Ser
            20                  25                  30
```

```
Met Ser Ser Ile Ala Ile Ser Tyr Gly Glu Gly Gly Ser Val Phe Cys
         35                  40                  45
Gly Leu Lys Ser Asp Gly Ser His Leu Val Val Cys Tyr Gly Ser Asn
 50                  55                  60
Ser Ala Ile Leu Tyr Gly Thr Pro Gly His Leu Gln Phe Ile Gly Leu
 65                  70                  75                  80
Thr Gly Gly Asp Gly Phe Met Cys Gly Leu Leu Met Leu Ser His Gln
                 85                  90                  95
Pro Tyr Cys Trp Gly Asn Ser Ala Phe Ile Gln Met Gly Val Pro Gln
                100                 105                 110
Pro Met Thr Lys Gly Ala Glu Tyr Leu Glu Val Ser Ala Gly Asp Tyr
             115                 120                 125
His Leu Cys Gly Leu Arg Lys Pro Ile Val Gly Arg Arg Lys Asn Ser
130                 135                 140
Asn Ile Ile Ser Ser Ser Leu Val Asp Cys Trp Gly Tyr Asn Met Thr
145                 150                 155                 160
Arg Asn Phe Val Phe Asp Lys Gln Leu His Ser Leu Ser Ala Gly Ser
                 165                 170                 175
Glu Phe Asn Cys Ala Leu Ser Ser Lys Asp Lys Ser Val Phe Cys Trp
                 180                 185                 190
Gly Asp Glu Asn Ser Ser Gln Val Ile Ser Leu Ile Pro Lys Glu Lys
                 195                 200                 205
Lys Phe Gln Lys Ile Ala Ala Gly Gly Tyr His Val Cys Gly Ile Leu
             210                 215                 220
Asp Gly Leu Glu Ser Arg Val Leu Cys Trp Gly Lys Ser Leu Glu Phe
225                 230                 235                 240
Glu Glu Glu Val Thr Gly Thr Ser Thr Glu Glu Lys Ile Leu Asp Leu
                 245                 250                 255
Pro Pro Lys Glu Pro Leu Leu Ala Val Val Gly Gly Lys Phe Tyr Ala
             260                 265                 270
Cys Gly Ile Lys Arg Tyr Asp His Ser Ala Val Cys Trp Gly Phe Phe
             275                 280                 285
Val Asn Arg Ser Thr Pro Ala Pro Thr Gly Ile Gly Phe Tyr Asp Leu
290                 295                 300
Ala Ala Gly Asn Tyr Phe Thr Cys Gly Val Leu Thr Gly Thr Ser Met
305                 310                 315                 320
Ser Pro Val Cys Trp Gly Leu Gly Phe Pro Ala Ser Ile Pro Leu Ala
             325                 330                 335
Val Ser Pro Gly Leu Cys Ile Asp Thr Pro Cys Pro Pro Gly Thr His
             340                 345                 350
Glu Leu Ser Asn Gln Glu Asn Ser Pro Cys Lys Phe Thr Gly Ser His
             355                 360                 365
Ile Cys Leu Pro Cys Ser Thr Ser Cys Pro Pro Gly Met Tyr Gln Lys
370                 375                 380
Ser Val Cys Thr Glu Arg Ser Asp Gln Val Cys Val Tyr Asn Cys Ser
385                 390                 395                 400
Ser Cys Ser Ser His Asp Cys Ser Ser Asn Cys Ser Ser Ser Ala Thr
                 405                 410                 415
Ser Gly Gly Lys Glu Lys Gly Lys Phe Trp Ser Leu Gln Leu Pro Ile
             420                 425                 430
Ala Thr Ala Glu Ile Gly Phe Ala Leu Phe Leu Val Ala Val Val Ser
             435                 440                 445
```

```
Ile Thr Ala Ala Leu Tyr Ile Arg Tyr Arg Leu Arg Asn Cys Arg Cys
450                 455                 460

Ser Glu Asn Asp Thr Arg Ser Ser Lys Asp Ser Ala Phe Thr Lys Asp
465                 470                 475                 480

Asn Gly Lys Ile Arg Pro Asp Leu Asp Glu Leu Gln Lys Arg Arg Arg
                485                 490                 495

Ala Arg Val Phe Thr Tyr Glu Glu Leu Glu Lys Ala Ala Asp Gly Phe
    500                 505                 510

Lys Glu Glu Ser Ile Val Gly Lys Gly Ser Phe Ser Cys Val Tyr Lys
            515                 520                 525

Gly Val Leu Arg Asp Gly Thr Thr Val Ala Val Lys Arg Ala Ile Met
530                 535                 540

Ser Ser Asp Lys Gln Lys Asn Ser Asn Glu Phe Arg Thr Glu Leu Asp
545                 550                 555                 560

Leu Leu Ser Arg Leu Asn His Ala His Leu Leu Ser Leu Leu Gly Tyr
                565                 570                 575

Cys Glu Glu Cys Gly Glu Arg Leu Leu Val Tyr Glu Phe Met Ala His
    580                 585                 590

Gly Ser Leu His Asn His Leu His Gly Lys Asn Lys Ala Leu Lys Glu
            595                 600                 605

Gln Leu Asp Trp Val Lys Arg Val Thr Ile Ala Val Gln Ala Ala Arg
610                 615                 620

Gly Ile Glu Tyr Leu His Gly Tyr Ala Cys Pro Val Ile His Arg
625                 630                 635                 640

Asp Ile Lys Ser Ser Asn Ile Leu Ile Asp Glu Glu His Asn Ala Arg
                645                 650                 655

Val Ala Asp Phe Gly Leu Ser Leu Leu Gly Pro Val Asp Ser Gly Ser
    660                 665                 670

Pro Leu Ala Glu Leu Pro Ala Gly Thr Leu Gly Tyr Leu Asp Pro Glu
            675                 680                 685

Tyr Tyr Arg Leu His Tyr Leu Thr Thr Lys Ser Asp Val Tyr Ser Phe
690                 695                 700

Gly Val Leu Leu Leu Glu Ile Leu Ser Gly Arg Lys Ala Ile Asp Met
705                 710                 715                 720

His Tyr Glu Glu Gly Asn Ile Val Glu Trp Ala Val Pro Leu Ile Lys
                725                 730                 735

Ala Gly Asp Ile Asn Ala Leu Leu Asp Pro Val Leu Lys His Pro Ser
    740                 745                 750

Glu Ile Glu Ala Leu Lys Arg Ile Val Ser Val Ala Cys Lys Cys Val
            755                 760                 765

Arg Met Arg Gly Lys Asp Arg Pro Ser Met Asp Lys Val Thr Thr Ala
770                 775                 780

Leu Glu Arg Ala Leu Ala Gln Leu Met Gly Asn Pro Ser Ser Glu Gln
785                 790                 795                 800

Pro Ile Leu Pro Thr Glu Val Val Leu Gly Ser Ser Arg Met His Lys
                805                 810                 815

Lys Ser Trp Arg Ile Gly Ser Lys Arg Ser Gly Ser Glu Asn Thr Glu
    820                 825                 830

Phe Arg Gly Gly Ser Trp Ile Thr Phe Pro Ser Val Thr Ser Ser Gln
            835                 840                 845

Arg Arg Lys Ser Ser Ala Ser Glu Gly Asp Val Ala Glu Glu Glu Asp
850                 855                 860

Glu Gly Arg Lys Gln Gln Glu Ala Leu Arg Ser Leu Glu Glu Glu Ile
```

-continued

```
                865                 870                 875                 880
        Gly Pro Ala Ser Pro Gly Gln Ser Leu Phe Leu His His Asn Phe
                            885                 890                 895

<210> SEQ ID NO 34
<211> LENGTH: 451
<212> TYPE: PRT
<213> ORGANISM: Arabidopsis thaliana
<220> FEATURE:
<221> NAME/KEY: MISC_FEATURE
<223> OTHER INFORMATION: At3G59430

<400> SEQUENCE: 34

Met Val Arg Lys Glu Asp Val Asp Phe Tyr Cys Gly Phe Ser Arg Lys
1               5                   10                  15

Glu Leu Gln Ser Leu Cys Lys Lys Tyr Asn Leu Pro Ala Asn Arg Ser
            20                  25                  30

Ser Ser Asp Met Ala Glu Ser Leu Ala Ser Tyr Phe Glu Lys Asn Asn
        35                  40                  45

Leu Asn Pro Val Ser Phe Gly Val Pro Gly Asn Gln Asp Ser Ser Ala
    50                  55                  60

Thr Thr Ser Arg Ala Pro Ala Ile Arg Thr Trp Asn Val Lys Arg Asp
65                  70                  75                  80

Ser Tyr Gly Asn Lys Leu Asp Val Pro Arg Glu Asp Tyr Val Gln Gly
                85                  90                  95

Ala Val Ala Arg Glu Pro Gly Ile Ile Leu Gly Asn Asn Thr Pro Tyr
            100                 105                 110

Gln Glu Arg Asn Gly Asn Asp Gly Leu Ile Asp Phe Thr Ser Ala Pro
        115                 120                 125

Pro Tyr Met Arg Lys Leu Asn Glu Lys Gly Pro Thr Ala Asn Ser Lys
    130                 135                 140

Arg Ala Asp Ser Arg Leu Glu Asn Arg Met Arg Asp Val Asp Ser Gly
145                 150                 155                 160

Asp Asn Pro Ser Ser Ser Ser Phe Glu Phe His Val Ser Leu Glu Glu
                165                 170                 175

Gly Ile Ser Leu Ser Val Asp Leu Asn Phe Asn Pro Ser Asp Trp Ile
            180                 185                 190

Asn Ser Met Arg Asp Glu Val Asn Val Cys Asp Ser Met Arg Arg Arg
        195                 200                 205

Lys Ser Pro His Ser Asp Leu Gly Ile Thr Glu Cys Lys Lys Gln Lys
    210                 215                 220

Ser Ser Gly Gln Asp Thr Asp Gly His Val Arg Arg Glu Ser Ser Leu
225                 230                 235                 240

Ser Pro Pro Met Lys Asp Asn Ala His Leu Pro Ser Asp His His Pro
                245                 250                 255

Asn Gly Glu Arg Ser Leu Ala Ser Ser Ala Ile Glu Pro Cys Asn Arg
            260                 265                 270

Ile Lys Glu Ser Ser Asp Thr Cys Lys Glu Lys Ser Gly Leu Asn Leu
        275                 280                 285

Ser Ile Pro Asp Ser Ser Gly Pro Cys Gln Ile Ala Ser Ser Cys Val
    290                 295                 300

Glu Ser Tyr Ser Lys Ser Cys Cys Val Asn Pro Val Asp Leu Asp Cys
305                 310                 315                 320

Ile Ile Pro Pro Gly Lys Lys Leu Ala Ser Glu Ser Asp Met Val Ala
                325                 330                 335
```

```
Ala Glu Gln Asn His Ser Ala Gly Asp Leu Leu Val Glu Ile Pro Lys
            340             345                 350

Asn Pro Ser Met Glu Ser Phe Gln Ile Val Gly Asn Ser Ser Thr Val
        355             360                 365

Ile Cys Pro Arg Gly Ala Gly Ser Glu Leu Ser Ser Ser Glu Ala Glu
        370             375             380

Ala Tyr His Ser Asn Gln Pro Cys Ser Pro Arg Lys Thr Ser Arg Ser
385             390             395                 400

Ser Thr Ile Ser Ser Pro Glu Phe Ile Ile Asp Arg Glu Ser Thr Ser
            405             410                 415

Tyr Ser Glu Ser Phe Lys Phe Arg Cys Asn Gly Gly Lys Ser Leu Pro
            420             425                 430

Pro Asn Thr Glu Glu Gln Glu Lys Ser Glu Val Leu Ser Glu Gln Ala
            435             440                 445

Arg Ser Glu
        450
```